(12) United States Patent
Kannan et al.

(10) Patent No.: US 11,561,178 B2
(45) Date of Patent: Jan. 24, 2023

(54) ARTIFICIAL FLUORESCENT IMAGE SYSTEMS AND METHODS

(71) Applicant: Tempus Labs, Inc., Chicago, IL (US)

(72) Inventors: Madhavi Kannan, Chicago, IL (US); Brian Larsen, Chicago, IL (US); Aly A. Khan, Chicago, IL (US); Ameen Salahudeen, Chicago, IL (US)

(73) Assignee: Tempus Labs, Inc., Chicago, IL (US)

( * ) Notice: Subject to any disclaimer, the term of this patent is extended or adjusted under 35 U.S.C. 154(b) by 0 days.

(21) Appl. No.: 17/301,975

(22) Filed: Apr. 20, 2021

(65) Prior Publication Data

US 2021/0325308 A1    Oct. 21, 2021

Related U.S. Application Data

(60) Provisional application No. 63/012,885, filed on Apr. 20, 2020.

(51) Int. Cl.
| | | |
|---|---|---|
| *G01N 21/64* | (2006.01) | |
| *G01N 33/50* | (2006.01) | |
| *G02B 21/12* | (2006.01) | |
| *G02B 21/00* | (2006.01) | |
| *G01N 21/552* | (2014.01) | |
| *G06T 7/00* | (2017.01) | |
| *G06N 20/00* | (2019.01) | |
| *G16H 30/00* | (2018.01) | |
| *G06V 20/69* | (2022.01) | |

(52) U.S. Cl.
CPC ....... *G01N 21/6458* (2013.01); *G01N 21/553* (2013.01); *G01N 33/5011* (2013.01); *G02B 21/0076* (2013.01); *G02B 21/12* (2013.01); *G06N 20/00* (2019.01); *G06T 7/0012* (2013.01); *G06V 20/69* (2022.01); *G16H 30/00* (2018.01); *G06T 2207/30024* (2013.01)

(58) Field of Classification Search
CPC ............. G01N 21/6458; G01N 21/553; G01N 33/5011; G16H 30/00; G06N 20/00; G06V 20/69; G02B 21/0076; G02B 21/12; G06T 7/0012

See application file for complete search history.

(56) References Cited

U.S. PATENT DOCUMENTS

| | | |
|---|---|---|
| 2010/0158330 A1 | 6/2010 | Guissin |
| 2012/0200694 A1* | 8/2012 | Garsha ............ G01N 21/6456 348/79 |
| 2012/0200695 A1 | 8/2012 | Yamane |
| 2015/0329829 A1 | 11/2015 | Shen |
| 2017/0336392 A1 | 11/2017 | Theodorakis |
| 2019/0065905 A1 | 2/2019 | Raphaeli |
| 2019/0291112 A1* | 9/2019 | Wong ............. B01L 3/502707 |
| 2020/0211716 A1 | 7/2020 | Lefkofsky |
| 2020/0365232 A1 | 11/2020 | Jaros |
| 2020/0381087 A1 | 12/2020 | Ozeran |
| 2021/0090694 A1 | 3/2021 | Colley |
| 2021/0172931 A1 | 6/2021 | Larsen |

FOREIGN PATENT DOCUMENTS

| | | |
|---|---|---|
| EP | 2412800 A1 | 2/2012 |
| EP | 2743345 A1 | 6/2014 |
| WO | 2009022907 A2 | 2/2009 |
| WO | 2010090513 A2 | 8/2010 |
| WO | 2012014076 A2 | 2/2012 |
| WO | 2012168930 A2 | 12/2012 |
| WO | 2013093812 A2 | 6/2013 |
| WO | 2014159356 A1 | 10/2014 |
| WO | 2015173425 A1 | 11/2015 |
| WO | 2016083612 A1 | 6/2016 |
| WO | 2016083613 A2 | 6/2016 |
| WO | 2017149025 A1 | 9/2017 |
| WO | 2017220586 A1 | 12/2017 |
| WO | 2019018693 A2 | 1/2019 |
| WO | 2019035766 A1 | 2/2019 |
| WO | 2019094230 A1 | 5/2019 |
| WO | 2019152767 A1 | 8/2019 |
| WO | 2021113846 A1 | 6/2021 |

OTHER PUBLICATIONS

Bailo, O. et al. "Red blood cell image generation for data augmentation using conditional generative adversarial networks." Proceedings of the IEEE/CVF Conference on Computer Vision and Pattern Recognition Workshops. 2019.
Brunet, D., et al. "On the mathematical properties of the structural similarity index." IEEE Transactions on Image Processing 21.4 (2012): 1488-1499.
Ihle, S., et al. "UDCT: Unsupervised data to content transformation with histogram-matching cycle-consistent generative adversarial networks." bioRxiv (2019): 563734.
Ouyang, W., et al. "Deep learning massively accelerates super-resolution localization microscopy." Nature biotechnology 36.5 (2018): 460-468.
Renieblas, G. P., et al. "Structural similarity index family for image quality assessment in radiological images." Journal of medical imaging 4.3 (2017): 035501.
Rivenson, Y., et al. "Virtual histological staining of unlabelled tissue-autofluorescence images via deep learning." Nature biomedical engineering 3.6 (2019): 466-477.
Sampat, M. P., et al. "Complex wavelet structural similarity: A new image similarity index." IEEE transactions on image processing 18.11 (2009): 2385-2401.

(Continued)

*Primary Examiner* — Jerry Lin
(74) *Attorney, Agent, or Firm* — Quarles & Brady LLP

(57) ABSTRACT

The disclosure provides a method of generating an artificial fluorescent image of cells is provided. The method includes receiving a brightfield image generated by a brightfield microscopy imaging modality of at least a portion of cells included in a specimen, applying, to the brightfield image, at least one trained model, the trained model being trained to generate the artificial fluorescent image based on the brightfield image, receiving the artificial fluorescent image from the trained model

30 Claims, 20 Drawing Sheets

(56) References Cited

OTHER PUBLICATIONS

Tsuda, H. et al. "Cell image segmentation by integrating pix2pixs for each class." Proceedings of the IEEE/CVF Conference on Computer Vision and Pattern Recognition Workshops. 2019.
Wang, Z., et al. "Image quality assessment: from error visibility to structural similarity." IEEE transactions on image processing 13.4 (2004): 600-612.
Zhu, J.-Y., et al. "Unpaired Image-to-Image Translation using Cycle-Consistent Adversarial Networks." arXiv preprint arXiv:1703.10593 (2017).
Business Wire. Recursion Pharmaceuticals Announces Research Agreement With Sanofi Genzyme. Apr. 25, 2016. Version accessed Apr. 26, 2016. Available online at https://www.businesswire.com/news/home/20160425005113/en/Recursion-Pharmaceuticals-Announces-Research-Agreement-Sanofi-Genzyme.
Christiansen, Eric M., et al. "In silico labeling: predicting fluorescent labels in unlabeled images." Cell 173.3 (2018):792-803.
El-Melegy, M., et al. "Identification of tuberculosis bacilli in ZN-stained sputum smear images: A deep learning approach." Proceedings of the IEEE/CVF Conference on Computer Vision and Pattern Recognition Workshops. 2019.
Fu, C., et al. "Three Dimensional Fluorescence Microscopy Image Synthesis and Segmentation." arXiv preprint arXiv:1801.07198 (2018).
Gilead. Gilead and insitro Announce Strategic Collaboration to Discover and Develop Novel Therapies for Nonalcoholic Steatohepatitis. Press Release. Apr. 16, 2019. Version accessed Jun. 28, 2020. https://web.archive.org/web/20200628202335/https://www.gilead.com/news-and-press/press-room/press-releases/2019/4/gilead-and-insitro-announce-strategic-collaboration-to-discover-and-develop-novel-therapies-for-nonalcoholic-steatohepatitis.
Guo, S.-M., et al. "Revealing architectural order with quantitative label-free imaging and deep neural networks." BioRxiv (2019): 631101.
Han, L. et al. "Transferring microscopy image modalities with conditional generative adversarial networks." Proceedings of the IEEE Conference on Computer Vision and Pattern Recognition Workshops. 2017.
International Searching Authority. International Search Report and Written Opinion for application PCT/US2020/063619, dated Mar. 9, 2021. 11 pages.
Isola, P., et al. "Image-to-Image Translation with Conditional Adversarial Networks." arXiv preprint arXiv:1611.07004 (2016).
Kim, D., et al. "AI-powered transmitted light microscopy for functional analysis of live cells." Scientific reports 9.1 (2019): 1-9.
Lee, H.-C., et al. "Enhancing high-content imaging for studying microtubule networks at large-scale." arXiv preprint arXiv:1910.00662 (2019).
Leopold, G. Intel Adds Memory to Deep Learning for Drug Discovery. May 31, 2018. Version accessed Jun. 20, 2020 at https://web.archive.org/web/20200620144314/https://www.datanami.com/2018/05/31/intel-adds-memory-to-deep-learning-for-drug-discovery/.
Nguyen, T. C., et al. "Virtual organelle self-coding for fluorescence imaging via adversarial learning." Journal of biomedical optics 25.9 (2020): 096009.
Ounkomol, C., et al. "Label-free prediction of three-dimensional fluorescence images from transmitted-light microscopy." Nature methods 15.11 (2018): 917-920.
U.S. Appl. No. 16/693,117, titled "Tumor Organoid Culture Compositions, Systems, and Methods" and filed Nov. 22, 2019.
U.S. Appl. No. 62/804,724, titled "Therapeutic Suggestion Improvements Gained Through Genomic Biomarker Matching Plus Clinical History", filed Feb. 12, 2019.
U.S. Appl. No. 62/924,515, titled "Artificial Intelligence Assisted Precision Medicine Enhancements to Standardized Laboratory Diagnostic Testing", and filed Oct. 22, 2019.
U.S. Appl. No. 62/924,621, titled "Systems and Methods for Predicting Therapeutic Sensitivity" and filed Oct. 22, 2019.
U.S. Appl. No. 62/944,292, titled "Large Scale Phenotypic Organoid Analysis" and filed Dec. 5, 2019.
Wang, Z. et al. "Multiscale structural similarity for image quality assessment." The Thrity-Seventh Asilomar Conference on Signals, Systems & Computers, 2003. vol. 2. Ieee, 2003.
Zhang, Z., et al. "Label-Free Estimation of Therapeutic Efficacy on 3D Cancer Spheres Using Convolutional Neural Network Image Analysis." Analytical chemistry 91.21 (2019): 14093-14100.
Zhao, H., et al. "Loss functions for image restoration with neural networks." IEEE Transactions on computational imaging 3.1 (2016): 47-57.
Zhao, H., et al. "Loss functions for neural networks for image processing." arXiv preprint arXiv:1511.08861 (2015).
Andor et al. "Pan-cancer analysis of the extent and consequences of intra-tumor heterogeneity", Nat Med., vol. 22, pp. 105-113 (2016).
Ashford, M., "Harvard Team Advancing Algorithmic Signature to Improve PARP Inhibitor Patient Selection", genomeweb, Apr. 18, 2019, 3 pages.
Bein et al. "Microfluidic Organ-on-a-Chip models of Human Intestine", Cellular and Molecular Gastroenterology and Heptatology, vol. 5, No. 4, pp. 659-668 (2018).
Ben-David et al. "Genetic and Trascriptional evolution alters cancer cell line drug response", Nature, vol. 560, pp. 325-330 (2018).
Boj et al. "Organoid Models of Human and Mouse Ductal Pancreatic Cancer", Cell, vol. 160, pp. 324-338 (2015).
Bozic et al. "Timing and heterogeneity of mutations associated with drug resistance in metastic cancers" PNAS, vol. 111, No. 45, pp. 15964-15968 (2014).
Brayer et al. "Recurrent Fusions in MYB and MYBL1 Define a Common, Transcription Factor-Driven Oncogenic Pathway in Salivary Gland Adenoid Cystic Carcinoma" Cancer Discov., vol. 6, pp. 176-187 (2016).
Brenan, L., et al. "Phenotypic characterization of a comprehensive set of MAPK1/ERK2 missense mutants", Cell Rep., Oct. 18, 2016, 23 pages.
Breslin et al. "Three-dimensional cell culture: the missing link in drug discovery", Drug Discovery Today, vol. 18, Nos. 5/6 (2013).
Bronkhorst, A.J. et al. "Characterization of the cell-free DNA released by cultured cancer cells", Biochimica et Biophysica Acta 1863 (2016) 157-165 (Year: 2016).
Broutier et al. "Human Primary Liver Cancer-derived Organoid Cultures for disease modelling and drug screening" Nat. Med., vol. 23, pp. 1424-1435 (2017).
Burgess et al. "RNA extraction from self-assembling peptide hydrogels to allow qPCR analysis of encapsulated cells" PLOS One, pp. 1-19, (2018).
Cardea's Tech+Bio Infrastructure, Gardea Bio I Graphene-based, Biology-gated Transistor Technology, https://cardeabio.com/technology/, 5 pages. Version Capture Mar. 3, 2021. Available online at http://web.archive.org/web/20210303200037/https://cardeabio.com/technology/.
Celli, J. P., et al. "An imaging-based platform for high-content, quantitative evaluation of therapeutic response in 3D tumour models." Scientific reports 4.1 (2014): 1-10.
Chomczynski et al. "The single-step method of RNA isolation by acid guanidinium thiocyanate-phenol-chloroform extraction: twenty-something years on", Nature Protocols, vol. 1, No. 2, pp. 581-585 (2006).
Chowell et al. "When (distant) relatives stay too long: implications for cancer medicine", Genome Biology, vol. 17, pp. 1-3 (2016).
De Lau et al. "The R-spondin protein family", Genome Biology, vol. 13, pp. 1-10 (2012).
Dijkstra, K. K., et al. "Generation of Tumor-Reactive T Cells by Co-culture of Peripheral Blood Lymphocytes and Tumor Organoids", CellPress, Sep. 6, 2018, Cell 174, pp. 1586-1598.
Driehuis et al. "Oral Mucosal Organoids as a Potential Platform for Personalized Cancer Therapy", Cancer Discovery, vol. 9, pp. 852-871 (2019).
Drost et al. "Organoids in cancer research", Nature Reviews, vol. 18, pp. 407-418 (2018).
Duda et al. "Pattern Classification", Second Edition, 735 pages. 2000.

(56) References Cited

OTHER PUBLICATIONS

Eder et al. 3D Hanging Drop Culture to Establish Prostate Cancer Organoids, 3D Cell Culture: Methods and Protocols, Methods in Molecular Biology, vol. 1612, pp. 167-175. 2017.
Eke et al. "Radiobiology goes 3D: How ECM and cell morphology impact on cell survival after irradiation", Radiotherapy and Oncology, vol. 99, pp. 271-278 (2011).
Findlay, G. M., et al. "Accurate classification of BRCA1 variants with saturation genome editing", Nature, Oct. 2018, 32 pages.
Findlay, G. M., et al. "Saturation Editing of Genomic Regions by Multiplex Homology-Directed Repair", Nature, Sep. 4, 2014, 24 pages.
Finotello et al. "Measuring differential gene expression with RNA-seq: challenges and strategies for data analysis", Briefings in Functional Genomics, vol. 14, pp. 130-142 (2014).
Fuji et al. "A Colorectal Tumor Organoid Library Demonstrates Progressive Loss of Niche Factor Requirements during Tumorigenesis", Cell Stem Cell, vol. 18, pp. 827-838 (2016).
Ganesh et al. "A rectal cancer organoid platform to study individual responses to chemoradiation", Nature Medicine, 25.10 (2019): 1607-1614.
Gao et al. "Organoid cultures derived from patients with advanced prostate cancer", Cell, vol. 159, pp. 176-187 (2014).
Garalde et al. "Highly parallel direct RNA sequencing on an array of nanopores", Nature Methods, vol. 15, (2018): 201-206.
Giacomelli, A. O., et al. "Mutational processes shape the landscape of TP53 mutations in human cancer", Nat Genet, Oct. 2018, 20 pages.
Goodspeed et al. "Tumor-Derived Cell Lines as Molecular Models of Cancer Pharmacogenomics", Mol. Cancer. Res., vol. 14, pp. 3-13 (2016).
Gramont et al. "Novel TGF-/3 inhibitors ready for prime time in onco-immunology", Oncoimmunology, vol. 6, pp. e1257453 (2017).
Gulhan, D. C., et al. "Detecting the mutational signature of homologous recombination deficiency in clinical samples", Technical Report, Nature Genetics, vol. 51, May 2019, pp. 912-919.
International Searching Authority. International Search Report and Written Opinion for application PCT/US2020/063667, dated May 14, 2021. 14 pages.
Islam et al. "Quantitative single-cell RNA-seq with unique molecular identifiers", Nature Methods, vol. 11, No. 2, pp. 163-166 (2014).
Jabs et al. "Screening drug effects in patient-derived cancer cells links organoid responses to genome alterations", Mol. Systems Biology, vol. 13, pp. 1-16 (2017).
Jenkins, et al. "Ex Vivo Profiling of PD-1 Blockade Using Organotypic Tumor Spheroids", Cancer Discov., Feb. 2018, 36 pages.
Kivioja et al. "Counting absolute numbers of molecules using unique molecular identifiers", Nature Methods, vol. 9, No. 1, pp. 72-74 (2012).
Kohsaka, S., et al. "A method of high-throughput functional evaluation of EGFR gene variants of unknown significance in cancer", Science Translational Medicine I Research Resource, Med. 9, Nov. 15, 2017, 12 pages.
Korenchuk et al. "VCaP, A Cell-Based Model System of Human Prostate Cancer", In Vivo, vol. 15, pp. 163-168 (2001).
Landau et al. "Evolution and impact of subclonal mutations in chronic lymphocytic leukemia", Cell, vol. 152, pp. 714-726 (2013).
Lee et al. "Tumor evolution and drug response in patient-derived organoid models of bladder cancer", Cell, vol. 173, pp. 515-528 (2018).
Li, X. et al. "Organoid cultures recapitulate esophageal adenocarcinoma heterogeneity providing a model for clonality studies and precision therapeutics" Nature Communications, (2018) 9:2983, pp. 1-11 (Year: 2018).
Lin et al. "mRNA/cDNA Library Construction Using RNA-Polymerase Cycling Reaction", Methods in Molecular Biology, vol. 221, pp. 129-143. 2003.
Liu et al. "The Cross-contaminated Cell Lines of Adenoid Cystic Carcinoma: A Crucial Concern", Translational Surgery, vol. 2, pp. 10-13 (2017).
Liu, Q., et al. "Automated counting of cancer cells by ensembling deep features." Cells 8.9 (2019): 1019.
Maley et al. "Genetic clonal diversity predicts progression to esophageal adenocarcinoma", Nature Genetics, vol. 38, pp. 468-473 (2006).
Matreyek, K. A., et al. "Multiplex Assessment of Protein Variant Abundance by Massively Parallel Sequencing", Nat Genet., Jun. 2018, 27 pages.
Matsumoto, N. et al. "C3a enhances the formation of intestinal organoids through C3aR1." Frontiers in immunology 8 (2017): 1046.
Mcconnell et al. "Construction of a representative cDNA library from mRNA isolated from mouse oocytes", FEBS, vol. 195, pp. 199-202 (1986).
Mccune and Grace "Distance Measures", Chapter 6, pp. 45-57 (2002).
Mighell, T. L., et al. "A Saturation Mutagenesis Approach to Understanding PTEN Lipid Phosphatase Activity and Genotype-Phenotype Relationships", The American Journal of Human Genetics 102, May 3, 2018, pp. 943-955.
Mootha et al. "PGC-1a-responsive genes involved in oxidative phosphorylation are coordinately downregulated in human diabetes", Nature genetics, vol. 34, pp. 267-273 (2003).
Nagalakshmi et al. "The Transcriptional Landscape of the Yeast Genome Defined by RNA Sequencing", Science, vol. 320, pp. 1344-1349 (2008).
Nagle et al. "Patient-derived tumor organoids for prediction of cancer treatment response", Seminars in Cancer Biology, vol. 15, pp. 258-264 (2018).
Nam, M.-O., et al. "Effects of a small molecule R-spondin-1 substitute RS-246204 on a mouse intestinal organoid culture." Oncotarget 9.5 (2018): 6356.
Neal, J. T., et al. "Organoid modeling of the tumor immune microenvironment." Cell 175.7 (2018): 1972-1988.
Niederst et al. "Bypass Mechanisms of Resistance to Receptor Tyrosine Kinase Inhibition in Lung Cancer", Sci Signal, vol. 6, pp. 1-12 (2014).
Oh et al. "An improved method for constructing a full-length enriched cDNA library using small amounts of total RNA as a starting material", Experimental and Molecular Medicine, vol. 35, pp. 586-590 (2003).
Ooft, S. N., et al. "Patient-derived organoids can predict response to chemotherapy in metastatic colorectal cancer patients." Science translational medicine 11.513 (2019): eaay2574.
Ou, S.-H. I. et al. "Liquid Biopsy to Identify Actionable Genomic Alterations" American Society of Clinical Oncology Educational Book 38 (May 23, 2018) 978-997 (Year: 2018).
Ozsolak et al. "Direct RNA sequencing", Nature, vol. 461, pp. 814-818 (2009).
Pereira et al. "The somatic mutation profiles of 2,433 breast cancers refines their genomic and transcriptomic landscapes", Nature Communications, vol. 7, pp. 1-15 (2016).
Pflug et al. "TRUmiCount: correctly counting absolute numbers of molecules using unique molecular identifiers", Bioinformatics, vol. 24, pp. 3137-3144 (2018).
Poeckh et al. "Adsorption and elution characteristics of nucleic acids on silica surfaces and their use in designing a miniaturized purification unit", Anal. Biochem., vol. 15, pp. 253-262 (2008).
Puca et al. "Patient derived organoids to model rare prostate cancer phenotypes", Nature Communications, vol. 9, pp. 1-10 (2018).
Rio et al. "Enrichment of Poly(A) mRNA Using Immobilized Oligo(dT)", Cold Spring Harbor Laboratory Press, vol. 2010, Issue 7, pp. 1-3 (2010).
Sachs et al. "A Living Biobank of Breast Cancer Organoids Captures Disease Heterogeneity", Cell, vol. 172, pp. 373-386 (2018).
Sato, T., et al. "Single Lgr5 stem cells build crypt-villus structures in vitro without a mesenchymal niche", Nature, vol. 459, May 14, 2009, pp. 262-265.
Sato, T., et al. "Long-term Expansion of Epithelial Organoids From Human Colon, Adenoma, Adenocarcinoma, and Barrett's Epithelium", Gastroenterology, vol. 141, No. 5, Nov. 2011, pp. 1762-1772.

(56) References Cited

OTHER PUBLICATIONS

Serrati et al. "Next-generation sequencing: advances and applications in cancer diagnosis". OncoTargets and Therapy, vol. 9, pp. 7355-7365 (2016).

Shendure et al. "Next-generation DNA sequencing", Nature Biotechnology, vol. 26, pp. 1135-1145 (2008).

Subramanian et al. "Gene set enrichment analysis: A knowledge-based approach for interpreting genome-wide expression profiles", PNAS, vol. 102, No. 43, pp. 15545-15550 (2005).

Supplementary Information for Li, X. et al, Nature Communications vol. 9, Article No. 2983 (Jul. 30, 2018), online at https://www.nature.com/articles/s41467-018-05190-9#Sec26, 11 printed pages. (Year: 2018).

Supplementary Materials for Vlachogiannis, G. et al. "Patient-derived organoids model treatment response of metastatic gastrointestinal cancers" (V published Feb. 23, 2018, Science 359, 920) from www.sciencemag.org/content/359/6378/920/suppl/DC1. 47 pages printed (Year: 2018).

Tuveson et al. "Cancer modeling meets human organoid technology", Science, vol. 364, pp. 952-955 (2019).

Urbischek et al. "Organoid culture media formulated with growth factors of defined cellular activity", Scientific Reports, vol. 9, pp. 1-11 (2019).

Van De Wetering et al. "Prospective derivation of a Living Organoid Biobank of colorectal cancer patients", Cell, vol. 161, pp. 933-945 (2015).

Vlachogiannis et al. "Patient-derived organoids model treatment response of metastatic gastrointestinal cancers", Science, vol. 359, pp. 920-926 (2018).

Wang et al. "RNA-Seq: a revolutionary tool for transcriptomics", Nat Rev Genet., vol. 10, pp. 57-63 (2009).

Xu et al. "Organoid technology and applications in cancer research", Journal of Hematology & Oncology, vol. 11, pp. 1-15 (2018).

Yan et al. "A Comprehensive Human Gastric Cancer Organoid Biobank Captures Tumor Subtype Heterogeneity and Enables Therapeutic Screening", Cell Stem Cell, vol. 23, pp. 882-897 (2018).

Yancovitz, M. et al. "Intra- and Inter-Tumor Heterogeneity of BRAFV600E Mutations in Primary and Metastatic Melanoma" PLoS One, Jan. 2012, vol. 7, issue 1 (Year: 2012).

Yao et al. "Patient-Derived Organoids Predict Chemoradiation Responses of Locally Advanced Rectal Cancer", Cell Press, vol. 26, pp. 1-10 (2020).

Zhang et al. "Intra-tumor Heterogeneity in Localized Lung Adenocarcinomas Delineated by Multi-region Sequencing", Science, vol. 346, pp. 256-259 (2014).

* cited by examiner

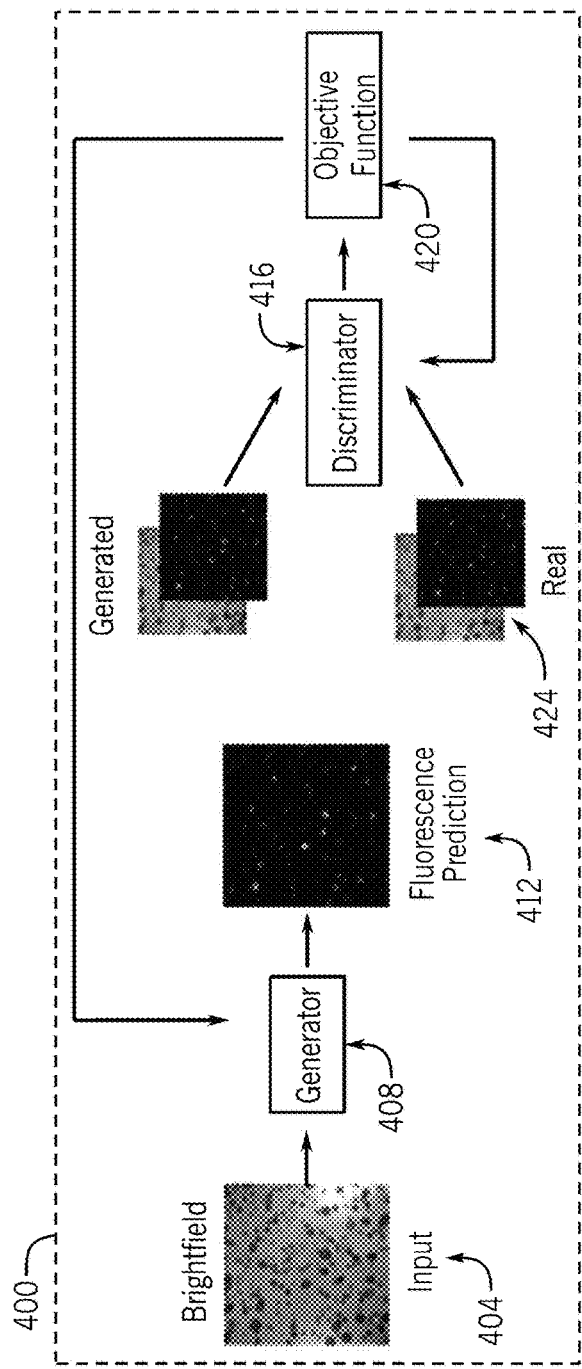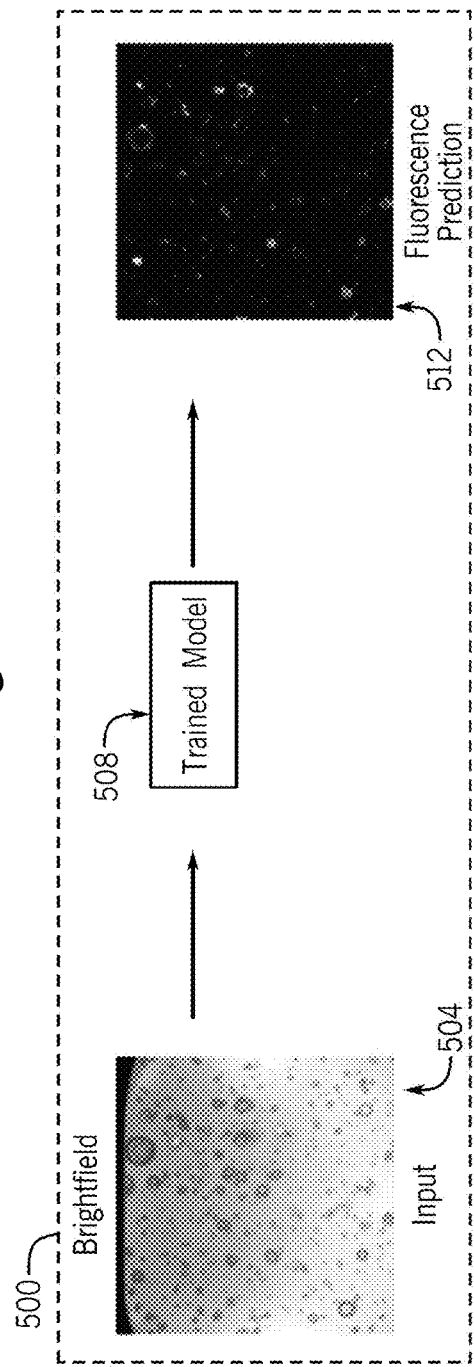

Assay:1B

|   | 1 | 2 | 3 | 4 | 5 | 6 | 7 | 8 | 9 | 10 | 11 | 12 | 13 |
|---|---|---|---|---|---|---|---|---|---|----|----|----|----|
| A | PBS | 0.1% DMSO | 10pM | 10pM | 10pM | 100pM | 100pM | 100pM | 1nM | 1nM | 1nM | 10nM | 10nM |
| B | PBS | 0.1% DMSO | 10pM | 10pM | 10pM | 100pM | 100pM | 100pM | 1nM | 1nM | 1nM | 10nM | 10nM |
| C | PBS | 0.1% DMSO | 10pM | 10pM | 10pM | 100pM | 100pM | 100pM | 1nM | 1nM | 1nM | 10nM | 10nM |
| D | PBS | 0.1% DMSO | 10pM | 10pM | 10pM | 100pM | 100pM | 100pM | 1nM | 1nM | 1nM | 10nM | 10nM |
| E | PBS | 0.1% DMSO | 10pM | 10pM | 10pM | 100pM | 100pM | 100pM | 1nM | 1nM | 1nM | 10nM | 10nM |
| F | PBS | 0.1% DMSO | 10pM | 10pM | 10pM | 100pM | 100pM | 100pM | 1nM | 1nM | 1nM | 10nM | 10nM |
| G | PBS | 0.1% DMSO | 10pM | 10pM | 10pM | 100pM | 100pM | 100pM | 1nM | 1nM | 1nM | 10nM | 10nM |
| H | PBS | 0.1% DMSO | 10pM | 10pM | 10pM | 100pM | 100pM | 100pM | 1nM | 1nM | 1nM | 10nM | 10nM |
| I | PBS | Staurospor | 10pM | 10pM | 10pM | 100pM | 100pM | 100pM | 1nM | 1nM | 1nM | 10nM | 10nM |
| J | PBS | Staurospor | 10pM | 10pM | 10pM | 100pM | 100pM | 100pM | 1nM | 1nM | 1nM | 10nM | 10nM |
| K | PBS | Staurospor | 10pM | 10pM | 10pM | 100pM | 100pM | 100pM | 1nM | 1nM | 1nM | 10nM | 10nM |
| L | PBS | Staurospor | 10pM | 10pM | 10pM | 100pM | 100pM | 100pM | 1nM | 1nM | 1nM | 10nM | 10nM |
| M | PBS | Staurospor | 10pM | 10pM | 10pM | 100pM | 100pM | 100pM | 1nM | 1nM | 1nM | 10nM | 10nM |
| N | PBS | Staurospor | 10pM | 10pM | 10pM | 100pM | 100pM | 100pM | 1nM | 1nM | 1nM | 10nM | 10nM |
| O | PBS | Staurospor | 10pM | 10pM | 10pM | 100pM | 100pM | 100pM | 1nM | 1nM | 1nM | 10nM | 10nM |
| P | PBS | Staurospor | cells | cells | cells | cells | cells | cells | cells | cells | cells | cells | cells |

|   | 14 | 15 | 16 | 17 | 18 | 19 | 20 | 21 | 22 | 23 | 24 |   |   |
|---|----|----|----|----|----|----|----|----|----|----|----|---|---|
| A | 10nM | 100nM | 100nM | 100nM | 1uM | 1uM | 1uM | 10uM | 10uM | 10uM | PBS | Staurosporine | A |
| B | 10nM | 100nM | 100nM | 100nM | 1uM | 1uM | 1uM | 10uM | 10uM | 10uM | PBS | Veliparib (ABT-888) | B |
| C | 10nM | 100nM | 100nM | 100nM | 1uM | 1uM | 1uM | 10uM | 10uM | 10uM | PBS | SB431542 | C |
| D | 10nM | 100nM | 100nM | 100nM | 1uM | 1uM | 1uM | 10uM | 10uM | 10uM | PBS | Selumetinib (AZD6244) | D |
| E | 10nM | 100nM | 100nM | 100nM | 1uM | 1uM | 1uM | 10uM | 10uM | 10uM | PBS | MK-2206 2HCl | E |
| F | 10nM | 100nM | 100nM | 100nM | 1uM | 1uM | 1uM | 10uM | 10uM | 10uM | PBS | PD184352 (CI-1040) | F |
| G | 10nM | 100nM | 100nM | 100nM | 1uM | 1uM | 1uM | 10uM | 10uM | 10uM | PBS | Refametinib (RDEA119, Ba | G |
| H | 10nM | 100nM | 100nM | 100nM | 1uM | 1uM | 1uM | 10uM | 10uM | 10uM | PBS | PD0325901 | H |
| I | 10nM | 100nM | 100nM | 100nM | 1uM | 1uM | 1uM | 10uM | 10uM | 10uM | PBS | KU-55933 (ATM Kinase In | I |
| J | 10nM | 100nM | 100nM | 100nM | 1uM | 1uM | 1uM | 10uM | 10uM | 10uM | PBS | Tozasertib (VX-680, MK-0 | J |
| K | 10nM | 100nM | 100nM | 100nM | 1uM | 1uM | 1uM | 10uM | 10uM | 10uM | PBS | GSK1904529A | K |
| L | 10nM | 100nM | 100nM | 100nM | 1uM | 1uM | 1uM | 10uM | 10uM | 10uM | PBS | Y-27632 2HCl | L |
| M | 10nM | 100nM | 100nM | 100nM | 1uM | 1uM | 1uM | 10uM | 10uM | 10uM | PBS | PF-04217903 | M |
| N | 10nM | 100nM | 100nM | 100nM | 1uM | 1uM | 1uM | 10uM | 10uM | 10uM | PBS | Olaparib (AZD2281, Ku-0 | N |
| O | 10nM | 100nM | 100nM | 100nM | 1uM | 1uM | 1uM | 10uM | 10uM | 10uM | PBS | U0126-EtOH | O |
| P | cells | cells | cells | cells | cells | cells | cells | cells | cells | cells | cells |  | P |

Fig. 14

ARTIFICIAL FLUORESCENT IMAGE SYSTEMS AND METHODS

CROSS-REFERENCE TO RELATED APPLICATIONS

This application claims the benefit of U.S. Application No. 63/012,885, filed Apr. 20, 2020, which is incorporated herein by reference in its entirety.

BACKGROUND

Patient-derived tumor organoid (TO) technologies have been used to create cellular models of diverse cancer types, including colon, breast, pancreatic, liver, lung, endometrial, prostate, and esophagogastric, among others. In addition to advancing fundamental research, TOs have recently been employed for drug development and precision medicine studies.

Tumor organoids can be used to model cancer growth and estimate the effectiveness of different therapies in stopping cancer growth. To monitor the growth of tumor organoids before, during, and after exposure to various anti-cancer therapies, the tumor organoids can be imaged to detect cell death and/or viable cells in a cell culture plate.

Some methods for detecting dead cells or viable cells can include the use of a fluorescent signal, which can be detected by fluorescent microscopy. Fluorescent dyes can be applied to the tumor organoids in order to highlight certain characteristics in the cells and/or make the characteristics easier to detect. The cells can then be imaged using a technique such as fluorescent microscopy. However, fluorescent microscopy can be very time consuming, and the fluorescent dyes used can be toxic to cells, which can artificially inflate the amount of observed cell death that may be falsely attributed to the anti-cancer therapy being tested.

Accordingly, there is a need in the art to automatically analyze tumor organoids and other cellular compositions without the use of fluorescent dyes and/or fluorescent microscopy.

SUMMARY OF DISCLOSURE

Disclosed herein are systems, methods, and mechanisms useful for automatically analyzing tumor organoid and other cellular composition images. In particular, the disclosure provides systems, methods, and mechanisms for generating images of cellular compositions, such as tumor organoids, that approximate fluorescent staining techniques using only raw brightfield images of tumor organoids.

In accordance with some embodiments of the disclosed subject matter, a method of generating an artificial fluorescent image of cells is provided. The method includes receiving a brightfield image generated by a brightfield microscopy imaging modality of at least a portion of cells included in a specimen, applying, to the brightfield image, at least one trained model, the trained model being trained to generate the artificial fluorescent image based on the brightfield image, receiving the artificial fluorescent image from the trained model.

In accordance with some embodiments of the disclosed subject matter, an organoid analysis system including at least one processor and at least one memory is provided. The system is configured to receive a brightfield image generated by a brightfield microscopy imaging modality from at least a portion of cells included in a specimen, apply, to the brightfield image, at least one model trained to generate an artificial fluorescent image based on the brightfield image, the artificial fluorescent image being indicative of whether the cells included in the tumor organoids are alive or dead, and output the artificial fluorescent image to at least one of a memory or a display.

In accordance with some embodiments of the disclosed subject matter, a method of generating an artificial fluorescent image without a fluorescent stain is provided. The method includes receiving a brightfield image generated by a brightfield microscopy imaging modality from at least a portion of cells included in a specimen, applying, to the brightfield image, at least one model trained to generate an artificial fluorescent image based on the brightfield image, the artificial fluorescent image being indicative of whether the cells included in the tumor organoids are alive or dead, and generating a report based on the artificial fluorescent image.

BRIEF DESCRIPTION OF DRAWINGS

FIG. 4 shows an exemplary flow for training a generator to generate an artificial fluorescent image based on an input brightfield image of organoid cells.

FIG. 5 shows an exemplary flow for generating an artificial fluorescent image.

FIG. 14 shows a table representing an exemplary assay or well plate arrangement.

DETAILED DESCRIPTION

Figure 1:
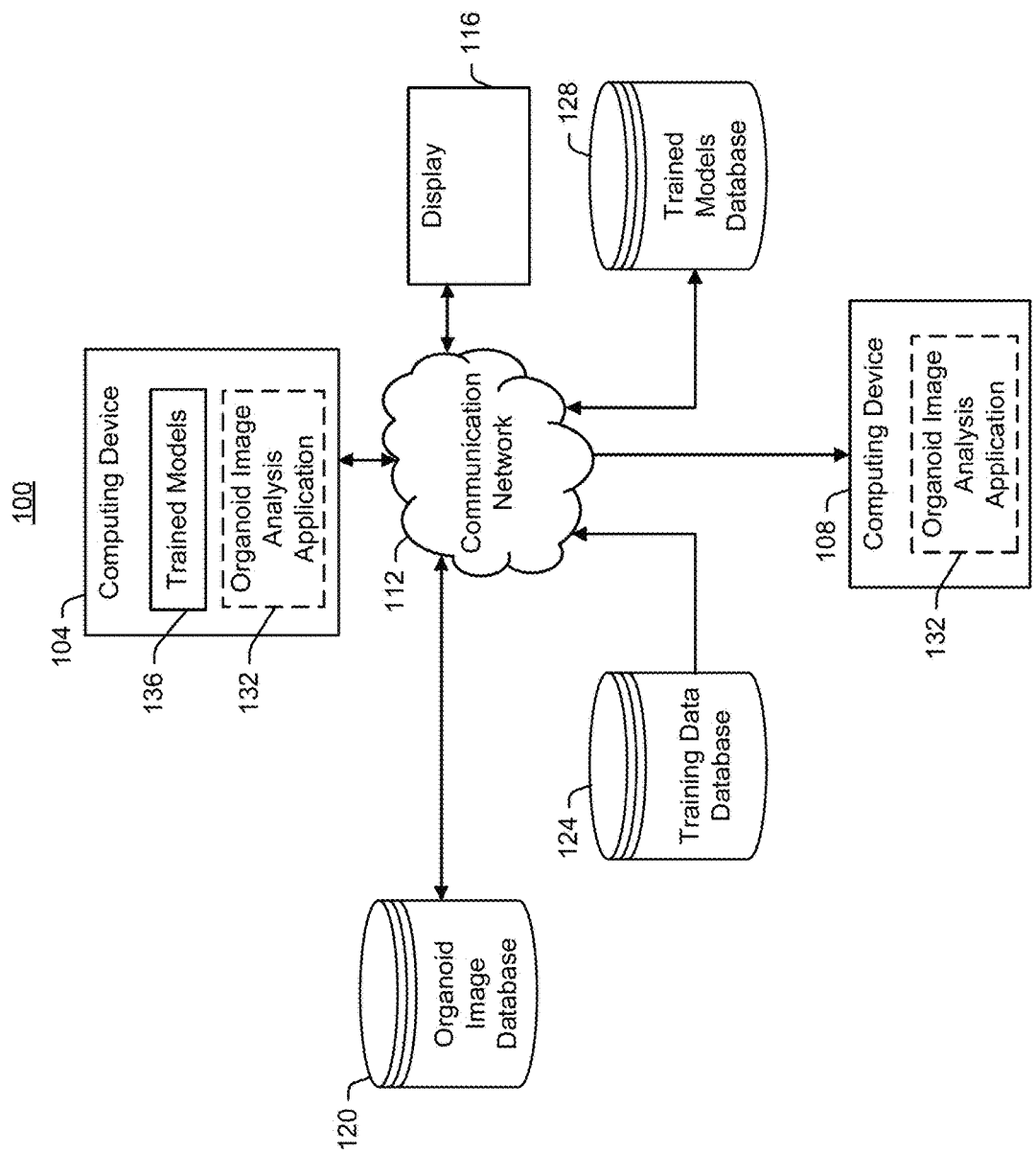
FIG. 1 shows an example of a system for automatically analyzing tumor organoid images.

The various aspects of the subject disclosure are now described with reference to the drawings. It should be understood, however, that the drawings and detailed description hereafter relating thereto are not intended to limit the claimed subject matter to the particular form disclosed. Rather, the intention is to cover all modifications, equivalents, and alternatives falling within the spirit and scope of the claimed subject matter.

In the following detailed description, reference is made to the accompanying drawings which form a part hereof, and in which is shown by way of illustration, specific embodiments in which the disclosure may be practiced. These embodiments are described in sufficient detail to enable those of ordinary skill in the art to practice the disclosure. It should be understood, however, that the detailed description and the specific examples, while indicating examples of embodiments of the disclosure, are given by way of illustration only and not by way of limitation. From this disclosure, various substitutions, modifications, additions, rearrangements, or combinations thereof within the scope of the disclosure may be made and will become apparent to those of ordinary skill in the art.

In accordance with common practice, the various features illustrated in the drawings may not be drawn to scale. The illustrations presented herein are not meant to be actual views of any particular method, device, or system, but are merely idealized representations that are employed to describe various embodiments of the disclosure. Accordingly, the dimensions of the various features may be arbitrarily expanded or reduced for clarity. In addition, some of the drawings may be simplified for clarity. Thus, the drawings may not depict all of the components of a given apparatus (e.g., device) or method. In addition, like reference numerals may be used to denote like features throughout the specification and figures.

Information and signals described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof. Some drawings may illustrate signals as a single signal for clarity of presentation and description. It will be understood by a person of ordinary skill in the art that the signal may represent a bus of signals, wherein the bus may have a variety of bit widths and the disclosure may be implemented on any number of data signals including a single data signal.

The various illustrative logical blocks, modules, circuits, and algorithm acts described in connection with embodiments disclosed herein may be implemented as electronic hardware, computer software, or combinations of both. To clearly illustrate this interchangeability of hardware and software, various illustrative components, blocks, modules, circuits, and acts are described generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the embodiments of the disclosure described herein.

In addition, it is noted that the embodiments may be described in terms of a process that is depicted as a flowchart, a flow diagram, a structure diagram, or a block diagram. Although a flowchart may describe operational acts as a sequential process, many of these acts can be performed in another sequence, in parallel, or substantially concurrently. In addition, the order of the acts may be re-arranged. A process may correspond to a method, a function, a procedure, a subroutine, a subprogram, etc. Furthermore, the methods disclosed herein may be implemented in hardware, software, or both. If implemented in software, the functions may be stored or transmitted as one or more instructions or code on a computer-readable medium. Computer-readable media includes both computer storage media and communication media including any medium that facilitates transfer of a computer program from one place to another.

It should be understood that any reference to an element herein using a designation such as "first," "second," and so forth does not limit the quantity or order of those elements, unless such limitation is explicitly stated. Rather, these designations may be used herein as a convenient method of distinguishing between two or more elements or instances of an element. Thus, a reference to first and second elements does not mean that only two elements may be employed there or that the first element must precede the second element in some manner. Also, unless stated otherwise a set of elements may comprise one or more elements.

As used herein, the terms "component," "system" and the like are intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a computer and the computer can be a component. One or more components may reside within a process and/or thread of execution and a component may be localized on one computer and/or distributed between two or more computers or processors.

The word "exemplary" is used herein to mean serving as an example, instance, or illustration. Any aspect or design described herein as "exemplary" is not necessarily to be construed as preferred or advantageous over other aspects or designs.

Furthermore, the disclosed subject matter may be implemented as a system, method, apparatus, or article of manufacture using standard programming and/or engineering techniques to produce software, firmware, hardware, or any combination thereof to control a computer or processor based device to implement aspects detailed herein. The term "article of manufacture" (or alternatively, "computer program product") as used herein is intended to encompass a computer program accessible from any computer-readable device, carrier, or media. For example, computer readable media can include but are not limited to magnetic storage devices (e.g., hard disk, floppy disk, magnetic strips, etc.), optical disks (e.g., compact disk (CD), digital versatile disk (DVD), etc.), smart cards, and flash memory devices (e.g., card, stick).

Additionally it should be appreciated that a carrier wave can be employed to carry computer-readable electronic data such as those used in transmitting and receiving electronic mail or in accessing a network such as the Internet or a local area network (LAN). Of course, those skilled in the art will recognize many modifications may be made to this configuration without departing from the scope or spirit of the claimed subject matter.

As used herein the terms "biological specimen," "patient sample," and "sample" refer to a specimen collected from a patient. Such samples include, without limitation, tumors, biopsies, tumor organoids, other tissues, and bodily fluids. Suitable bodily fluids include, for example, blood, serum, plasma, sputum, lavage fluid, cerebrospinal fluid, urine, semen, sweat, tears, saliva, and the like. Samples may be collected, for example, via a biopsy, swab, or smear.

The terms "extracted", "recovered," "isolated," and "separated," refer to a compound, (e.g., a protein, cell, nucleic acid or amino acid) that has been removed from at least one component with which it is naturally associated and found in nature.

The terms "enriched" or "enrichment" herein refer to the process of amplifying nucleic acids contained in a sample. Enrichment can be sequence specific or nonspecific (i.e., involving any of the nucleic acids present in a sample).

As used herein, "cancer" shall be taken to mean any one or more of a wide range of benign or malignant tumors, including those that are capable of invasive growth and metastases through a human or animal body or a part thereof, such as, for example, via the lymphatic system and/or the blood stream. As used herein, the term "tumor" includes both benign and malignant tumors and solid growths. Typical cancers include but are not limited to carcinomas, lymphomas, or sarcomas, such as, for example, ovarian cancer, colon cancer, breast cancer, pancreatic cancer, lung cancer, prostate cancer, urinary tract cancer, uterine cancer, acute lymphatic leukemia, Hodgkin's disease, small cell carcinoma of the lung, melanoma, neuroblastoma, glioma, and soft tissue sarcoma of humans.

Fluorescence microscopy is commonly used to detect the presence of specific molecules in a sample. For example, in cell biology, fluorescence microscopy can be used to highlight a specific cellular component (e.g., an organelle) or detect a molecular marker that is indicative of a particular cellular state (e.g., apoptosis, differentiation, or activation of a cell signaling pathway). However, there are several drawbacks that limit the use of fluorescence microscopy. First, use of this technique requires additional time, labor, and reagents (e.g., stains) as compared to transmitted light microscopy, making it a costly bottleneck in high-throughput screening processes. Second, some fluorescent dyes are toxic to cells and can bias the results of certain experiments (e.g., quantification of cell death). Further, cells that were damaged by these dyes can no longer be used in an ongoing experiment, so a greater quantity of cells is required for experiments that involve assaying cells at multiple time points. Third, the time over which a sample can be observed using fluorescence microscopy is limited by photobleaching, a process in which fluorophores lose their ability to fluoresce as they are illuminated.

Fortunately, methods based on transmitted light microscopy largely avoid these problems, as they are relatively fast and inexpensive to use and can capture multiple images of the same living samples at several time points. The term "transmitted light microscopy" is used to refer to any type of microscopy where the light passes from the source to the opposite side of the lens. The simplest of these methods is brightfield microscopy, in which samples are illuminated from below with white light and the transmitted light is observed from above. Use of a standard brightfield microscope is somewhat limited for biological samples that have low contrast. For instance, without the use of stains, the membrane and nucleus are the only features of a mammalian cell that are discernable in a brightfield image. Fortunately, adding optical accessories to a standard brightfield microscope can dramatically enhance image contrast, eliminating the need to kill, fix, and stain samples. One very simple contrast-enhancing method is dark-field microscopy, which works by illuminating the sample with light that will not be collected by the objective lens. For applications in which greater detail is required, phase-contrast microscopy and differential interference contrast microscopy may be employed. These complementary techniques produce high-contrast images of transparent biological samples by using optical systems to convert variations in density or thickness within the sample to differences in contrast in the final image. Importantly, these techniques can be used to reveal small cellular structures, such as nuclei, ribosomes, mitochondria, membranes, spindles, mitotic apparatus, nucleolus, chromosomes, Golgi apparatus, vacuoles, pinocytotic vesicles, lipid droplets, and cytoplasmic granules. Brightfield microscopy can also be augmented with polarized light, which creates contrast in samples comprising materials with different refractive indices (i.e., birefringent samples). Whereas dark-field, phase-contrast, and differential interference contrast microscopy are well suited for imaging live, unstained biological samples, polarized light microscopy is well suited for studying the structure and composition of rocks, minerals, and metals. Notably, any of these contrast-enhancing methods can be combined with optical sectioning techniques, such as confocal microscopy and light sheet microscopy, which produce clear images of focal planes deep within thicker samples (e.g., thick tissues, small organisms), reducing or eliminating the need to physically section samples (e.g., using a microtome).

In the present application, the inventors demonstrate that certain cellular states that are commonly detected using fluorescence microscopy also manifest as subtle morphological features in images produced by transmitted light microscopy. While such features may be difficult or impossible to discern in these images using only the human eye, the inventors show their identification can be automated using a trained model. In the Examples, a trained model is used to predict the percentages of live and dead cells in a sample (i.e., values which would typically be determined using fluorescent stains, such as Caspase-3/7 and TO-PRO-3 stain), using only a brightfield image as input. These visualization methods may then be used in a high-throughput screen for drugs that kill cancer cells within tumor organoids generated from patient tumor samples.

The methods and systems disclosed herein are not limited to this single application, however. The ability to associate subtle morphological features that are present in a transmitted light microscopy image with cellular states of interest is useful in countless applications spanning many diverse fields of study. Several exemplary, non-limiting applications are discussed below.

The systems and methods disclosed herein have utility in the field of biology, as the disclosed systems and methods can be used to characterize samples ranging from individual cells (e.g., plant cells, animal cells), to tissue slices (e.g., biopsies), to small organisms (e.g., protozoa, bacteria, fungi, embryos, nematodes, insects). Importantly, by avoiding the use of cytotoxic stains, the disclosed systems and methods allow the same samples to be imaged repeatedly over a multi-day or even multi-week time course. Images of the samples are captured using transmitted light microscopy, and a trained system utilizes morphological characteristics (e.g., cell volume, diameter, shape, and topography) to identify cells that possess a certain cellular state. For instance, one can estimate the numbers or concentrations of particular cell types present in a sample by training a system to distinguish cells by type, or assess cell viability by training a system to distinguish between live and dead cells. Trained systems may also be used to characterize cells based on behaviors such as proliferation, differentiation, apoptosis, necrosis, motility, migration, cytoskeletal dynamics, cell-cell and cell-matrix adhesion, signaling, polarity, and vesicle trafficking. For example, the systems and methods disclosed herein may be used to differentiate between different modes of cell death based on their unique morphologies (e.g., shrinkage in apoptosis versus swelling in necrosis). These systems and methods may also be used to monitor the response of cells to any experimental manipulation, ranging from a culture condition to the effect of the outer space environment on biological processes. Thus, the disclosed systems and methods provide a means to investigate myriad aspects of biology using a highly efficient platform. While the cells, tissues, or organisms may be left untreated (e.g., not subject to staining, fixing, etc.), the systems and methods disclosed herein are also useful to image stained, fixed, or otherwise treated samples. By way of example but not by way of limitation, tissues or cells that are immunohistochemically stained, hematoxylin and eosin stained, etc. may be imaged pursuant to the systems and methods disclosed herein.

The systems and methods of the present disclosure are useful in the development of novel and improved therapeutics. For instance, the disclosed systems and methods may be used to monitor the response of cells to potential drugs in high-throughput drug screens, as described in the Examples. Additionally, the disclosed systems and methods may be used to monitor the differentiation status of cells, both in the context of development and in the directed differentiation of stem cells. Stem cells may be used to repair tissues damaged by disease or injury, either by directly injecting them into a patient or by differentiating them into replacement cells ex vivo. For example, stem cells may be differentiated into a particular blood cell type for use in donor-free blood transfusions. Other promising stem cell-based therapies include the replacement of: bone marrow cells in blood cancer patients; neurons damaged by spinal cord injuries, stroke, Alzheimer's disease, or Parkinson's disease; cartilage damaged by arthritis; skin damaged by serious burns; and islet cells destroyed by type 1 diabetes. Stem cells can also be used to generate specific cell types, tissues, 3D tissue models, or organoids for use in drug screening. Use of a trained system capable of monitoring cell differentiation status would allow for more efficient production of any of these stem cell-based products.

The systems and methods of the present disclosure are useful in the diagnosis of medical conditions. For example, the systems and methods disclosed herein can be used to quickly, efficiently, and accurately detect the presence of particular cell types in a patient sample that are indicative of a disease or condition, e.g., tumor cells, blood in urine or stool, clue cells in vaginal discharge, or inflammatory cell infiltration. For example, a system trained on images of tissue samples (e.g., biopsies) will detect morphological features that can be used to distinguish between benign, non-invasive, and invasive cancer cells. Additionally, such systems may be used to identify microbes and parasites in a patient samples, enabling the diagnosis of a wide range of infectious diseases including those caused by bacteria (e.g., tuberculosis, urinary tract infection, tetanus, Lyme disease, gonorrhea, syphilis), fungi (e.g., thrush, yeast infections, ringworm), and parasites (e.g., malaria, sleeping sickness, hookworm disease, scabies). Such methods may be particularly useful for identifying the responsible pathogen in cases where a condition may be caused by a variety of microbes (e.g., infectious keratitis of the cornea).

The systems and methods disclosed herein can be used to identify organisms in environmental samples, such as soil, crops, and water. This application could be utilized in both the environmental sciences, e.g., for assessing the health of an ecosystem based on the number and diversity of organisms, and in epidemiology, e.g., for tracing the spread of contaminants that pose a health risk.

The systems and methods disclosed herein can be used to evaluate of a wide variety materials, such as clays, fats, oils, soaps, paints, pigments, foods, drugs, glass, latex, polymer blends, textiles and other fibers, chemical compounds, crystals, rocks and minerals. Applications in which such materials are analyzed using microscopy are found across diverse fields. In industry, the systems and methods disclosed herein can be used in failure analysis, design validation, and quality control of commercial products and building materials. For example, the systems and methods disclosed herein can be used to detect defects or fractures in parts of machinery that require a high degree of precision, such as watches and aircraft engines. In computer science, the systems and methods disclosed herein can be used to examine integrated circuits and semiconductors. In both archeology and forensics, the systems and methods disclosed herein can be used to identify unknown materials and examine wear patterns on artifacts/evidence. In geology, the systems and methods disclosed herein can be used to determine the composition of rocks and minerals, and to uncover evidence as to how they were formed. In agriculture, the systems and methods disclosed herein can be used to detect microbial indicators of soil health and to inspect seeds and grains to assess their purity, quality, and germination capacity. In food science, the systems and methods disclosed herein can be used to produce in vitro cultured meat from animal cells.

The present application provides a non-limiting exemplary system that uses brightfield images as input in a screen for cancer drugs. Typically, drug response is measured via cell viability assays using live/dead fluorescent stains, which have multiple drawbacks, which are discussed above. While the use of brightfield microscopy largely avoids these issues, visualizing and quantifying live/dead cells from brightfield images alone is not easily accessible and is a significant obstacle towards more cost-efficient high-throughput screening of tumor organoids. Certain systems and methods described herein provide artificial fluorescent images that can be generated using only brightfield images.

In some embodiments, a method of generating an artificial image of a cellular composition such as a cell or a group of cells (e.g., cells in culture), is provided. In some embodiments, the generated image is indicative of whether the cell comprises one or more characteristics indicative of a particular cell state or cell identity (e.g., death, disease, differentiation, strain of bacteria, etc.). In some embodiments, the methods include receiving a brightfield image; providing the brightfield image to a trained model; receiving the artificial fluorescent image from the trained model; and outputting the artificial fluorescent image to at least one of a memory or a display. In some embodiments, the cell is a mammalian cell, a plant cell, a eukaryotic cell, or a bacterial cell. In some embodiments, the characteristic(s) indicative of a cell state or cell identity comprise one or more distinguishing physical, structural features of the cell, wherein the features are identifiable by brightfield microscopy. Exemplary, non-limiting features include size, morphology, structures within the cell, staining values, structures on the cell surface, etc.

Drug Screening

Analysis of drug response data by target may identify important pathways/mutations. For example, drugs can be applied to organoids and/or specimens, and the results of the drug application can be analyzed. For drugs that cause cell death in organoids, the targets of those drugs may be important. Thus, it is desirable to discover and/or develop additional drugs that modulate these targets. The cellular pathways and/or mutations that are important may be specific to the cancer type of the organoid. For example, if CDK inhibitors specifically kill colorectal cancer (CRC) tumor organoid cells, CDK may be especially important in CRC.

FIG. 1 shows an example of a system 100 for automatically analyzing tumor organoid images. In some embodiments, the system 100 can include a computing device 104, a secondary computing device 108, and/or a display 116. In some embodiments, the system 100 can include an organoid image database 120, a training data database 124, and/or a trained models database 128. In some embodiments, the trained models database 128 can include one or more trained machine learning models such as artificial neural networks. In some embodiments, the computing device 104 can be in communication with the secondary computing device 108, the display 116, the organoid image database 120, the training data database 124, and/or the trained models database 128 over a communication network 112. As shown in FIG. 1, the computing device 104 can receive tumor organoid images, such as brightfield images of tumor organoids, and generate artificial fluorescent stain images of the tumor organoids. In some embodiments, the computing device 104 can execute at least a portion of an organoid image analysis application 132 to automatically generate the artificial fluorescent stain images.

The organoid image analysis application 132 can be included in the secondary computing device 108 that can be included in the system 100 and/or on the computing device 104. The computing device 104 can be in communication with the secondary computing device 108. The computing device 104 and/or the secondary computing device 108 may also be in communication with a display 116 that can be included in the system 100 over the communication network 112.

The communication network 112 can facilitate communication between the computing device 104 and the secondary computing device 108. In some embodiments, communication network 112 can be any suitable communication network or combination of communication networks. For example, communication network 112 can include a Wi-Fi network (which can include one or more wireless routers, one or more switches, etc.), a peer-to-peer network (e.g., a Bluetooth network), a cellular network (e.g., a 3G network, a 4G network, a 5G network, etc., complying with any suitable standard, such as CDMA, GSM, LTE, LTE Advanced, WiMAX, etc.), a wired network, etc. In some embodiments, communication network 112 can be a local area network, a wide area network, a public network (e.g., the Internet), a private or semi-private network (e.g., a corporate or university intranet), any other suitable type of network, or any suitable combination of networks. Communications links shown in FIG. 1 can each be any suitable communications link or combination of communications links, such as wired links, fiber optic links, Wi-Fi links, Bluetooth links, cellular links, etc.

The organoid image database 120 can include a number of raw tumor organoid images, such as brightfield images. In some embodiments, the brightfield images can be generated using a brightfield microscopy imaging modality. Exemplary brightfield images are described below. In some embodiments, the organoid image database 120 can include artificial fluorescent stain images generated by the organoid image analysis application 132.

The training data database 124 can include a number of images for training a model to generate artificial fluorescent stain images. In some embodiments, the training data image database 124 can include raw brightfield images and corresponding three channel fluorescent stain images. The trained models database 128 can include a number of trained models that can receive raw brightfield images of tumor organoids and output artificial fluorescent stain images. In some embodiments, trained models 136 can be stored in the computing device 104. In some embodiments, each pair of the raw brightfield images and the corresponding three channel fluorescent stain images can be include a common field of view of the same slide captured by different microscope settings for the brightfield images and the corresponding three channel fluorescent stain images, respectively (e.g., brightfield settings and fluorescent settings).

In some embodiments, the training data database 124 can include paired (corresponding) histopathology slide images, where each image depicts a tissue slice from a biological specimen or a blood smear from a blood draw. In some embodiments, if two images correspond it can indicate that the tissue slice(s) or blood smear(s) associated with the two images are obtained from the same biological specimen. For example, the two images may be obtained from the same tumor biopsy or the same blood draw. In some embodiments, the images can depict tissue slices that may have been approximately adjacent in the specimen and/or the same tissue slice may have been used to generate both images. In some embodiments, the corresponding images can depict corresponding cellular and/or tissue structures. For example, both images can depict common structures (e.g., different sections of the same biological cell, same organ, same tissue, etc.). In one example, one of the images can include hematoxylin and eosin (H&E) staining and the other image can include immunohistochemistry (IHC) staining. The IHC staining may be multiplex IHC staining. An example of corresponding images can be found in U.S. patent application Ser. No. 16/830,186, filed Mar. 25, 2020 and titled "Determining Biomarkers From Histopathology Slide Images," which is incorporated herein by reference in its entirety. In various embodiments, one advantage of simulating IHC slides is to facilitate the detection of various biomarkers without the cost of IHC staining.

Figure 2:
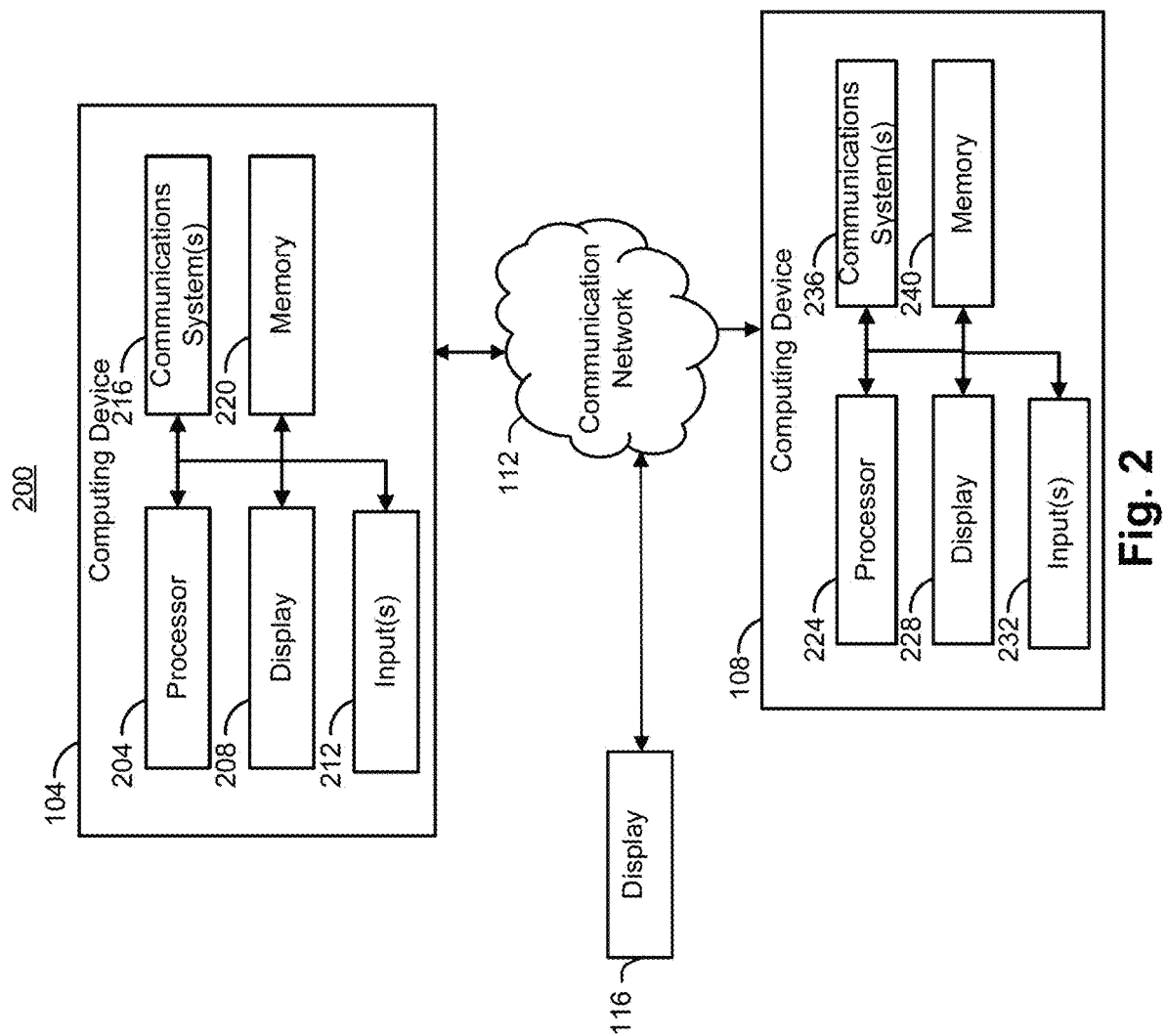
FIG. 2 shows an example of hardware that can be used in some embodiments of the system.

FIG. 2 shows an example 200 of hardware that can be used in some embodiments of the system 100. The computing device 104 can include a processor 204, a display 208, an input 212, a communication system 216, and a memory 220. The processor 204 can be any suitable hardware processor or combination of processors, such as a central processing unit ("CPU"), a graphics processing unit ("GPU"), etc., which can execute a program, which can include the processes described below.

In some embodiments, the display 208 can present a graphical user interface. In some embodiments, the display 208 can be implemented using any suitable display devices, such as a computer monitor, a touchscreen, a television, etc. In some embodiments, the inputs 212 of the computing device 104 can include indicators, sensors, actuatable buttons, a keyboard, a mouse, a graphical user interface, a touch-screen display, etc.

In some embodiments, the communication system 216 can include any suitable hardware, firmware, and/or software for communicating with the other systems, over any suitable communication networks. For example, the communication system 216 can include one or more transceivers, one or more communication chips and/or chip sets, etc. In a more particular example, communication system 216 can include hardware, firmware, and/or software that can be used to establish a coaxial connection, a fiber optic connection, an Ethernet connection, a USB connection, a Wi-Fi connection, a Bluetooth connection, a cellular connection, etc. In some embodiments, the communication system 216 allows the computing device 104 to communicate with the secondary computing device 108.

In some embodiments, the memory 220 can include any suitable storage device or devices that can be used to store instructions, values, etc., that can be used, for example, by the processor 204 to present content using display 208, to communicate with the secondary computing device 108 via communications system(s) 216, etc. The memory 220 can include any suitable volatile memory, non-volatile memory, storage, or any suitable combination thereof. For example, the memory 220 can include RAM, ROM, EEPROM, one or more flash drives, one or more hard disks, one or more solid state drives, one or more optical drives, etc. In some embodiments, the memory 220 can have encoded thereon a computer program for controlling operation of computing device 104 (or secondary computing device 108). In such embodiments, the processor 204 can execute at least a portion of the computer program to present content (e.g., user interfaces, images, graphics, tables, reports, etc.), receive content from the secondary computing device 108, transmit information to the secondary computing device 108, etc.

The secondary computing device 108 can include a processor 224, a display 228, an input 232, a communication system 236, and a memory 240. The processor 224 can be any suitable hardware processor or combination of processors, such as a central processing unit ("CPU"), a graphics processing unit ("GPU"), etc., which can execute a program, which can include the processes described below.

In some embodiments, the display 228 can present a graphical user interface. In some embodiments, the display 228 can be implemented using any suitable display devices, such as a computer monitor, a touchscreen, a television, etc. In some embodiments, the inputs 232 of the secondary computing device 108 can include indicators, sensors, actuatable buttons, a keyboard, a mouse, a graphical user interface, a touch-screen display, etc.

In some embodiments, the communication system 236 can include any suitable hardware, firmware, and/or software for communicating with the other systems, over any suitable communication networks. For example, the communication system 236 can include one or more transceivers, one or more communication chips and/or chip sets, etc. In a more particular example, communication system 236 can include hardware, firmware, and/or software that can be used to establish a coaxial connection, a fiber optic connection, an Ethernet connection, a USB connection, a Wi-Fi connection, a Bluetooth connection, a cellular connection, etc. In some embodiments, the communication system 236 allows the secondary computing device 108 to communicate with the computing device 104.

In some embodiments, the memory 240 can include any suitable storage device or devices that can be used to store instructions, values, etc., that can be used, for example, by the processor 224 to present content using display 228, to communicate with the computing device 104 via communications system(s) 236, etc. The memory 240 can include any suitable volatile memory, non-volatile memory, storage, or any suitable combination thereof. For example, the memory 240 can include RAM, ROM, EEPROM, one or more flash drives, one or more hard disks, one or more solid state drives, one or more optical drives, etc. In some embodiments, the memory 240 can have encoded thereon a computer program for controlling operation of secondary computing device 108 (or computing device 104). In such embodiments, the processor 224 can execute at least a portion of the computer program to present content (e.g., user interfaces, images, graphics, tables, reports, etc.), receive content from the computing device 104, transmit information to the computing device 104, etc.

The display 116 can be a computer display, a television monitor, a projector, or other suitable displays.

Figure 3:
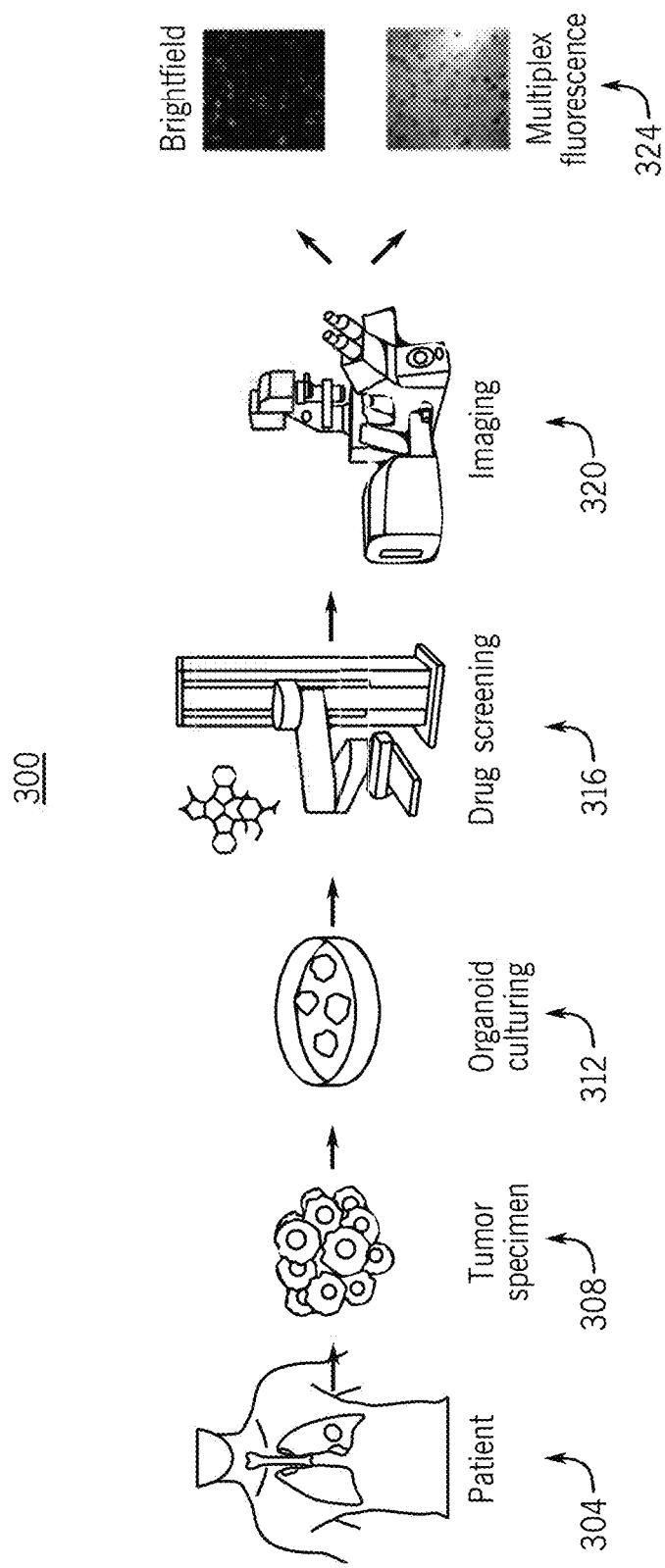
FIG. 3 shows an exemplary flow that can generate brightfield images and/or fluorescent images, as well as live/dead assays readouts, using patient derived organoids grown from tumor specimens.

FIG. 3 shows an exemplary flow 300 that can generate brightfield images and/or fluorescent images, as well as live/dead assays readouts, using patient derived organoids grown from tumor specimens. In some embodiments, the live/dead assays readouts can be produced using brightfield and multiplexed fluorescence imaging. Drug response can be measured via cell viability assays using live/dead fluorescent stains. In some embodiments, the flow 300 can be included in a high throughput drug screening system. An example of a high throughput drug screening can be found in U.S. Prov. patent application Ser. No. 17/114,386, titled "Large Scale Organoid Analysis" and filed Dec. 7, 2020, which is incorporated herein by reference in its entirety. In some examples, biological therapies, such as antibodies or allogenic therapies, may be used as one or more of the drugs in the drug screening.

The flow 300 can include harvesting a tumor specimen 308 from a human patient 304, culturing organoids 312 using the tumor specimen 308, drug screening 316 the organoids, imaging the organoids 320, and outputting brightfield and fluorescence images 324 of the organoids. After the organoids are cultured, cells from the organoids can be plated into an assay plate (e.g. a 96-well assay plate, a 384-well assay plate, etc.). The assay plate may also be referred to as a plate. The drug screening 316 can include plating the cells and treating the cells with a number of different drugs and/or concentrations. For example, a 384-well plate can include fourteen drugs at seven different concentrations. As another example, a 96-well plate can include six drugs at five different concentrations. The imaging 320 can include brightfield imaging the treated cells, as well as applying fluorescent stains to at least a portion of the cells and fluorescent imaging the cells. In some embodiments, the fluorescent imaging can include producing three channels of data for each cell. The three channels of data can include a blue/all nuclei channel, a green/apoptotic channel, and a red/pink/dead channel. Each channel can be used to form a fluorescent image. Additionally, the imaging 320 can produce combined 3-channel fluorescent images that include the blue/all nuclei channel, the green/apoptotic channel, and the red/pink/dead channel. In some embodiments, the imaging 320 can include generating brightfield images of the cells using a bright-field microscope and generating fluorescent images of the cells using a confocal microscope such as a confocal laser scanning microscope. In some embodiments, instead of using traditional fluorescent staining to generate the fluorescent images, the imaging 320 can include generating brightfield images for at least a portion of the cells and generating artificial brightfield images for the portion of the cells based on the brightfield images using a process described below (e.g., the process of FIG. 9).

By way of example but not by way of limitation, in some embodiments, brightfield images (for example a 2D brightfield projection) depicting a cell culture well during a drug screening assay can be generated using a brightfield modality, such as a brightfield microscope. In some embodiments, a brightfield image is generated using a 10× objective on a microscope. A different objective can be used if higher or lower magnification is desired. In some embodiments, the microscope can be an ImageXPRESS microscope available from Molecular Devices. Other microscope brands capable of brightfield imaging are commercially available and can also be employed in the disclosed methods. In some embodiments, the cells can be cancer cell lines or cancer tumor organoids derived from patient specimens.

FIG. 4 shows an exemplary flow 400 for training a generator 408 to generate an artificial fluorescent image 412 based on an input brightfield image 404 of a cellular composition, such as organoid cells. In some embodiments, the generator 408 can include a U-Net convolutional neural network. In some embodiments, the generator 408 can include a pix2pix model. In some embodiments, the generator 408 can be a generative adversarial network (GAN). An exemplary neural network that can be included in the generator 408 is described below in conjunction with FIG. 6. In some embodiments, the generator can include a neural network that can receive the brightfield image 404 and output a single three-channel fluorescent image (e.g., a 256×256×3 image). In some embodiments, the generator can include three neural networks that can each receive the brightfield image 404 and output a one-channel fluorescent image (e.g., a 256×256×1 image). Generators that include three neural networks that can each receive the brightfield image 404 and output a one-channel fluorescent image may be referred to as three-model generators. Each of the neural networks can be trained to output a specific channel of fluorescence. For example, a first neural network can output a blue/all nuclei channel image, a second neural network can output a green/apoptotic channel image, and a third neural network can output a red/dead channel image. The flow 400 can include combining the blue/all nuclei channel image, the green/apoptotic channel image, and the red/dead channel image into a single three-channel fluorescent image (e.g., a 256×256×3 image, a 1024×1024×3 image, etc.).

The flow can include providing the brightfield image 404, the artificial fluorescent image 412, and a ground truth fluorescent image 424 associated with brightfield image to a discriminator 416 that can predict whether or not an image is real or generated by the generator 408 (e.g., the artificial fluorescent image 412). In some embodiments, the generator 408 can receive an image and output a label ranging from 0 to 1, with 0 indicating that image is generated by the generator 408 and 1 indicating that the image is real (e.g., the ground truth fluorescent image 424 associated with the brightfield image 404). In some embodiments, the discriminator 416 can be a PatchGAN discriminator, such as a 1×1 PatchGAN discriminator. An exemplary discriminator is described below in conjunction with FIG. 7.

The flow 400 can include an objective function value calculation 420. The objective function value calculation 420 can include calculating an objective function value based on labels output by the discriminator 416 and/or by other metrics calculated based on the brightfield image 404, the artificial fluorescent image 412, and the ground truth fluorescent image 424. The objective function value can capture multiple loss functions (e.g., a weighted sum of multiple loss functions). In this way, the objective function value can act as a total loss value for the generator 408 and the discriminator 416. The flow 400 can include transmitting the objective function value and/or other information from the discriminator 416 to the generator 408 and the discriminator 416 in order to update both the generator 408 and the discriminator 416. A number of different suitable objective functions can be used to calculate the objective function value. However, in testing an embodiment of the generator 408, a sum of GANLoss+0.83SSIM+0.17L1 was shown to outperform other tested loss functions such as GANLoss+L1 as used by the generator 408. GANLoss can be used to determine whether an image is real or generated. The L1 loss can be used as an additional objective to be minimized to ensure that the generated and real image have the least mean absolute error in addition to GANLoss. Structural Similarity Index (SSIM) can be used to improve performance across multiple performance metrics as well as reduce artifacts. The objective function value calculation 420 will be described below.

The flow 400 can include receiving a number of pairs of a brightfield image and a corresponding ground truth fluorescence image, and iteratively training the generator 408 using each pair of images.

In some embodiments, the flow 400 can include receiving a number of pairs of a H&E image and a corresponding ground truth IHC image, and iteratively training the generator 408 using each pair of images to generate artificial IHC images.

In some embodiments, the flow 400 can include receiving a number of pairs of an IHC image and a corresponding ground truth H&E image, and iteratively training the generator 408 using each pair of images to generate artificial H&E images.

In some embodiments, the flow 400 can include receiving a number of pairs of an IHC image and/or a multiplex IHC images and a corresponding ground truth H&E image, and iteratively training the generator 408 using each pair of images to generate artificial H&E images.

In some embodiments, the flow 400 can include preprocessing the brightfield image 404 and the ground truth fluorescent image 424. Raw brightfield and fluorescent images may have minimal contrast and require enhancement before being used to train the generator 408. For example, in testing, the pixel intensities for the individual channels of the fluorescent image were generally skewed to zero, which may have been because most of the image is black (i.e., background), except for regions containing organoids and/or cells.

In some embodiments, the artificial fluorescent image 412 can be used to provide a count of live/dead cells. In order to enhance the contrast of the artificial fluorescent image 412 and improve the ability to count live/dead cells from the artificial fluorescent image 412, both the brightfield image 404 and the corresponding ground truth image 424 can undergo contrast enhancement to brighten and sharpen organoids/cells.

In some embodiments, multiple brightfield images and multiple ground truth fluorescent images can be generated per well. For example, for a 96-well plate, there can be about 9-16 sites per well that get imaged.

In some embodiments, the raw brightfield and ground truth fluorescent images can have pixel intensities ranging from $[0, 2^{16}]$. First, a contrast enhancement process, which can be included in the organoid image analysis application 132, can convert each image to an unsigned byte format, with values ranging from [0, 255]. Next, the contrast enhancement process can stretch and clip each pixel intensity to a desired output range.

In some embodiments, the desired intensity range of an input image to be stretched can be decided on a per image basis as follows: For the three pixel intensities corresponding to the three fluorophores used to generate the fluorescent image, the input range can be re-scaled using the mode of the pixel intensity distribution as the lower bound value and 1/10th the maximum pixel intensity as the upper bound. The contrast enhancement process can choose the upper bound in order to avoid oversaturated pixels and focus on cell signal. The contrast enhancement process can normalize each pixel intensity based on the lower bound and the upper bound, which function as a min/max range, using a min-max norm, and then each pixel can be multiplied by the output range [0,255]. For the brightfield image 404, the contrast enhancement process can determine an input range by uniformly stretching the 2nd and 98th percentile of pixel intensities to the output range [0,255].

For images with low signal, background noise may be included in the output range. To minimize any remaining back-ground noise, the contrast enhancement process can clip the minimum pixel value by two integer values for the red and green channels, and by three integer values for the blue channel, where the intensity range is wider on average. The maximum pixel values can be increased accordingly to preserve intensity range per image.

In some embodiments, the ground truth image 424 can be a 1024×1024×3 RGB image including a blue channel corresponding to nuclei (Hoecsht), a green channel corresponding to apoptotic cells (Caspase), and a red channel corresponding to dead cells (TO-PRO-3) In some embodiments, the flow 400 can include enhancing the ground truth image 424. In some embodiments, the enhancing can include contrast enhancing the blue channel, the green channel, and the red channel to brighten and sharpen organoids and/or cells in the ground truth image 424. In some embodiments, the flow can down convert pixel intensities in the ground truth image 424 (e.g., converting sixteen bit pixel intensities to eight bit intensities). After converting pixel intensities, the flow 400 can include rescaling pixel intensities to 1/10th of a maximum pixel intensity as the upper bound, as well as to the mode of the pixel intensity+two integer values as the lower bound for the red channel and the green channel, and to the mode of the pixel intensity+three integer values for the blue channel as the lower bound.

In some embodiments, the discriminator 416 can output a predicted label (e.g., a "0" or a "1") to the objective function calculation 420. The predicted label can indicate if the artificial fluorescent image 412 is fake or real. In some embodiments, the objective function can be calculated as a weighted sum of GANLoss, SSIM, and L1. In some embodiments, the GANLoss can be calculated based on the predicted label output by the discriminator. The GANLoss can be used to determine whether the artificial fluorescent image 412 is real or generated. In some embodiments, the L1 loss can be calculated based on the artificial fluorescent image 412 and the corresponding ground truth image. The L1 loss can be used as an additional objective to be minimized to ensure that the artificial fluorescent image 412 and the corresponding ground truth image have the least mean absolute error in addition to GANLoss.

Certain machine learning models, such as the pix2pix model, may only use GANLoss and L1 loss in training a generator. As mentioned above, the objective function calculation 420 can include an SSIM metric in addition to the GANLoss and the L1 loss, which can improve the performance of the generator 408 in comparison to a generator trained using only GANLoss and L1 loss.

In some embodiments, the objective function implemented in the objective function calculation can be defined as:

$$G^* = \underset{G}{\arg\min}\underset{D}{\max} \mathcal{L}_{GAN}(G, D) + \lambda \mathcal{L}_{L1}(G) + \beta(1 - \mathcal{L}_{SSIM}(G)) \quad (1)$$

where $\lambda + \beta = 1$, $L_{L1}$ is the mean absolute error loss, and $1 - L_{SSIM}(G)$ is the structural similarity index loss between the generated image G (e.g., the fluorescent image 412) and the corresponding ground truth image. In some embodiments, $\lambda$ can be 0.17 and $\beta$ can be 0.83. In some embodiments, $\lambda$ can be selected from 0.1 to 0.3, and $\beta$ can be selected from 0.7 to 0.9.

In some embodiments, SSIM can take into account the luminance (l), contrast (c), and structure (s) of two images and computes a metric between 0 and 1, where 1 indicates a perfect match between the two images:

$$l(x, y) = \frac{2\mu_x \mu_y + C_1}{\mu_x^2 + \mu_y^2 + C_1} \quad (2)$$

$$c(x, y) = \frac{2\sigma_x \sigma_y + C_2}{\sigma_x^2 + \sigma_y^2 + C_2} \quad (3)$$

$$s(x, y) = \frac{\sigma_{xy} + C_3}{\sigma_x \sigma_y + C_3} \quad (4)$$

$C_1$, $C_2$ and $C_3$ are small constants defined by:

$$C_1 = (K_1 L)^2, C_2 = (K_2 L)^2 \text{ and } C_3 = C_2/2 \quad (5)$$

where $K_1$, $K_2$ are two scalar constants whose values are less than 1, and L is the dynamic range of the pixel intensities (i.e. 256). SSIM can then be calculated as:

$$SSIM(x, y) = [l(x, y)]^\alpha \cdot [c(x, y)]^\beta \cdot [s(x, y)]^\gamma \quad (6)$$

$$SSIM(x, y) = \frac{(2\mu_x \mu_y + C_1)(2\sigma_{xy} + C_2)}{(\mu_x^2 + \mu_u^2 + C_1)(\sigma_x^2 + \sigma_u^2 + C2)} \quad (7)$$

where l, c, and s are computed using the mean, variance and covariance respectively of two images of the same size using a fixed window size. $\alpha$, $\beta$, and $\gamma$ are constants set to 1. In addition to structural similarity, we also evaluated model prediction using root mean square error, which is the sum of the squared difference of pixel intensities.

In some embodiments, the Proposed Loss function can be as follows:

DiscriminatorLoss=MSELoss{Real Prediction,1}+
    MSELoss{Generated Prediction,0}+
    MSELoss{Predicted Viability,Viability}

GeneratorLoss=MSELoss{Generated Prediction,1}+
    MAE{Generated Fluorescent, Real Fluorescent}+SSIM{Generated Fluorescent,Real Fluorescent};

where MSE refers to Mean Squared Error Loss, MAE is the mean absolute error, and SSIM is the Structural similarity index. The RCA Model was trained for thirty epochs with a learning rate of 2e-3 and Adam optimizer. The images of resolution 1024×1024 were imaged at 10× magnification. They were randomly flipped as a data augmentation step.

In some embodiments, once a dye is added to a cell culture well, the cells in that well cannot continue to be used for the experiment, such that it is difficult or impossible to measure cell death in that well at a subsequent point in time. In some embodiments, the flow 400 can include generating artificial fluorescent images, which can reduce time requirements for imaging by a factor of ten in comparison to utilizing dyes to generate the fluorescent images. Standard fluorescent imaging may take up to an hour to perform. In some embodiments, the flow 400 can be used in conjunction with a drug screening platform that uniquely interprets tumor organoids (TOs) which have limited biomass and intra-tumoral clonal heterogeneity by incorporating Patient Derived Tumor Organoids. The platform couples high content fluorescent confocal imaging analysis with a robust statistical analytical approach to measure hundreds of discrete data points of TO viability from as few as 10^3 cells.

In some embodiments, a flow similar to flow 400 may be used to train a generator (e.g., the generator 408) to receive H&E images and generate artificial IHC images and/or multiplex IHC images. In some embodiments, the flow 400 can include receiving an H&E image from training data database 124 and providing the H&E image to the generator 408 (in place of the brightfield image 404). In these embodiments, the discriminator 424 can receive an artificial H&E image generated by the generator and a ground truth IHC image (in place of the ground truth fluorescent image 424) corresponding to an H&E image from training data database 124. Thus, the flow 400 can be used to train a generator to generate artificial IHC images and/or multiplex IHC images based on H&E images.

Referring to FIG. 4 as well as FIG. 5, an exemplary flow 500 for generating an artificial fluorescent image 512 is shown. The flow 500 can include providing an input brightfield image 504 of plated cells to a trained model 508. The trained model 508 can include the generator 408, which can be trained using the flow 400. The trained model 508 can output an artificial fluorescent image 512. The fluorescent image 512 can be used to generate a live/dead assays readout and/or analyze the effectiveness of different drugs and/or dosages on cancer cells in tissue organoids.

Notably, the flow 500 can produce the fluorescent image 512 without the use of fluorescent dyes, which provides several advantages over traditional fluorescent imaging processes that require the use of fluorescent dyes. Some dyes have cytotoxicity and must be added a certain amount of time before imaging. Additionally, once certain dyes are added to a cell culture well, the cells in that well cannot continue to be used for reimaging because of the difficulty in measuring cell death in that well at a subsequent point in time. Thus, the flow 500 can improve the ease of generating the fluorescent images because the flow 500 may only require brightfield imaging, which is not time-dependent like the traditional fluorescent imaging. Additionally, the flow 500 can increase the speed at which the fluorescent images are obtained, because fluorescent dyes do not need to be applied to the cells, and because the flow 500 does not have to wait for the fluorescent dyes to diffuse before imaging the cells. As another example, the flow 500 can allow multiple fluorescent images to be generated for each cell well at a number of different time points. The fluorescent dyes used in traditional fluorescent imaging can damage the cells enough to prevent reimaging. In contrast, the flow 500 can be used to produce multiple fluorescent images over a time period of days, weeks, months, etc. Thus, the flow 500 can provide more data points per cell well than traditional fluorescent imaging.

The training data used to train a trained model may be selected based on the aspects of the cellular compositions to be imaged post-training. In some embodiments, a single trained model (e.g., trained model 508) can be trained on training data including a set of brightfield images and corresponding fluorescent images associated with one of six or more organoid lines each having a distinct cancer type, such that each organoid line is represented in the training data. In some embodiments, a single trained model (e.g., trained model 508) can be a pan-cancer model trained to generate artificial fluorescent stain images from a brightfield image associated with any cancer type. In some embodiments, a trained model can be trained on training data only including images associated with one organoid line (for example, one cancer type).

Figure 6:
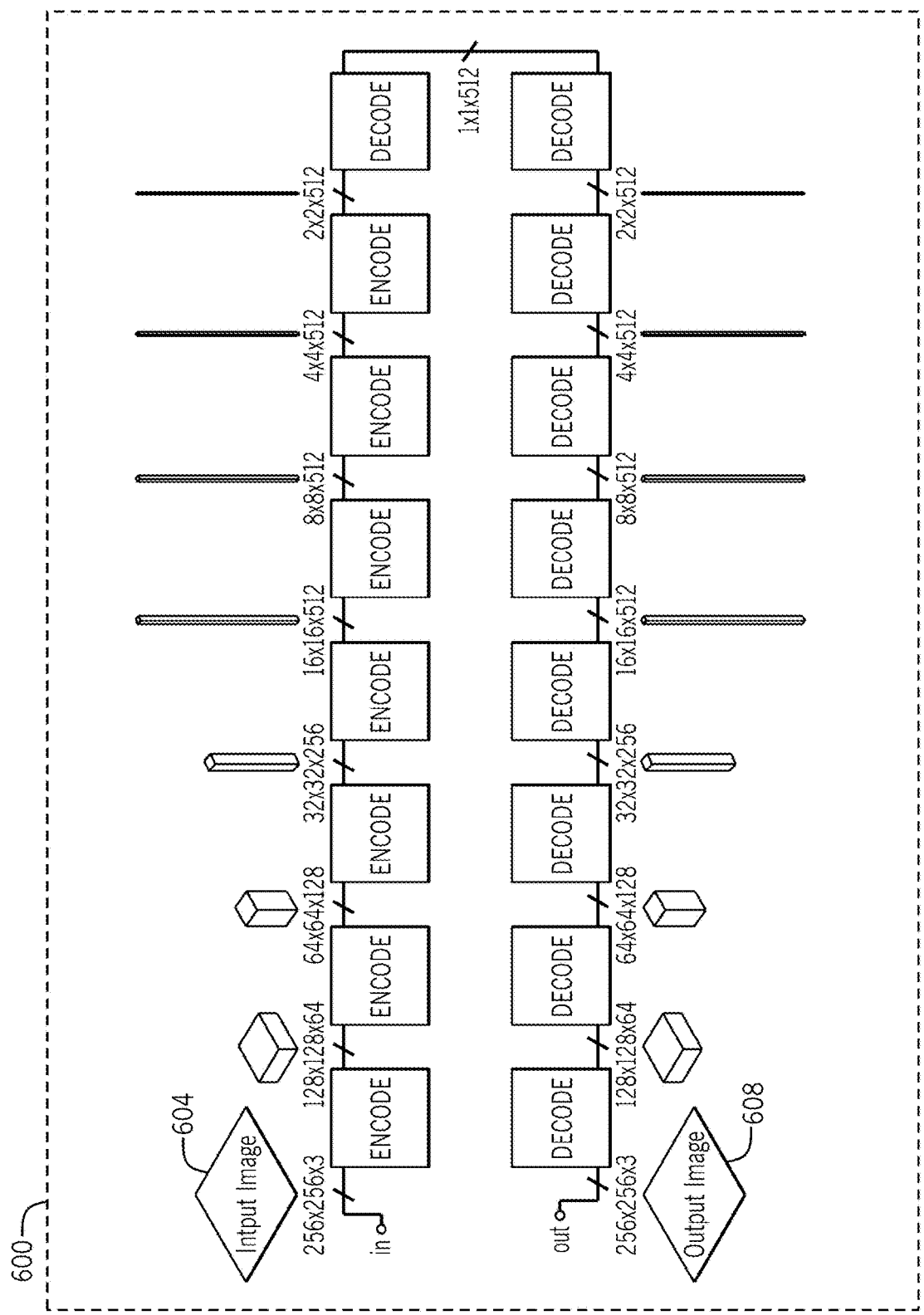
FIG. 6 shows an exemplary neural network.

FIG. 6 shows an exemplary neural network 600. The neural network 600 can be trained to receive an input image 604 and generate an artificial fluorescent image 608 based on the input image 604. In some embodiments, the input image 604 can be a raw brightfield image that has been processed to enhance contrast and/or modify other characteristics in order to enhance the raw brightfield image and potentially produce a better artificial fluorescent image (e.g., the fluorescent image 608).

In some embodiments, the neural network 600 can include a Unet architecture. In some embodiments, the Unet architecture can be sized to receive a 256×256×3 input image. The 256×256×3 input image can be a brightfield image. In some embodiments, the input image can be a 256×256×1 image. In some embodiments, the generator 408 in FIG. 4 and/or the trained model 508 in FIG. 5 can include the neural network 600.

Figure 7:
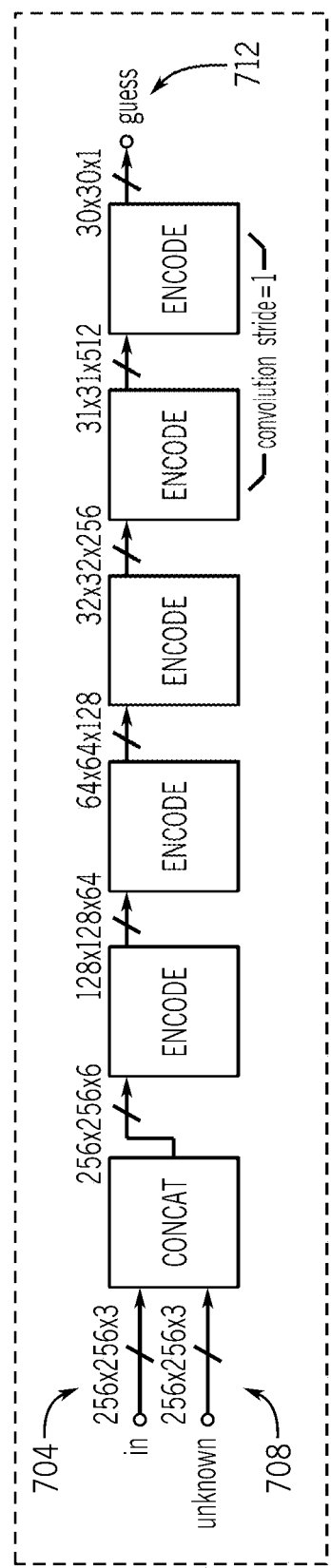
FIG. 7 shows an exemplary discriminator.

FIG. 7 shows an exemplary discriminator 700. In some embodiments, the discriminator 700 in FIG. 7 can be included as the discriminator 416 in the flow 400 shown in FIG. 4. In some embodiments, the discriminator 700 can be a 1×1 PatchGAN. In some embodiments, the discriminator 700 can receive a brightfield image 704 and a fluorescent image 708. The fluorescent image can be an artificial fluorescent image (e.g., the fluorescent image 608 in FIG. 6) or a ground truth fluorescent image. In some embodiments, each of the brightfield image 704 and the fluorescent image 708 can be 256×256×3 input images. In some embodiments, the brightfield image 704 and the fluorescent image 708 can be concatenated. In some embodiments, the concatenated image can be a 256×256×6 input image.

In some embodiments, the discriminator 700 can receive the brightfield image 704 and a fluorescent image 708 and generate a predicted label 712 indicative of whether or not the fluorescent image 708 is real or fake. In some embodiments, the predicted label 712 can be a "0" to indicate the fluorescent image 708 is fake, and "1" to indicate the fluorescent image 708 is real. In some embodiments, the discriminator 700 can include a neural network Referring to FIGS. 4-7, in some embodiments, the flow 400, the flow 500, the neural network 600, and the discriminator 700 can be implemented using Pytorch version 1.0.0. In some embodiments, the flow 400 can be used to train the generator 408 to generate artificial fluorescent images for a colon cancer organoid line. In some embodiments, the flow 400 can be used to train the generator 408 to generate artificial fluorescent images for a gastric cancer organoid line.

Figure 8:
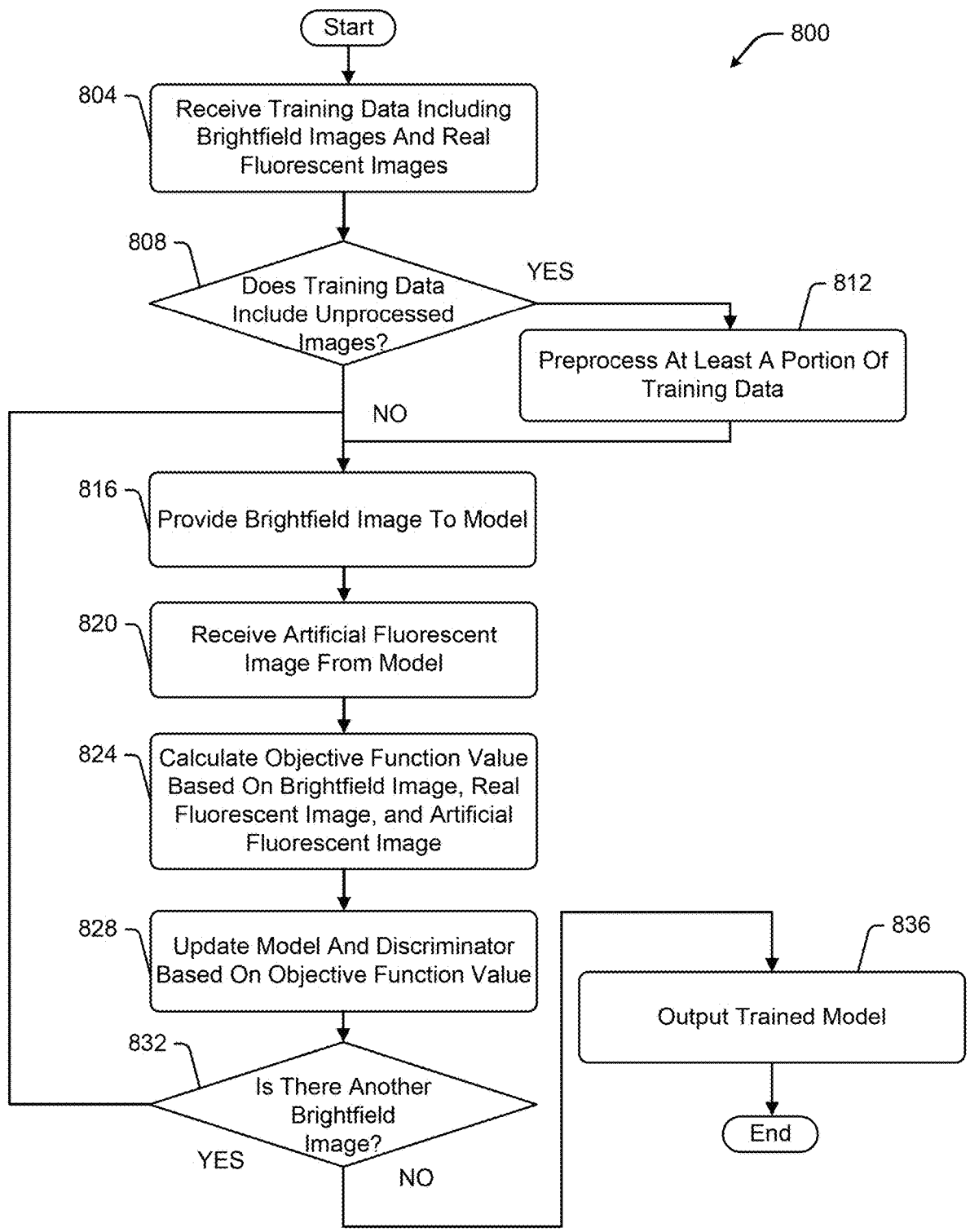
FIG. 8 shows an exemplary process that can train a model to generate an artificial fluorescent stain image of one or more organoids based on an input brightfield image.

FIG. 8 shows an exemplary process 800 that can train a model to generate an artificial fluorescent stain image of one or more organoids based on an input brightfield image. In some embodiments, the model can be the generator 408 in FIG. 4, and/or the neural network 600. In some embodiments, the model can include a neural network that can receive the input brightfield image and output a single three-channel fluorescent image (e.g., a 256×256×3 image). In some embodiments, the model can include three neural networks that can each receive the brightfield image and output a one-channel fluorescent image (e.g., a 256×256×1 image). The one-channel images can then be combined into a single three-channel fluorescent image.

In some embodiments, the process 800 can be used to train a model to output artificial fluorescent images of objects other than tumor organoids using a number of non-fluorescent images (e.g., brightfield images) and fluorescent stain images (which may have more or less than three channels) as training data.

The process 800 can be implemented as computer readable instructions on one or more memories or other non-transitory computer readable media, and executed by one or more processors in communication with the one or more memories or other media. In some embodiments, the process 800 can be implemented as computer readable instructions on the memory 220 and/or the memory 240 and executed by the processor 204 and/or the processor 224.

At 804, the process 800 can receive training data. In some embodiments, the training data can include a number of brightfield images and a number of associated real fluorescent images of organoids. In some embodiments, the organoids can be from a single tumor organoid line. In some embodiments, the brightfield images and the real fluorescent images can be preprocessed in order to enhance contrast as described above. In some embodiments, the brightfield images and the real fluorescent images can be raw images that have not undergone any preprocessing such as contrast enhancement.

At 808, if the training data includes raw brightfield images and/or raw real fluorescent images (i.e., "YES" at 808), the process 800 can proceed to 812. If the training data does not include any raw brightfield images or raw real fluorescent images (i.e., "NO" at 808), the process 800 can proceed to 816.

At 812, the process 800 can preprocess at least a portion of the brightfield images and/or real fluorescent images. In some embodiments, at 812, the process 800 can enhance the contrast of any raw brightfield images and/or real fluorescent images included in the training data. In some embodiments, the raw brightfield and ground truth fluorescent images can have pixel intensities ranging from $[0,2^{16}]$. In some embodiments, the process 800 can convert each image to an unsigned byte format, with values ranging from [0, 255]. The process 800 can then stretch and clip each pixel intensity to a desired output range.

In some embodiments, the process 800 can stretch the desired intensity range of the input on a per image basis. For the three pixel intensities corresponding to the three fluorophores used to generate a real fluorescent image, the process 800 can re-scale the input range using the mode of the pixel intensity distribution as the lower bound value and 1/10th the maximum pixel intensity as the upper bound. The process 800 can determine the upper bound in order to avoid oversaturated pixels and focus on cell signal. The process 800 can normalize each pixel intensity based on the lower bound and the upper bound, which function as a min/max range, using a min-max norm, and then each pixel can be multiplied by the output range [0,255]. For each brightfield image included in the training data, the process 800 can determine an input range by uniformly stretching the 2nd and 98th percentile of pixel intensities to the output range [0,255].

For images with low signal, background noise may be included in the output range. In some embodiments, to minimize any remaining background noise, the process 800 can clip the minimum pixel value by two integer values for the red and green channels, and by three integer values for the blue channel, where the intensity range is wider on average. In some embodiments, the process 800 can increase maximum pixel values accordingly to preserve intensity range per image.

At 816, the process 800 can provide a brightfield image to the model. As described above, in some embodiments, the model can be the generator 408 in FIG. 4 and/or the neural network 600 in FIG. 6. In some embodiments, the model can include three neural networks, and each neural network can receive a copy of the brightfield image and output a different channel (e.g., red, green, or blue) of an artificial fluorescent image.

At 820, the process 800 can receive an artificial fluorescent image from the model. The model can generate the artificial fluorescent image (e.g., the artificial fluorescent image 412) based on the brightfield image (e.g., the brightfield image 404) provided to the model. In some embodiments, the process 800 can receive three one-channel images from three neural networks included in the model and combine the one-channel images into a single three-channel artificial fluorescent image.

At 824, the process 800 can calculate an objective function value based on the brightfield image, the real fluorescent image associated with the brightfield image, and the artificial fluorescent image. In some embodiments, the process 800 can determine a predicted label indicative of whether or not the artificial fluorescent image is real or not by providing the artificial fluorescent image and the real fluorescent image to a discriminator (e.g., the discriminator 416). In some embodiments, the objective function value can be calculated using equation (1) above, where A is 0.17 and 8 is 0.83. In some embodiments, A can be selected from 0.1 to 0.3, and 8 can be selected from 0.7 to 0.9. In some embodiments, the learning rate can fixed at 0.0002 for a first number of epochs (e.g., fifteen epochs) of training, and then linearly decayed to zero over a second number of epochs (e.g., ten epochs).

At 828, the process 800 can update the model (e.g., the generator 408) and the discriminator (e.g., the discriminator 416) based on the objective function value. In some embodiments, the model and the discriminator can each include a neural network. In some embodiments, the process 800 can update weights of layers included in neural networks included in the model and the discriminator based on the objective function value.

At 832, the process 800 can determine whether or not there is a brightfield image included in the training data that has not been provided to the model. If there is a brightfield image included in the training data that has not been provided to the model (e.g., "YES" at 832), the process can proceed to 816 in order to provide the brightfield image to the model. If there are no brightfield images included in the training data that has not been provided to the model (e.g., "NO" at 832), the process can proceed to 836.

At 836, the process 800 can cause the model to be output. At 836, the model has been trained, and can be referred to as a trained model. In some embodiments, the process 800 can cause the trained model to be output to at least one of a memory (e.g., the memory 220 and/or the memory 240) and/or a database (e.g., the trained models database 128). The trained model may be accessed and used in certain processes, such as the processes in FIGS. 9 and 13. The process 800 can then end.

Figure 9:
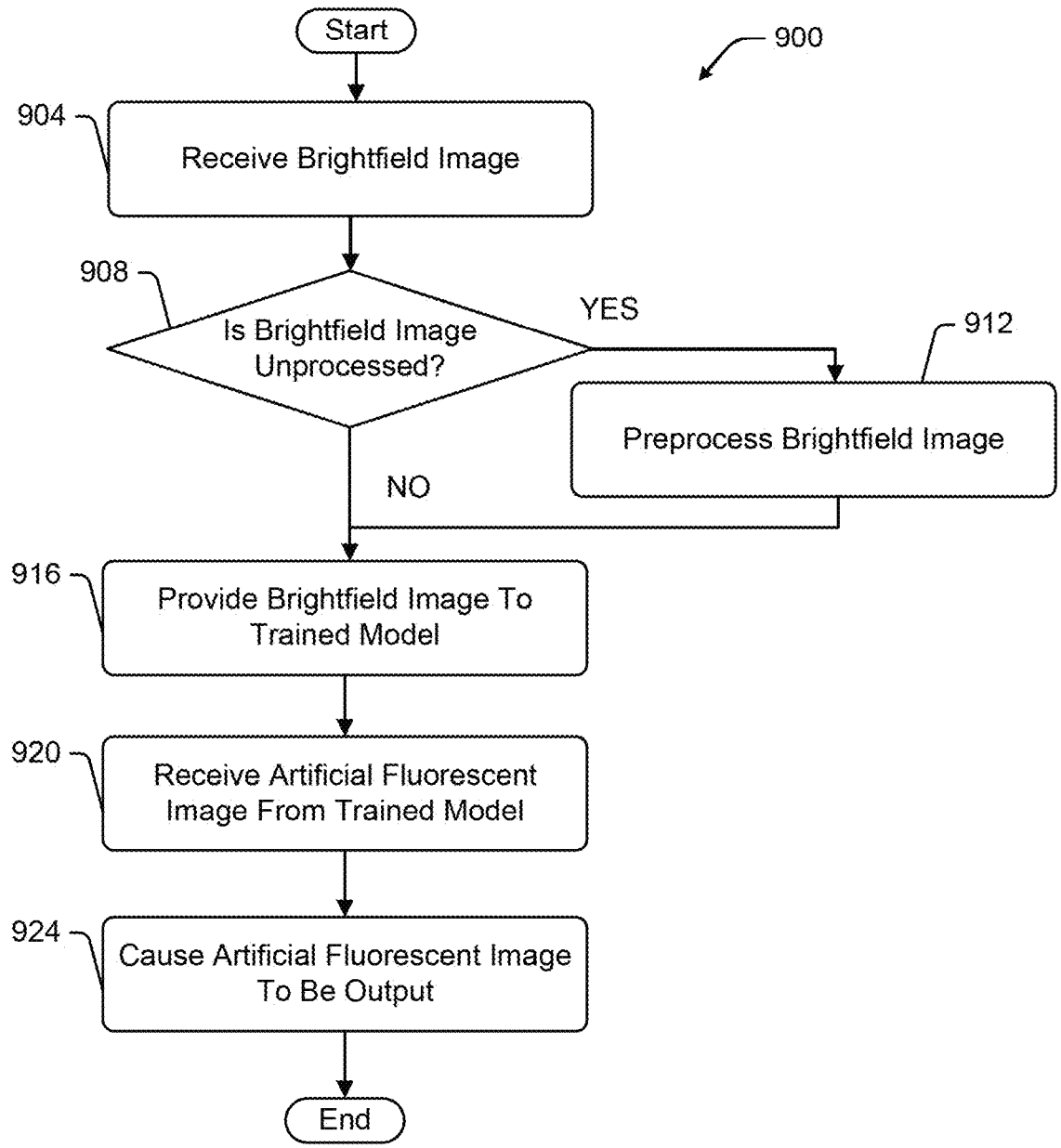
FIG. 9 shows an exemplary process that can generate an artificial fluorescent image of one or more organoids based on a brightfield image.

FIG. 9 shows an exemplary process 900 that can generate an artificial fluorescent image of one or more organoids based on a brightfield image. More specifically, the process 900 can generate the artificial fluorescent image using a trained model. In some embodiments, the model can be the generator 408 in FIG. 4, the trained model 508, and/or the neural network 600 in FIG. 6 trained using the process 800. In some embodiments, the model can include a neural network that can receive the input brightfield image and output a single three-channel fluorescent image (e.g., a 256×256×3 image). In some embodiments, the model can include three neural networks that can each receive the brightfield image and output a one-channel fluorescent image (e.g., a 256×256×1 image). The one-channel images can then be combined into a single three-channel fluorescent image.

In some embodiments, the process 900 can be used to generate artificial fluorescent images (which can have one channel, two channels, three channels, etc.) of objects other than tumor organoids using a non-fluorescent image (e.g., a brightfield image). In this way, objects other than tumor organoids that require fluorescent staining to be properly imaged can be artificially generated without the use of and/or drawbacks of fluorescent dyes.

The process 900 can be implemented as computer readable instructions on one or more memories or other non-transitory computer readable media, and executed by one or more processors in communication with the one or more memories or other media. In some embodiments, the process 900 can be implemented as computer readable instructions on the memory 220 and/or the memory 240 and executed by the processor 204 and/or the processor 224. In some embodiments, the process 900 can be executed by an imaging system. In some embodiments, a brightfield microscopy imaging system can be configured to execute the process 900. In some embodiments, the brightfield microscopy imaging system can include one or more memories or other non-transitory computer readable media including the process 900 implemented as computer readable instructions on the one or more memories or other non-transitory computer readable media, and one or more processors in communication with the one or more memories or other media configured to execute the computer readable instructions to execute the process 900.

At 904, the process 900 can receive a brightfield image (e.g., the brightfield image 404 in FIG. 4 and/or the brightfield image 504 in FIG. 5) of one or more organoids. In some embodiments, the brightfield image can be preprocessed in order to enhance contrast as described above. In some embodiments, the brightfield image can be a raw image that has not undergone any preprocessing such as contrast enhancement.

At 908, the process 900 can determine if the brightfield image is unprocessed (i.e., raw). If the brightfield image is unprocessed (i.e., "YES" at 908), the process 900 can proceed to 912. If the brightfield image is not unprocessed (i.e., "NO" at 908), the process 900 can proceed to 916.

At 912, the process 900 can preprocess the brightfield image. In some embodiments, the brightfield image can have pixel intensities ranging from $[0, 2^{16}]$. In some embodiments, the process 900 can convert the brightfield image to an unsigned byte format, with values ranging from [0, 255].

In some embodiments, the process 900 can convert the brightfield image to another format with less bits than the original pixel intensity. The process 900 can then stretch and clip each pixel intensity to a desired output range. In some embodiments, the process 900 can determine an input range for the brightfield image by uniformly stretching the 2nd and 98th percentile of pixel intensities in the brightfield image to an output range [0,255].

At 916, the process 900 can provide the brightfield image to a trained model. In some embodiments, the model can include the generator 408 in FIG. 4 trained using the process 800 in FIG. 8, the trained model 508, and/or the neural network 600 trained using the process 800 in FIG. 8. In some embodiments, the trained model can include three neural networks, and each neural network can receive a copy of the brightfield image and output a different channel (e.g., red, green, or blue) of an artificial fluorescent image. In some embodiments, the process 900 can apply the trained model to the brightfield image to generate an artificial fluorescent image.

At 920, the process 900 can receive an artificial fluorescent image from the trained model. In some embodiments, the process 900 can receive three one-channel images from three neural networks included in the trained model and combine the one-channel images into a single three-channel artificial fluorescent image. The artificial fluorescent image can indicate whether cells included in the tumor organoids are alive or dead.

At 924, the process 900 can cause the artificial fluorescent image to be output. In some embodiments, the process 900 can cause the artificial fluorescent image to be output to at least one of a memory (e.g., the memory 220 and/or the memory 240) and/or a display (e.g., the display 116, the display 208, and/or the display 228). The artificial fluorescent image can be used to provide a live/dead count of cells in the organoids. In some embodiments, the process 900 can cause the artificial fluorescent image to be output to an automatic cell counting process in order to receive an accurate live/dead count of cells, a percentage of cells that are viable (e.g., alive) or dead, and/or a cell count report in the artificial fluorescent image. For example, the process 900 can cause the artificial fluorescent image to be output to the CellProfiler available at https://cellprofiler.org. In some embodiments, the process 900 can cause one or more channels of the artificial fluorescent image to be output to an automatic cell counting process in order to receive a cell count report, a percentage of cells that are viable (e.g., alive) or dead, and/or accurate live/dead count of cells in the artificial fluorescent image. In some embodiments, the process 900 can cause the brightfield image to be output to a trained model in order to receive a cell count report, a percentage of cells that are viable (e.g., alive) or dead, and/or accurate live/dead count of cells in the artificial fluorescent image. In some embodiments, the process 900 can cause a combination (e.g., image embeddings combined by concatenation) of the brightfield image and one, two, or three channels of the artificial fluorescent image to be output to an automatic cell counting process in order to receive a cell count report, a percentage of cells that are viable (e.g., alive) or dead, and/or an accurate live/dead count of cells in the artificial fluorescent image.

In some embodiments, at 924, the process 900 can identify cells in the artificial fluorescent image by converting each of the channels to grayscale, enhancing and suppressing certain features such as speckles, ring shapes, neurites, dark holes, identifying primary objects belonging to the all cell channel where the typical diameters of these objects (in pixel units) is set anywhere between 2 and 20 with a minimum cross entropy thresholding method at a smoothing scale of 1.3488, and identifying primary objects again belonging to the dead cells channel where typical diameter is anywhere between 5 and 20 in pixel units. In this way, the process 900 can generate a cell count report. In some embodiments, the process 924 can determine if a drug and/or dosage is effective in killing tumor organoid cells based on the live/dead count of cells. In some embodiments, at 924, the process 900 can extrapolate dose response from a distribution of organoid viability at a single concentration.

In some embodiments, the cell count report may be analyzed to quantify the efficacy of the drug in killing a particular line of tumor organoid cells. For example, if a concentration of a drug causes a lower number of live cells and/or greater number of dead cells, the drug may be rated as more effective in killing a particular line of tumor organoid cells. For each line of tumor organoid cells, characteristics of the tumor organoid cells (for example, molecular data including detected mutations, RNA expression profiles measured in the tumor organoid cells etc., other biomarkers, and/or clinical data associated with the patient from which the tumor organoid was derived) and the results (including the drug efficacy rating) of each drug dose may be saved in a database of drug assay results. These results may be used to match therapies to patients. For example, if a patient has a cancer with characteristics similar to a tumor organoid cell line, drugs rated as effective in killing those tumor organoid cells may be matched to the patient.

In some embodiments, the process 900 can analyze nucleic acid data associated with the one or more tumor organoids. Each tumor organoid included in the one or more tumor organoids can be associated with a specimen (e.g., the specimen the tumor organoid was harvested from). In some embodiments, each specimen can be associated with a patient. The patient can be associated with patient data that can include nucleic acid data. In some embodiments, the nucleic acid data can include whole exome data, transcriptome data, DNA data, and/or RNA data. The nucleic acid data may be used to further analyze the patient. In some embodiments, the process 900 can associate the artificial fluorescent image with information about the specimen (e.g., the nucleic acid data). In some embodiments, the process 900 can provide the artificial fluorescent image and the associated information about the specimen to a database. In some embodiments, the database can include at least seven hundred and fifty artificial fluorescent images.

In some embodiments, the process 900 can generate a report based on the cell count, the cell count report, the nucleic acid data, and/or the artificial fluorescent image. In some embodiments, the process 900 can cause the report to be output to at least one of a memory (e.g., the memory 220 and/or the memory 240) and/or a display (e.g., the display 116, the display 208, and/or the display 228). The process 900 can then end.

Figure 10:
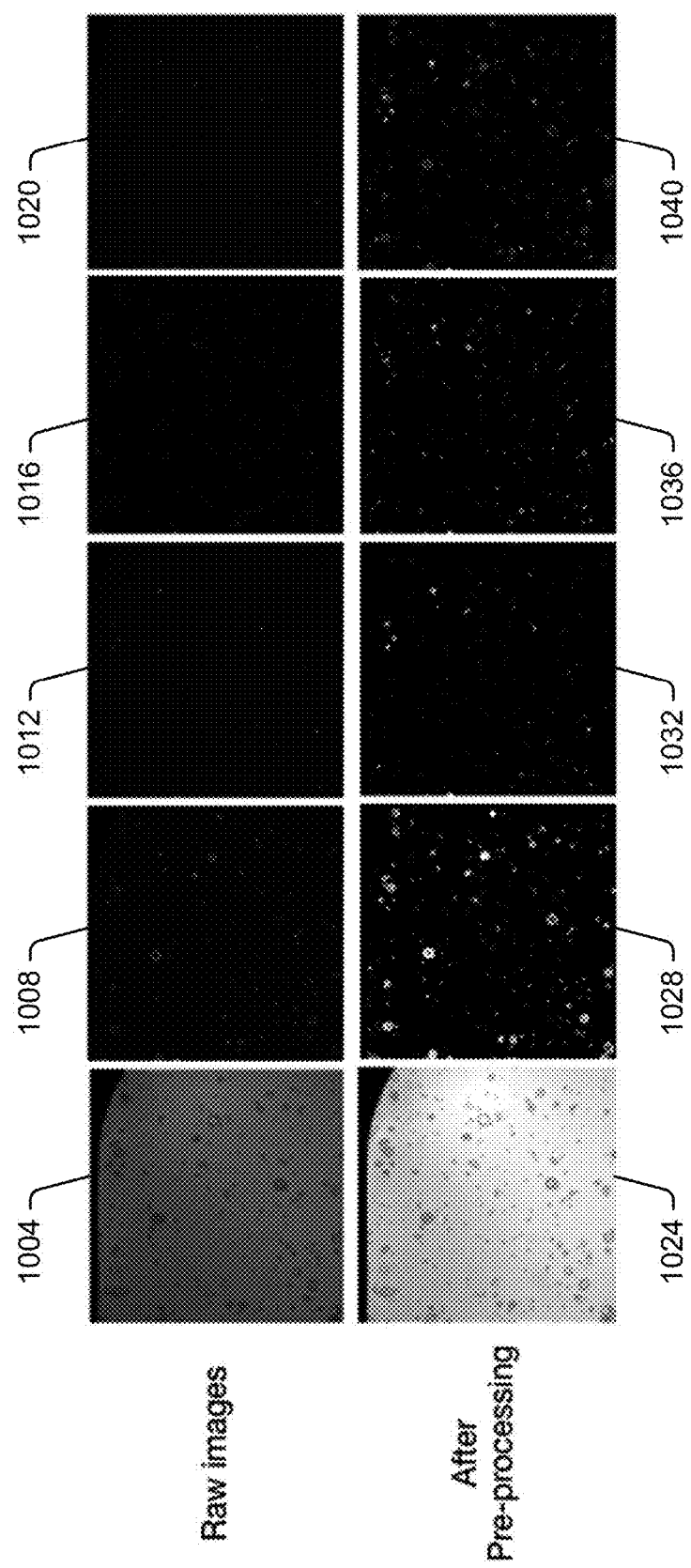
FIG. 10 shows exemplary raw images before preprocessing and after preprocessing.

FIG. 10 shows exemplary raw images before preprocessing and after preprocessing. The raw images before preprocessing include a brightfield image 1004, a blue/all nuclei channel fluorescent image 1008, a green/apoptotic channel fluorescent image 1012, red/pink/dead channel fluorescent image 1016, and a combined 3-channel fluorescent image 1020. The preprocessed images include a brightfield image 1024, a blue/all nuclei channel fluorescent image 1028, a green/apoptotic channel fluorescent image 1032, red/pink/dead channel fluorescent image 1036, and a combined 3-channel fluorescent image 1040. The organoids and cells are brighter and sharper in the preprocessed images. In some embodiments, the preprocessed images 1024-1040 can be generated at 812 in the process 800 in FIG. 8.

Figure 11:
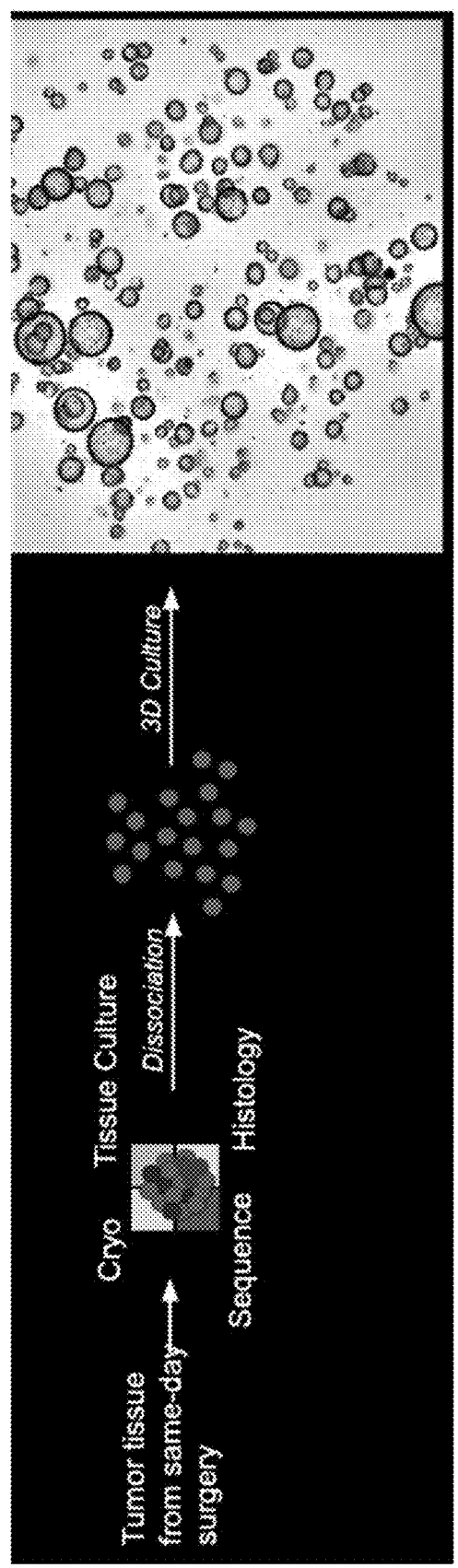
FIG. 11 shows an exemplary flow for culturing tumor organoids. Culture of patient derived tumor organoids.

FIG. 11 shows an exemplary flow 1100 for culturing tumor organoids. Culture of patient derived tumor organoids. The flow 100 can include obtaining tumor tissue from a same-day surgery, disassociating cells from the tumor tissue, and culturing the tumor organoids from the cells. An example of systems and methods for culturing tumor organoids may be found in U.S. patent application Ser. No. 16/693,117, titled "Tumor Organoid Culture Compositions, Systems, and Methods" and filed Nov. 22, 2019, which is incorporated by reference herein in its entirety. Tumor tissue sent from hospitals is cultured to form tumor organoids.

Figure 12:
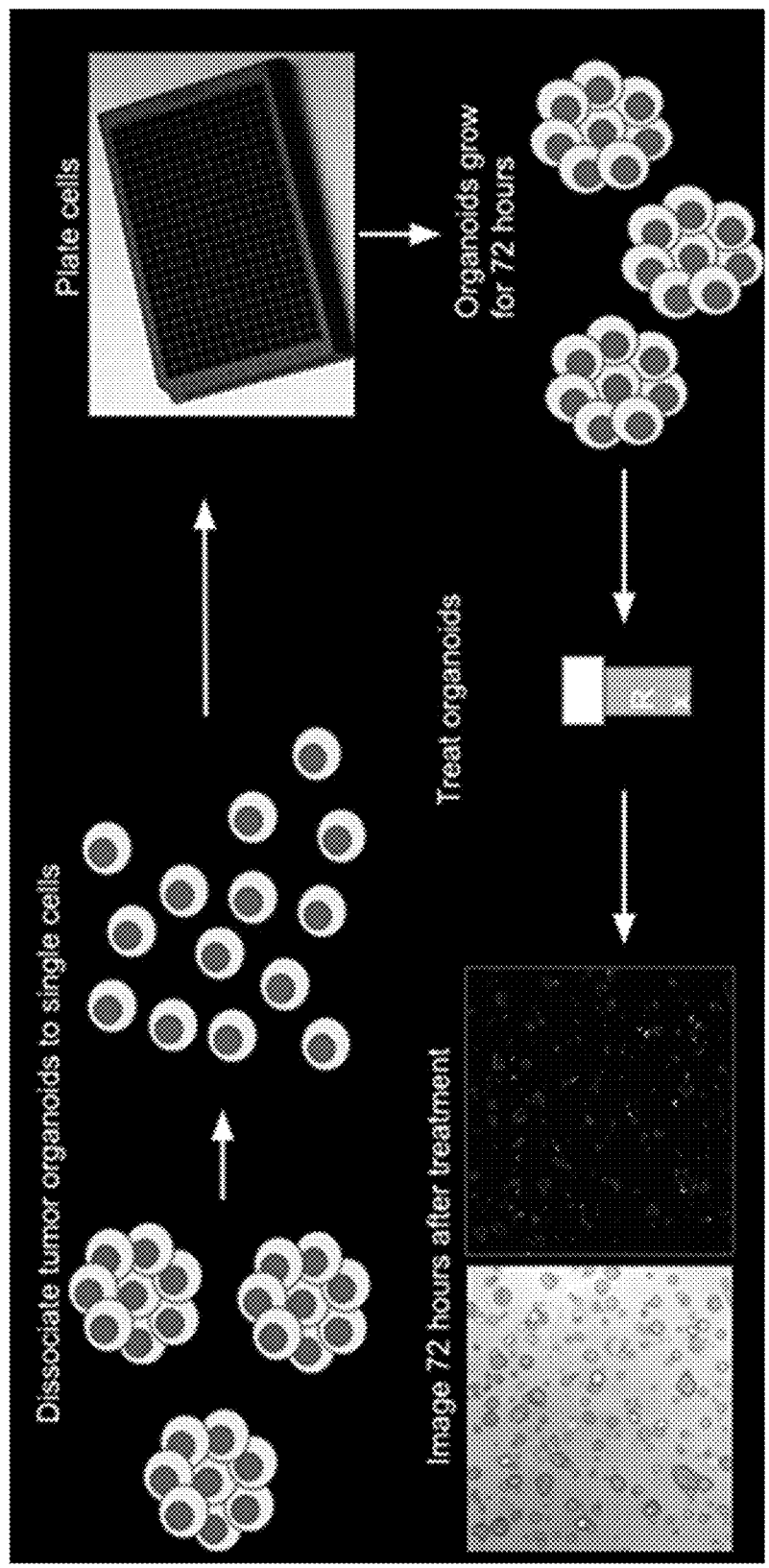
FIG. 12 shows an exemplary flow for conducting drug screens in accordance with systems and methods described herein.

FIG. 12 shows an exemplary flow 1200 for conducting drug screens in accordance with systems and methods described herein. In some embodiments, the flow 1200 can include disassociating tumor organoids into single cells, plating the cells (e.g., in a well plate such as a 96-well plate and/or a 384-well plate), growing the cells into organoids over a predetermined time period (e.g., seventy-two hours), treating the organoids with at least one therapeutic technique, and imaging the tumor organoids a predetermined amount of time (e.g., seventy-two hours) after the tumor organoids are treated. In some embodiments, only brightfield imaging may be performed on the tumor organoids, and any brightfield images generated can be used to generate artificial fluorescent images using the process 900 in FIG. 9. A live/dead count can then be generated based on the artificial fluorescent images. One example of systems and methods for using tumor organoids for drug screens may be found in U.S. Patent Prov. App. No. 62/924,621, titled "Systems and Methods for Predicting Therapeutic Sensitivity" and filed Oct. 22, 2019 (and PCT/US20/56930, filed Oct. 22, 2020), which are incorporated by reference herein in their entireties.

Figure 13:
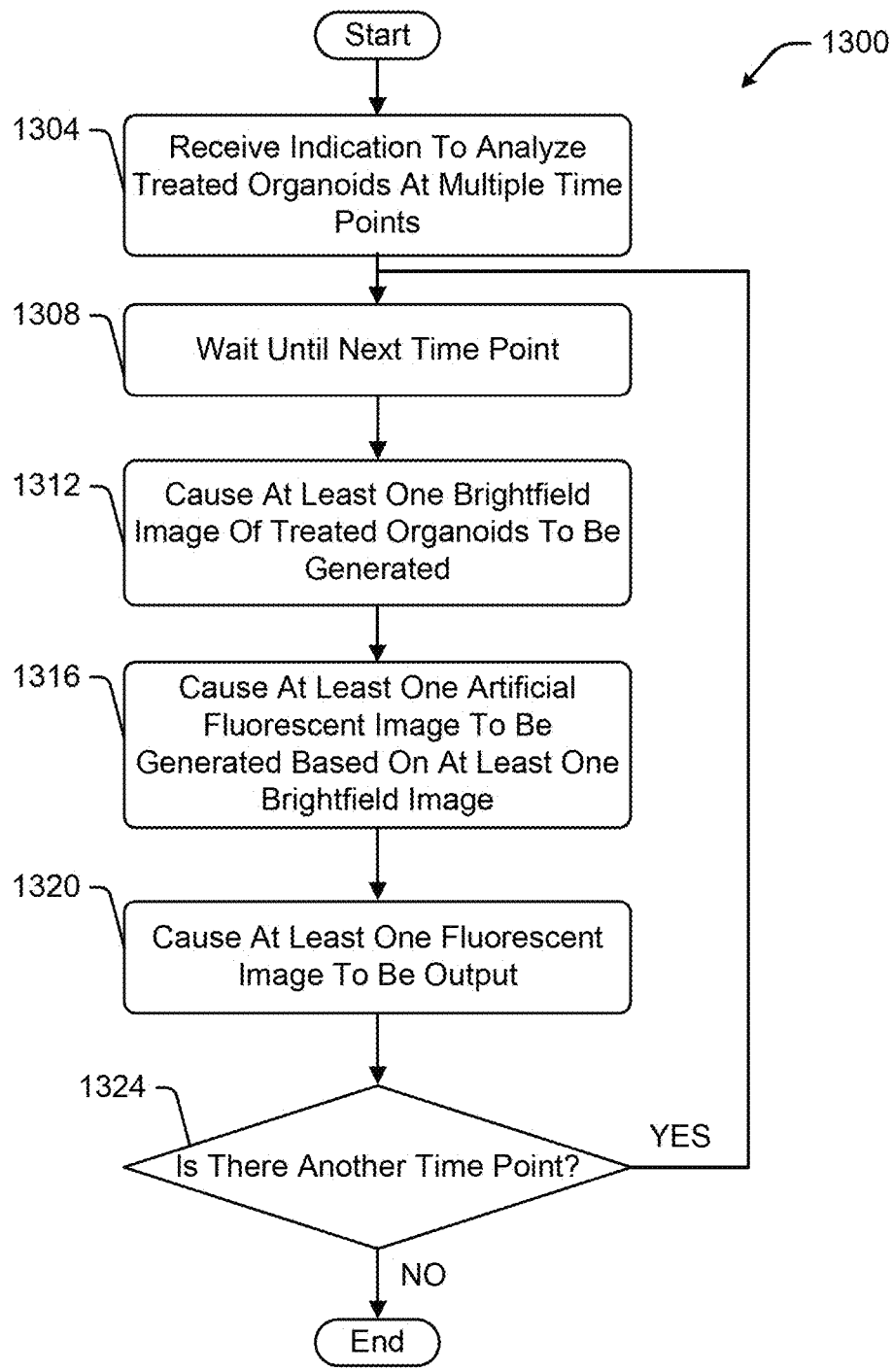
FIG. 13 shows an exemplary process that can generate artificial fluorescent images at multiple time points for at least one organoid.

FIG. 13 shows an exemplary process 1300 that can generate artificial fluorescent images at multiple time points for at least one organoid. Notably, the process 1300 can provide an advantage over standard fluorescent imaging techniques. As mentioned above, fluorescent dyes used to generate standard fluorescent images can damage the cells (e.g., killing the cells) in the organoids, and do not permit fluorescent images to be generated at different time points (e.g., every twelve hours, every twenty-four hours, every seventy-two hours, every week, etc.). In contrast, the process 1300 permits repeated fluorescent imaging of organoids because the process 1300 may only require brightfield images (which do not damage the organoids), and can generate artificial fluorescent images based on the brightfield images.

The process 1300 can be implemented as computer readable instructions on one or more memories or other non-transitory computer readable media, and executed by one or more processors in communication with the one or more memories or other media. In some embodiments, the process 1300 can be implemented as computer readable instructions on the memory 220 and/or the memory 240 and executed by the processor 204 and/or the processor 224. In some embodiments, the process 1300 can be executed by an imaging system. In some embodiments, a brightfield microscopy imaging system can be configured to execute the process 1300. In some embodiments, the brightfield microscopy imaging system can include one or more memories or other non-transitory computer readable media including the process 1300 implemented as computer readable instructions on the one or more memories or other non-transitory computer readable media, and one or more processors in communication with the one or more memories or other media configured to execute the computer readable instructions to execute the process 1300.

At 1304, the process 1300 can receive an indication to analyze treated organoids at multiple time points. In some embodiments, the organoids can be plated (e.g., in a well plate such as a 96-well plate and/or a 384-well plate). In some embodiments, the organoids can be plated on multiple well plates. In some embodiments, the organoids can be plated on one or more petri dishes. In some embodiments, the organoids can be treated using a variety of different treatments, which can vary in drug type, drug concentration, and/or other parameters. In some embodiments, each well in a well plate can be associated with a different treatment.

In some embodiments, the multiple time points can represent a time after the organoids have been treated. For example, a twelve hour time point can be twelve hours after the time at which the organoids were treated. In some embodiments, the multiple time points can be spaced at regular intervals. For example, the multiple time points can occur every twelve hours, every twenty-four hours, every seventy-two hours, every week, etc. In some embodiments, the multiple time points can be irregularly spaced. For example, the time points can include a first time point at six hours, a second time point at twenty four-hours, a third time point at three days, a fourth time point at one week, and a fifth time point at twenty-eight days.

At 1308, the process 1300 can wait until the next time point included in the multiple time points. For example, if six hours has passed since the organoids have been treated, and the next time point is at twelve hours, the process 1300 can wait for six hours.

At 1312, the process 1300 can cause at least one brightfield image of the treated organoids to be generated. In some embodiments, process 1300 can generate the brightfield images of the treated organoids using a bright-field microscope and generating fluorescent images of the cells using a confocal microscope such as a confocal laser scanning microscope. In some embodiments, the process 1300 can preprocess the at least one brightfield image. For example, the process 1300 can, for each brightfield image, perform at least a portion of 912 in the process 900 in FIG. 9. In some embodiments, multiple brightfield images can be generated for each well. For example, for a 96-well plate, there can be about 9-16 sites per well that get imaged.

At 1316, the process 1300 can cause at least one artificial fluorescent image to be generated based on the at least one brightfield image. In some embodiments, the process 1300 can provide each brightfield image to a trained model, and receive an artificial fluorescent image associated with the brightfield image from the trained model. In some embodiments, the trained model can include the generator 408 in FIG. 4 trained using the process 800 in FIG. 8, the trained model 508, and/or the neural network 600 trained using the process 800 in FIG. 8. In some embodiments, the trained model can include a neural network that can receive the input brightfield image and output a single three-channel fluorescent image (e.g., a 256×256×3 image). In some embodiments, the trained model can include three neural networks that can each receive the brightfield image and output a one-channel fluorescent image (e.g., a 256×256×1 image). The one-channel images can then be combined into a single three-channel fluorescent image. The at least one artificial fluorescent image can indicate whether cells included in the tumor organoids are alive or dead. In some embodiments, the process 1300 can apply the trained model to the at least one brightfield image to generate the at least one artificial fluorescent image.

At 1320, the process 1300 can cause the at least one fluorescent image to be output. In some embodiments, the process 1300 can cause the at least one artificial fluorescent image to be output to at least one of a memory (e.g., the memory 220 and/or the memory 240) and/or a display (e.g., the display 116, the display 208, and/or the display 228). The at least one artificial fluorescent image can be used to provide a live/dead count of cells in the organoids. In some embodiments, the process 900 can cause the artificial fluorescent image to be output to an automatic cell counting process in order to get an accurate live/dead count of cells in the artificial fluorescent image. For example, the process 900 can cause the artificial fluorescent image to be output to the CellProfiler available at https://cellprofiler.org. In this way, the process 1300 can automatically generate live/dead counts for multiple wells at multiple time points, which can make drug treatment experiments run faster and gather more data with the same number of wells as compared to standard fluorescent dye imaging techniques that kill cells.

In some embodiments, at 1320, the process 1300 can identify cells in the artificial fluorescent image by converting each of the channels to grayscale, enhancing and suppressing certain features such as speckles, ring shapes, neurites, dark holes, identifying primary objects belonging to the all cell channel where the typical diameters of these objects (in pixel units) is set anywhere between 2 and 20 with a minimum cross entropy thresholding method at a smoothing scale of 1.3488, and identifying primary objects again belonging to the dead cells channel where typical diameter is anywhere between 5 and 20 in pixel units. In this way, the process 1300 can generate a cell count report.

In some embodiments, the process 1300 can analyze nucleic acid data associated with the one or more tumor organoids. Each tumor organoid included in the one or more tumor organoids can be associated with a specimen (e.g., the specimen the tumor organoid was harvested from). In some embodiments, each specimen can be associated with a patient. The patient can be associated with patient data that can include nucleic acid data. In some embodiments, the nucleic acid data can include whole exome data, transcriptome data, DNA data, and/or RNA data. The nucleic acid data may be used to further analyze the patient. In some embodiments, the process 1300 can associate the artificial fluorescent image with information about the specimen (e.g., the nucleic acid data). In some embodiments, the process 1300 can provide the artificial fluorescent image and the associated information about the specimen to a database. In some embodiments, the database can include at least seven hundred and fifty artificial fluorescent images.

In some embodiments, the process 1300 can generate a report based on the cell count, the cell count report, the nucleic acid data, and/or the artificial fluorescent image. In some embodiments, the process 1300 can cause the report to be output to at least one of a memory (e.g., the memory 220 and/or the memory 240) and/or a display (e.g., the display 116, the display 208, and/or the display 228). The process 1300 can then end.

In some embodiments, the process 800 in FIG. 8, the process 900 in FIG. 9, and/or the process 1300 in FIG. 13 can be included in the organoids image analysis application 132 in FIG. 1.

FIG. 14 shows a table representing an exemplary assay or well plate arrangement. More specifically, the table shows an arrangement of treatment therapies by well in a 24×16 well plate.

In some embodiments, to populate the well plate with tumor organoids, single cell suspensions of tumor organoid cells can be generated using a predetermined protocol. In some embodiments, to populate a 24×16 well plate, a 24-well plate culture can be dissociated into single cells and seeded in 384-well plates in a mix of 30% Matrigel and 70% media. This setup can allow tumor organoids to form from individual cells for the assay, maintaining tumor organoid heterogeneity in each well. About 2000 cells can be seeded per well allowing enough tumor organoids (TO's) to form while not overcrowding the plate.

The number of usable wells in each 384-well plate can be 330 wells. There can be two sites in each well which get imaged. For a 96-well plate, there can be about 9-16 sites per well that get imaged. In some embodiments, each row in the well plate can receive a different drug. In some embodiments, a control (e.g., Staurosporine) can be fixed in row A. The vehicle can be column 2 where the first half is given DMSO and the second half Staurosporine. In some embodiments, each row can receive drug concentration in technical triplicate.

Example 1

In this example, Tumor Organoids in each well were stained using three fluorophores for high content fluorescent confocal imaging analysis. In order to obtain the fluorescent readouts a high content imager (ImageXpress Confocal, Molecular Devices) was utilized for data acquisition. Images were acquired at 10× magnification with a 50 micron slit spinning disk aperture. Four channels were acquired using incandescent brightfield, and LED light sources using manufacturer's default settings for 4',6-diamidino-2-phenylindole (DAPI), Fluorescein isothiocyanate (FITC), and Cyanine 5 (CY5) to acquire data from Hoechst 33342 (Thermo), Caspase-3/7 reagent (Essen Bioscience), or TO-PRO-3 (Thermo) respectively.

In this example, the experimental setup used a 384 well plate, with 330 usable wells within each plate. Since each well has two sites that get imaged, each plate has a total of 660 paired brightfield and fluorescence images. At a magnification of 10×, two images are taken per well at 2 sites with a stack of images in the Z plane ranging from 1-100 heights with increments as high as 15 microns per z plane. The Z stack images are projected to 2D for analysis. The three fluorophores for each brightfield image visualizes all nuclei (Hoechst 33342, blue), apoptotic cells (Caspase-3/7 Apoptosis Assay Reagent, green), and dead cells (TO-PRO-3, red).

The final dataset contained registered fluorophores from two patient lines. Patient line A with colon cancer consisted of 9900 paired brightfield and fluorescent images. Patient line B with gastric cancer consisted of 10557 paired brightfield and fluorescent images.

A model in accordance with the generator 408 and the discriminator 416 was implemented in Pytorch version 1.0.0. The colon cancer organoid patient line A was selected to evaluate performance for all models analyzed. The organoid line contained 8415 paired brightfield and fluorescent images across 15 experimental plates, which was subjected to an 80-10-10 split for training, test and validation, resulting in 6930 images for training, 742 in validation and 743 for test. Each image was loaded one at a time. Fine tuning of parameters was achieved using only validation set. The learning rate was fixed at 0.0002 for the first 15 epochs of training and consequently linearly decayed to 0 for the next 10 epochs yielding a total of 25 epochs for training.

A fixed set of 743 brightfield and corresponding fluorescent images randomly sampled from 15 experimental plates was chosen as a test set. Evaluation for all experiments was performed on the fixed test set. First, the effect of training three separate models (three-model) was evaluated for each fluorophore channel versus training one single model (one-model) on the combined fluorescent readout. For the three-model, predictions for each fluorophore were combined at the end and evaluated. Performance was evaluated both quantitatively using structural similarity index and root mean squared error as well as qualitatively visually using heatmaps.

Figure 15:
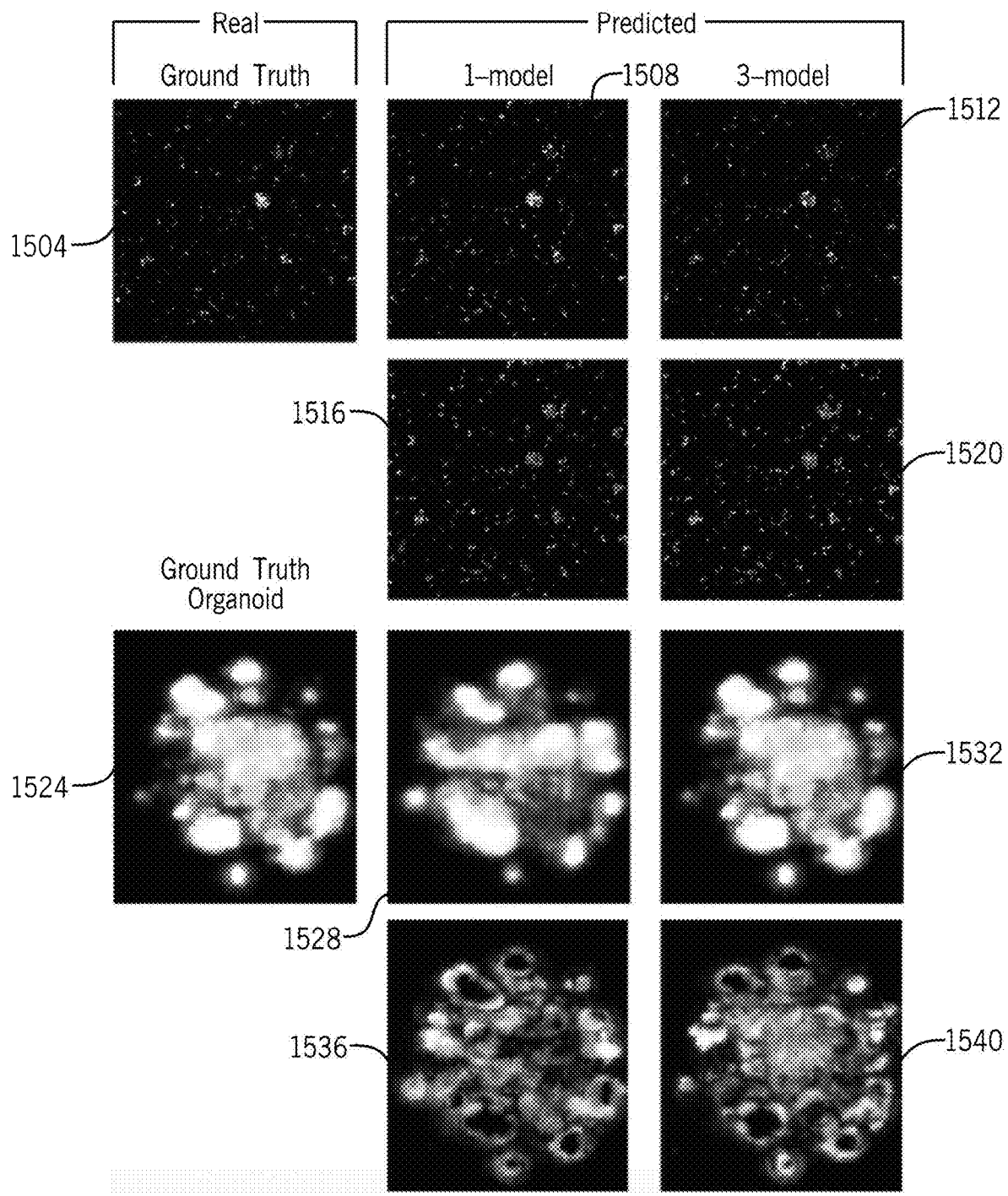
FIG. 15 shows an example of images generated using a single neural network model and a three neural network model.

No significant improvement in fluorescent stain prediction was observed when using the three-model, which trained a separate generator for each channel. Table 1 reports the average SSIM and root mean squared error across each channel's predictions for all 743 test images, and FIG. 15 shows example images and organoids. Furthermore, because the three-model required three times as many computing resources with only limited RMSE improvement, it was reasoned that a one-model implementation could sufficiently and efficiently perform image-to-image translation from brightfield image to a combined fluorescent readout. In Table 1, lower RMSE and higher SSIM indicates better performance.

TABLE 1

| Experiment | Avg. RMSE | Avg. SSIM |
| --- | --- | --- |
| three-model | 1.3655 | 0.92299 |
| one-model | 1.39952 | 0.92383 |

FIG. 15 shows an example of images generated using a single neural network model (one-model) and a three neural network model (three-model). A first image 1504 is an example of a ground truth fluorescence image. A second image 1508 is an example of an artificial fluorescent image generated using a one-model with a single neural network that can receive an input brightfield image and output a single three-channel fluorescent image (e.g., a 256×256×3 image). A third image 1512 is an example of an artificial fluorescent image generated using a three-model with three neural networks that can each receive the brightfield image and output a one-channel fluorescent image (e.g., a 256×256×1 image). A fourth image 1516 is an example of a greyscale error map between the second image 1508 and the ground truth image 1504. A fifth image 1520 is an example of a greyscale error map between the third image 1512 and the ground truth image 1504. A sixth image 1524, a seventh image 1528, an eighth image 1532, a ninth image 1536, and a tenth image 1540 are examples of a zoomed-in organoid in the first image 1504, the second image 1508, the third image 1512, the fourth image 1516, and the fifth image 1520, respectively.

Next, the effect of adding SSIM loss to the 1-model objective function was elaborated. The objective function in Equation 1 is a weighted combination of L1 and SSIM loss ($\lambda$L1+$\beta$SSIM). The influence of SSIM was tested by uniformly evaluating={0; 0.25; 0.5; 0.75; 1}. Table 2 highlights the performance on the held-out test set using different $\beta$. A combination of $\beta$=0.75 (and $\lambda$=0.25), shows the best performance of the trained model (e.g., the trained model 508) in terms of both SSIM and RMSE.

TABLE 2

| Experiment | Avg. RMSE | Avg. SSIM |
|---|---|---|
| β = 0 | 1.39952 | 0.92383 |
| β = 1 | 1.49570 | 0.91110 |
| β = 0.25 | 1.37369 | 0.92691 |
| β = 0.5 | 1.36477 | 0.92781 |
| β = 0.75 | 1.35165 | 0.92829 |

To determine if the accuracy of the trained model (β=0.75) was driven by specific improvement in the prediction of a single fluorophore, such as prediction of DAPI (all cells) or FITC (dying/apoptotic cells), the average RMSE and SSIM across each channel were examined. The results are shown in Table 3.

TABLE 3

| Channel | Avg. RMSE | Avg. SSIM |
|---|---|---|
| Dead Cells | 1.6311 | 0.92306 |
| Dead/Dying Cells | 1.1015 | 0.92759 |
| All Cells | 1.7083 | 0.91807 |

The model trained with β=0.75 demonstrated consistent RMSE and SSIM scores across all channels. The performance of how the model trained with β=0.75 performed on two new patient colorectal cancer organoid lines (organoids lines B and C) was evaluated. Each new line had a total of 648 brightfield and corresponding fluorescent readouts across different plates. Table 4 demonstrates that a model trained on β=0.75 trained on a single organoid can transfer to other organoid lines. However, the difference between the two lines suggests some limitations. The difference between the two lines suggests that different colorectal cancer organoid lines may present different morphological features that may limit model transfer. In that event, retraining the current best model with some data from organoid line C or employing domain adaptation techniques can facilitate better generalizability to organoid line C.

TABLE 4

| Experiment | Avg. RMSE | Avg. SSIM |
|---|---|---|
| Organoid line B | 1.42222 | 0.91062 |
| Organoid line C | 2.03384 | 0.78431 |

Example 2

Experiments were performed to try and improve model performance. Candidate models included a GANLoss+SSIM model, a GANLoss+SSIM+L1 model trained using a GANLoss+0.17L1+0.83 SSIM model, a GANLoss+MS-SSIM model, and a GANLoss+0.83MS-SSIM+0.17L1 model.

Initially, three separate Pix2Pix models were employed to train the individual fluorescent channels. The Avg SSIM and RMSE results over the same 743 blind test images as described in Example 1 are shown below. Tables 5-8 show results of the candidate models implemented in three-model fashion. Table 5 shows results of the GANLoss+SSIM model. Table 6 shows results of the GANLoss+0.83SSIM+0.17L1 model. Table 7 shows results of the GANLoss+MS-SSIM model. Table 8 shows results of the GANLoss+0.83 MS-SSIM+0.17 L1 model.

TABLE 5

| Experiment | Avg RMSE | Avg SSIM |
|---|---|---|
| Dead Cells | 1.65133 | 0.91736 |
| Dead/Dying Cells | 1.12827 | 0.91784 |
| All cells | 1.73630 | 0.91097 |

TABLE 6

| Experiment | Avg RMSE | Avg SSIM |
|---|---|---|
| Dead cells | 1.56781 | 0.92950 |
| Dead/Dying Cells | 1.10735 | 0.92782 |
| All cells | 1.70604 | 0.92024 |

TABLE 7

| Experiment | Avg RMSE | Avg SSIM |
|---|---|---|
| Dead cells | 1.64130 | 0.92027 |
| Dead/Dying Cells | 1.13677 | 0.91956 |
| All cells | 1.72046 | 0.91725 |

TABLE 8

| Experiment | Avg RMSE | Avg SSIM |
|---|---|---|
| Dead cells | 1.61705 | 0.92530 |
| Dead/Dying Cells | 1.12485 | 0.92856 |
| All cells | 1.72099 | 0.91723 |

Fluorescent Combined 3 Channel Image Results

The results in Table 9 below take the 3 channel pix2pix models per experiment and combine them to form their 3 channel IF counterpart. The individual channels were trained separately and combined by stacking RGB.

TABLE 9

| Experiment | Avg RMSE | Avg SSIM |
|---|---|---|
| GANLoss + L1 | 1.36550 | 0.92299 |
| GANLoss + SSIM | 1.38915 | 0.91558 |
| GANLoss + SSIM + L1 | 1.33759 | 0.92586 |
| GANLoss + MS-SSIM | 1.39169 | 0.91875 |
| GANLoss + MS-SSIM + L1 | 1.37136 | 0.92372 |

It was observed that GANLoss+SSIM or GANLoss+MS-SSIM standalone do not perform as well as other models. A combination of GANLoss+0.83 SSIM+0.17L1 seems to perform the best. It was also found that GANLoss+L1 and GANLoss+SSIM do not do a good job with detecting blurry bad quality images. The GANLoss+SSIM+L1 model was able to accurately detect blurry artifacts. The GANLoss+SSIM+L1 model recognized artifacts and blurs better than other models and avoided prediction altogether when blurs/artifacts are present in the brightfield image.

Example 3

In Example 2, the process of training 3 separate pix2pix models for multiple different objective functions proved to require several GPU's (3 per model) and extra effort in data curation. A similar performance analysis was done to check if similar/better RMSE and SSIM values were observed by directly training from brightfield to 3 channel fluorescence using a single Pix2Pix model in an attempt to reduce GPU usage.

Table 10 below shows the results of directly training to transfer style to IF image for the same set of objective functions on the same test set of 743 images belonging to 10245. The number of GPU's was reduced from 15 GPU's to 5 GPU's and the performance although not too significant, is marginally better. Thus, it may be preferable to use a one-model to generate artificial fluorescent images because performance can be at least as good as a three-model, with one third of the computational requirements. In particular, a one-model trained using an objective function of GANLoss+0.83 MS-SSIM+0.17 L1 model may outperform other one-models and/or three-models trained on the same training data.

TABLE 10

| Experiment | Avg RMSE | Avg SSIM |
| --- | --- | --- |
| GANLoss + L1 | 1.39952 | 0.92383 |
| GANLoss + SSIM | 1.49570 | 0.91110 |
| GANLoss + SSIM + L1 | 1.35567 | 0.92890 |
| GANLoss + MS-SSIM | 1.44965 | 0.91841 |
| GANLoss + MS-SSIM + L1 | 1.39880 | 0.92577 |

Table 11 below shows results of a number of one-models trained using different objective functions. GANLoss+0.75 SSIM+0.25 L1 had the best RMSE, while GANLoss+0.83 SSIM+0.17 L1 had the best SSIM performance.

TABLE 11

| Experiment | Avg RMSE | Avg SSIM |
| --- | --- | --- |
| GANLoss + 0.5 SSIM + 0.5 L1 | 1.36478 | 0.92781 |
| GANLoss + 0.5 MSSSIM + 0.5 L1 | 1.40834 | 0.92434 |
| GANLoss + 0.17 SSIM + 0.83 L1 | 1.34783 | 0.92641 |
| GANLoss + 0.17 MSSSIM + 0.83 L1 | 1.37889 | 0.92560 |
| GANLoss + 0.25 SSIM + 0.75 L1 | 1.37369 | 0.92691 |
| GANLoss + 0.25 MSSSIM + 0.75 L1 | 1.37788 | 0.92547 |
| GANLoss + 0.75 SSIM + 0.25 L1 | 1.35166 | 0.92830 |
| GANLoss + 0.75 MSSSIM + 0.25 L1 | 1.39788 | 0.92541 |
| GANLoss + 0.83 SSIM + 0.17 L1 | 1.35567 | 0.92890 |
| GANLoss + 0.83 MSSSIM + 0.17 L1 | 1.39880 | 0.92577 |

Example 4

This example details an exemplary cell profiler readout. The cell profiler readout includes all cell counts and dead cell counts of real fluorescent images and corresponding artificial fluorescent images. In Table 12, each row indicates a particular site in a well within an experimental plate and whether it is an artificial or a real image imaged from an ImageXpress Micro microscope.

TABLE 12

| Count_Cells | Count_PrimaryDeadCells | FileName_Native | ImageNumber |
| --- | --- | --- | --- |
| 281.0 | 170.0 | Assay10B_10245-10301_A03_s1_fake B.png | 1 |
| 295.0 | 107.0 | Assay10B_10245-10301_A03_s1_real_B.png | 2 |
| 269.0 | 211.0 | Assay10B_10245-10301_A20_s2_fake_B.png | 3 |
| 270.0 | 210.0 | Assay10B_10245-10301_A20_s2_real_B.png | 4 |
| 549.0 | 162.0 | Assay10B_10245-10301_C20_s1_fake_B.png | 5 |

Table 13 below shows plate and well information for each image along with the SSIM/RMSE values.

TABLE 13

| Count_Cells | Count_PrimaryDeadCells | file | file Name | type | plate | well | well type | SSIM | RMSE |
| --- | --- | --- | --- | --- | --- | --- | --- | --- | --- |
| 281.0 | 170.0 | [Assay10B, 10245-10301, A03, s1, fake, B] | Assay 10B_10245-10301_A03_s1 | fake | Assay 10B | A03 | A | 0.947745 | 1.165460 |
| 295.0 | 107.0 | [Assay10B, 10245-10301, A03, s1, real, B] | Assay 10B_10245-10301_A03_s1 | real | Assay 10B | A03 | A | 0.947745 | 1.165460 |
| 269.0 | 211.0 | [Assay10B, 10245-10301, A20, s2, fake, B] | Assay 10B_10245-10301_A20_s2 | fake | Assay 10B | A20 | A | 0.956855 | 1.011834 |

TABLE 13-continued

| Count_Cells | Count_PrimaryDeadCells | file | file Name | type | plate | well | well type | SSIM | RMSE |
|---|---|---|---|---|---|---|---|---|---|
| 270.0 | 210.0 | [Assay10B, 10245-10301, A20, s2, real, B] | Assay 10B_10245-10301_A20_s2 | real | Assay 10B | A20 | A | 0.956855 | 1.011834 |
| 549.0 | 162.0 | [Assay10B, 10245-10301, C20, s1, fake, B] | Assay 10B_10245-10301_C20_s1 | fake | Assay 10B | C20 | C | 0.940647 | 1.194703 |

Table 13 shows that the fluorescent images can produce similar cell counts as compared to the corresponding real fluorescent image.

Example 5

In some embodiments, a large scale drug assay in tumor organoids can increase throughput of the assay. This high throughput screening can be used for validation or testing of drug efficacy or for discovery of novel therapeutics. In some embodiments, 3D TOs may be more similar to a tumor from which they are derived than a 2-dimensional clonal established cell line derived from that tumor.

In this example, tumor tissue removed by a biopsy is dissociated into single cells and grown into a 3-dimensional (3D) tumor organoid (TO) culture including TOs. TOs are then dissociated into single cells and grown in a 384-well tissue culture plate for 72 hours. Each well receives either no treatment (or a mock treatment) or a dose (concentration) of a small molecule inhibitor or chemotherapy drugs and the effect of the treatment on the cells in the TO is measured. In one example, over 1,000 drugs may be tested. In another example, several concentrations of 140 drugs may be tested.

In one example, the treatment is one of three hundred and fifty-one small molecule inhibitors and seven doses are tested for each treatment on two different organoid types (two organoid cell lines), each derived from a separate patient sample. In this example, one organoid type is a gastric cancer organoid line and the other is a colorectal cancer organoid line. In one example, the effect of the treatment may be measured by counting the number of dead cells and/or viable cells in a well after exposure to a treatment. In this example of fluorescent staining, cell nuclei are stained blue with Hoechst 33342, dying (apoptotic) cells are stained green with Caspase-3/7 Apoptosis Assay Reagent, and dead cells are stained red with TO-PRO-3.

In this example, the gastric cancer organoid line has an amplification of the HER2 gene. Afatinib (a drug that targets HER2, among other molecules) and two other drugs that target HER2 kill this gastric cancer organoid line effectively.

In some embodiments, the methods and systems described above may be utilized in combination with or as part of a digital and laboratory health care platform that is generally targeted to medical care and research. It should be understood that many uses of the methods and systems described above, in combination with such a platform, are possible. One example of such a platform is described in U.S. patent application Ser. No. 16/657,804, titled "Data Based Cancer Research and Treatment Systems and Methods", and filed Oct. 18, 2019, which is incorporated herein by reference and in its entirety for all purposes.

For example, in some embodiments of the methods and systems described above may include microservices constituting a digital and laboratory health care platform supporting artificial fluorescent image generation and analysis. Some embodiments may include a single microservice for executing and delivering artificial fluorescent image generation or may include a plurality of microservices each having a particular role which together implement one or more of the embodiments above. In one example, a first microservice may execute training data generation in order to deliver training data to a second microservice for training a model. Similarly, the second microservice may execute model training to deliver a trained model according to at least some embodiments. A third microservice may receive a trained model from a second microservice and may execute artificial fluorescent image generation.

Some embodiments above can be executed in one or more microservices with or as part of a digital and laboratory health care platform, one or more of such micro-services may be part of an order management system that orchestrates the sequence of events as needed at the appropriate time and in the appropriate order necessary to instantiate embodiments above. A micro-services based order management system is disclosed, for example, in U.S. Prov. Patent Application No. 62/873,693, titled "Adaptive Order Fulfillment and Tracking Methods and Systems", filed Jul. 12, 2019, which is incorporated herein by reference and in its entirety for all purposes.

For example, continuing with the above first and second microservices, an order management system may notify the first microservice that an order for training a model has been received and is ready for processing. The first microservice may execute and notify the order management system once the delivery of training data is ready for the second microservice. Furthermore, the order management system may identify that execution parameters (prerequisites) for the second microservice are satisfied, including that the first microservice has completed, and notify the second microservice that it may continue processing the order to generate a trained model according to some embodiments.

When the digital and laboratory health care platform further includes a report generation engine, the methods and systems described above may be utilized to create a summary report of a patient's genetic profile and the results of one or more insight engines for presentation to a physician. For instance, the report may provide to the physician information about the extent to which a specimen that was used to harvest organoids. For example, the report may provide a genetic profile for each of the tissue types, tumors, or organs in the specimen. The genetic profile may represent genetic sequences present in the tissue type, tumor, or organ and may include variants, expression levels, information about gene products, or other information that could be derived from genetic analysis of a tissue, tumor, or organ. The report may include therapies and/or clinical trials matched based on a portion or all of the genetic profile or insight engine findings and summaries. For example, the therapies may be matched according to the systems and methods disclosed in U.S. Prov. Patent Application No. 62/804,724, titled "Therapeutic Suggestion Improvements Gained Through Genomic Biomarker Matching Plus Clinical History", filed Feb. 12, 2019, which is incorporated herein by reference and in its entirety for all purposes. For example, the clinical trials may be matched according to the systems and methods disclosed in U.S. Prov. Patent Application No. 62/855,913, titled "Systems and Methods of Clinical Trial Evaluation", filed May 31, 2019, which is incorporated herein by reference and in its entirety for all purposes.

The report may include a comparison of the results to a database of results from many specimens. An example of methods and systems for comparing results to a database of results are disclosed in U.S. Prov. Patent Application No. 62/786,739, titled "A Method and Process for Predicting and Analyzing Patient Cohort Response, Progression and Survival", and filed Dec. 31, 2018, which is incorporated herein by reference and in its entirety for all purposes. The information may be used, sometimes in conjunction with similar information from additional specimens and/or clinical response information, to discover biomarkers or design a clinical trial.

When the digital and laboratory health care platform further includes application of one or more of the embodiments herein to organoids developed in connection with the platform, the methods and systems may be used to further evaluate genetic sequencing data derived from an organoid to provide information about the extent to which the organoid that was sequenced contained a first cell type, a second cell type, a third cell type, and so forth. For example, the report may provide a genetic profile for each of the cell types in the specimen. The genetic profile may represent genetic sequences present in a given cell type and may include variants, expression levels, information about gene products, or other information that could be derived from genetic analysis of a cell. The report may include therapies matched based on a portion or all of the deconvoluted information. These therapies may be tested on the organoid, derivatives of that organoid, and/or similar organoids to determine an organoid's sensitivity to those therapies. For example, organoids may be cultured and tested according to the systems and methods disclosed in U.S. patent application Ser. No. 16/693,117, titled "Tumor Organoid Culture Compositions, Systems, and Methods", filed Nov. 22, 2019; and U.S. Prov. Patent Application No. 62/924,621, which are incorporated herein by reference and in their entirety for all purposes.

When the digital and laboratory health care platform further includes application of one or more of the above in combination with or as part of a medical device or a laboratory developed test that is generally targeted to medical care and research, such laboratory developed test or medical device results may be enhanced and personalized through the use of artificial intelligence. An example of laboratory developed tests, especially those that may be enhanced by artificial intelligence, is disclosed, for example, in U.S. Provisional Patent Application No. 62/924,515, titled "Artificial Intelligence Assisted Precision Medicine Enhancements to Standardized Laboratory Diagnostic Testing", and filed Oct. 22, 2019, which is incorporated herein by reference and in its entirety for all purposes.

It should be understood that the examples given above are illustrative and do not limit the uses of the systems and methods described herein in combination with a digital and laboratory health care platform.

The systems and methods disclosed herein can reduce (1) the time required for imaging the plates (2) the need for toxic dyes that could cause cell death and skew results and (3) the amount of manual labor to add those dyes, allowing larger numbers of drugs or concentrations of drugs to be tested (for example, by a factor of ten). The systems and methods reduce the number of images generated to analyze each plate (for example, by a factor of four or 5, or from 10,000 images to about 2,000-2,500 images) by receiving a brightfield image and predicting the corresponding fluorescent readout and allowing label-free (dye-free) estimation of cell viability (for example, the percentage of cells in a well or in an image that are alive at a given time) at multiple time points.

The systems and methods described herein may be used to make hundreds or more measurements in each cell culture well to assess heterogeneity of the drug response (for example, surviving or dying after treatment) of the organoids, which may be done on a per organoid basis (for example, analyzing the cell death or percent of viable cells in each organoid). Multiple measurements include fluorescence intensity, cell growth, cell death, cells per organoid, cells per well, dose response (for example, graphing % cell viability vs. drug dose, calculating a best fit curve or drug dose response curve, and measuring the area above the curve and below the 100% viability intercept), etc. These measurements facilitate determination of cellular mechanisms of a drug response and/or the detection of drug-resistant subpopulations of organoids within an organoid line or within a cell culture well. Drug efficacy (for example, dose response) and specificity may be measured. Drug efficacy of all drugs for one or more organoid lines may be plotted. In one example, the x-axis shows drug efficacy for a first organoid line and the y-axis shows drug efficacy for a second organoid line. In this plot, drugs near the upper right corner were effective against both organoid lines. Drugs near the upper left or lower right corners were effective against one of the organoid lines.

Drugs that kill an organoid line may also be categorized and quantified according to their drug target. For example, the thirty most effective drugs that kill an organoid line may be organized by target in a bar graph, showing the number of effective drugs per target.

Figure 16:
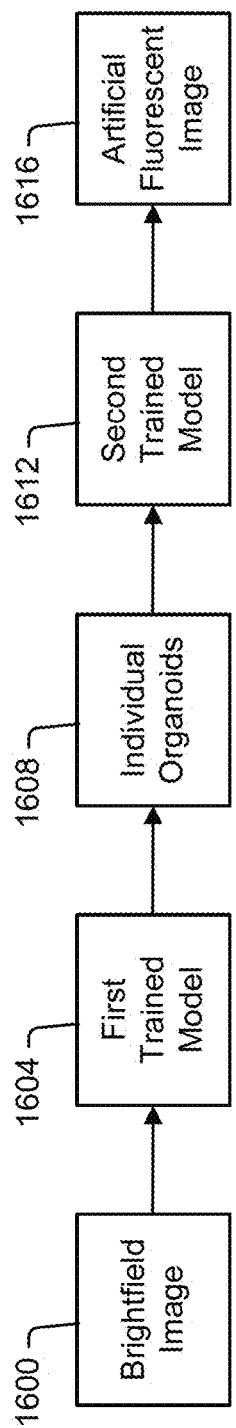
FIG. 16 shows a flow for generating an artificial fluorescent image using a first trained model and a second trained model.

Referring now to FIG. 16, a flow for generating an artificial fluorescent image 1616 using a first trained model 1604 and a second trained model 1612 is shown. The first trained model 1604 can generate one or more individual organoids 1608 (e.g., organoid segmentations) based on a brightfield image 1600. The brightfield image 1600 may contain one or more organoids, and the trained first model 1604 can identify each organoid by segmenting the organoids 1608 from the brightfield image 1600. In some embodiments, the first trained model can include an artificial neural network. In some embodiments, the artificial neural network can include a Mask-RCNN network.

In some embodiments, the first trained model 1604 and the second trained model can be used to predict drug response and other characteristics of an organoid line based on viable cells and/or morphology associated with each individual tumor organoid (TO) in the brightfield image 1600.

Assessing each organoid individually may provide better information about treatments than if the organoids are assessed in place in the brightfield image 1600. Each TO may represent a different tumor clone present in the specimen. Each TO may exhibit a different therapeutic response to the different drugs at different dosage levels. Instead of assessing viabilities of the TOs by aggregating the viabilities across the entire field-of-view in an image, understanding the distribution of the viabilities at a per-organoid level (for example, how many cells in each organoid are viable) and possibly aggregating the viabilities of the TOs belonging to the same tumor clone may offer a better understanding of the response of organoids to the drugs, and by extension, a better understanding of the response of a patient to the drugs.

In some embodiments, the first trained model 1604 can be trained to segment organoids out from the brightfield image 1600 using a training set of brightfield images annotated with bounding boxes around the individual organoids. In some embodiments, the first trained model 1604 can generate masks and bounding boxes around every organoid in the brightfield image. In some embodiments, the first trained model 1604 can generate model embeddings that can be used to generate features based on the organoids in order to assess viability and morphology.

In some embodiments, the second trained model 1612 can include the generator 408 trained to generate an artificial fluorescent image based on an input brightfield organoid. The second trained model 1612 can be trained on a training set of individual brightfield organoids and individual fluorescent organoids. Each individual fluorescent organoid can be used to generate a viability. The viabilities for all organoids can be aggregated. A distribution of viabilities per organoid can be generated and/or visualized. In some embodiments, the distribution of live/dead cells per organoid can be calculated to get a prediction or extrapolation of dose response from the distribution of Organoid viability at a single drug concentration. In some embodiments, a process can aggregate the viabilities of different tumor clones among the organoids if side information is available to determine which cropped out TO belongs to which tumor clone.

In some embodiments, the morphologies of every organoid can be visualized. In some embodiments, the morphologies of the tumor organoids can be visualized, either by using handcrafted features or model embeddings, and clustering in a supervised or unsupervised setting. In some embodiments, the morphological clusters can be associated with cluster viabilities, and by extension, drug response. In some embodiments, the TO morphology can be used to predict drug response.

Figure 17:
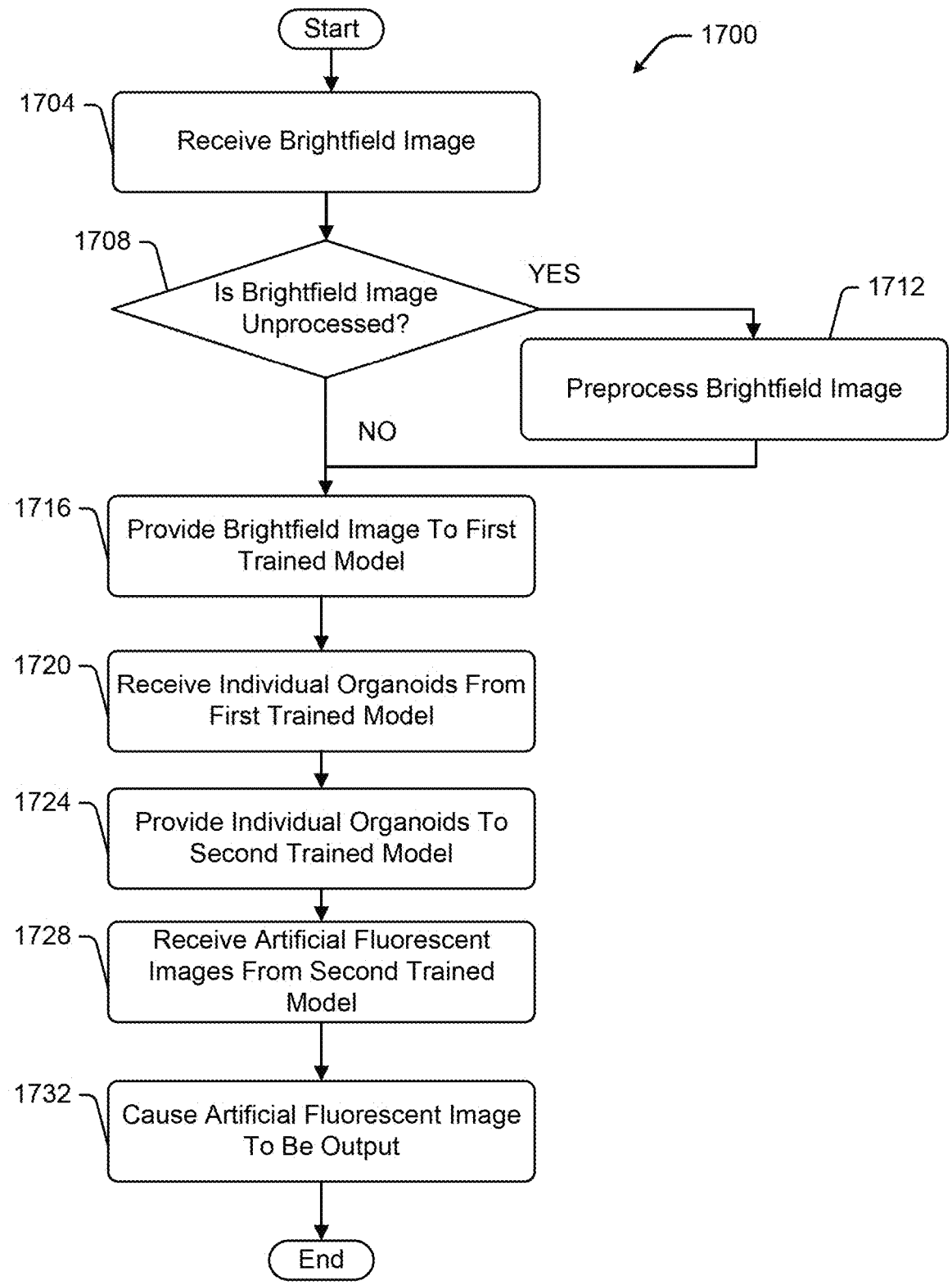
FIG. 17 shows a process for generating fluorescent images of tumor organoids.

Referring now to FIG. 16 as well as FIG. 17, a process 1700 for generating fluorescent images of tumor organoids is shown. The process 1700 can be implemented as computer readable instructions on one or more memories or other non-transitory computer readable media, and executed by one or more processors in communication with the one or more memories or other media. In some embodiments, the process 1700 can be implemented as computer readable instructions on the memory 220 and/or the memory 240 and executed by the processor 204 and/or the processor 224. In some embodiments, the process 1700 can be executed by an imaging system. In some embodiments, a brightfield microscopy imaging system can be configured to execute the process 1700. In some embodiments, the brightfield microscopy imaging system can include one or more memories or other non-transitory computer readable media including the process 1700 implemented as computer readable instructions on the one or more memories or other non-transitory computer readable media, and one or more processors in communication with the one or more memories or other media configured to execute the computer readable instructions to execute the process 1700.

At 1704, the process 1700 can receive a brightfield image (e.g., the brightfield image 1600 in FIG. 16) of one or more organoids. In some embodiments, the brightfield image can be preprocessed in order to enhance contrast as described above. In some embodiments, the brightfield image can be a raw image that has not undergone any preprocessing such as contrast enhancement.

At 1708, the process 1700 can determine if the brightfield image is unprocessed (i.e., raw). If the brightfield image is unprocessed (i.e., "YES" at 1708), the process 1700 can proceed to 1712. If the brightfield image is not unprocessed (i.e., "NO" at 1708), the process 1700 can proceed to 1716.

At 1712, the process 1700 can preprocess the brightfield image. In some embodiments, the brightfield image can have pixel intensities ranging from $[0, 2^{16}]$. In some embodiments, the process 1700 can convert the brightfield image to an unsigned byte format, with values ranging from $[0, 255]$. In some embodiments, the process 1700 can convert the brightfield image to another format with less bits than the original pixel intensity. The process 1700 can then stretch and clip each pixel intensity to a desired output range. In some embodiments, the process 1700 can determine an input range for the brightfield image by uniformly stretching the 2nd and 98th percentile of pixel intensities in the brightfield image to an output range $[0, 255]$.

At 1716, the process 1700 can provide the brightfield image to a first trained model. In some embodiments, the first trained model can be the first trained model 1604 in FIG. 16. In some embodiments, the trained model can a neural network. In some embodiments, the neural network can include a Mask-RCNN model.

At 1720, the process 1700 can receive at least one individual tumor organoid from the first trained model (for example, in a 64×64×1 or 32×32×1 image). Each individual tumor organoid can be a portion of the brightfield image.

At 1724, the process 1700 can provide the at least one individual tumor organoid to a second trained model. In some embodiments, the second trained model can include the second trained model 1612 in FIG. 16. In some embodiments, the process 1700 can sequentially provide each individual tumor organoid to the second trained model. In some embodiments, the process 1700 can apply the second trained model to the at least one individual tumor organoid to generate at least one artificial fluorescent image.

At 1728, the process 1700 can receive at least one artificial fluorescent image from the second trained model. Each artificial fluorescent image can be generated based on an individual tumor organoid. The artificial fluorescent image can indicate whether cells included in the tumor organoids are alive or dead.

At 1732, the process 1700 can cause the at least one artificial fluorescent image to be output. In some embodiments, the process 1700 can cause the at least one artificial fluorescent image to be output to at least one of a memory (e.g., the memory 220 and/or the memory 240) and/or a display (e.g., the display 116, the display 208, and/or the display 228). The at least one artificial fluorescent image can be used to provide a live/dead count of cells in each individual organoid. In some embodiments, the process 1700 can cause the at least one artificial fluorescent image to be output to an automatic cell counting process in order to receive an accurate live/dead count of cells, percentage of cells that are viable, and/or a cell count report for each organoid. For example, the process 1700 can cause the at least one artificial fluorescent image to be output to the CellProfiler available at https://cellprofiler.org. In some embodiments, the process 1700 can cause one or more channels of the at least one artificial fluorescent image to be output to an automatic cell counting process in order to receive a cell count report, percentage of cells that are viable, and/or accurate live/dead count of cells in each organoid. In some embodiments, the process 1700 can cause the artificial fluorescent image to be output to a trained model in order to receive a cell count report, percentage of cells that are viable, and/or accurate live/dead count of cells in the artificial fluorescent image. In some embodiments, the process 1700 can cause a combination (e.g., image embeddings combined by concatenation) of the brightfield image and one, two, or three channels of the artificial fluorescent image to be output to an automatic cell counting process in order to receive a cell count report, percentage of cells that are viable, and/or an accurate live/dead count of cells in the artificial fluorescent image.

In some embodiments, at 1732, the process 1700 can identify cells in the artificial fluorescent image by converting each of the channels to grayscale, enhancing and suppressing certain features such as speckles, ring shapes, neurites, dark holes, identifying primary objects belonging to the all cell channel where the typical diameters of these objects (in pixel units) is set anywhere between 2 and 20 with a minimum cross entropy thresholding method at a smoothing scale of 1.3488, and identifying primary objects again belonging to the dead cells channel where typical diameter is anywhere between five and twenty in pixel units. In this way, the process 1700 can generate a cell count report. In some embodiments, the process 1732 can determine if a drug and/or dosage is effective in killing tumor organoid cells based on the live/dead count of cells or percentage of cells that are viable for each organoid. In some embodiments, at 1732, the process 1700 can extrapolate dose response from a distribution of organoid viability at a single concentration.

In some embodiments, the process 1700 can analyze nucleic acid data associated with the one or more tumor organoids. Each tumor organoid included in the one or more tumor organoids can be associated with a specimen (e.g., the specimen the tumor organoid was harvested from). In some embodiments, each specimen can be associated with a patient. The patient can be associated with patient data that can include nucleic acid data. In some embodiments, the nucleic acid data can include whole exome data, transcriptome data, DNA data, and/or RNA data. The nucleic acid data may be used to further analyze the patient. In some embodiments, the process 1700 can associate the artificial fluorescent image with information about the specimen (e.g., the nucleic acid data). In some embodiments, the process 1700 can provide the artificial fluorescent image and the associated information about the specimen to a database. In some embodiments, the database can include at least seven hundred and fifty artificial fluorescent images.

In some embodiments, the process 1700 can generate a report based on the cell count, the cell count report, the nucleic acid data and/or the artificial fluorescent image. In some embodiments, the process 1700 can cause the report to be output to at least one of a memory (e.g., the memory 220 and/or the memory 240) and/or a display (e.g., the display 116, the display 208, and/or the display 228). The process 1700 can then end.

Example 6—Neural Network-Based Model for Predicting TO Drug Response, and Response Prediction from Brightfield Images in the Absence of Fluorescent Labels In some embodiments, a process can cause a brightfield image and one, two, or three channels of the artificial fluorescent image to be output to an automatic cell counting process (for example, a viability estimation process) in order to receive a percentage of cells in the image that are viable (alive).

Figure 18:
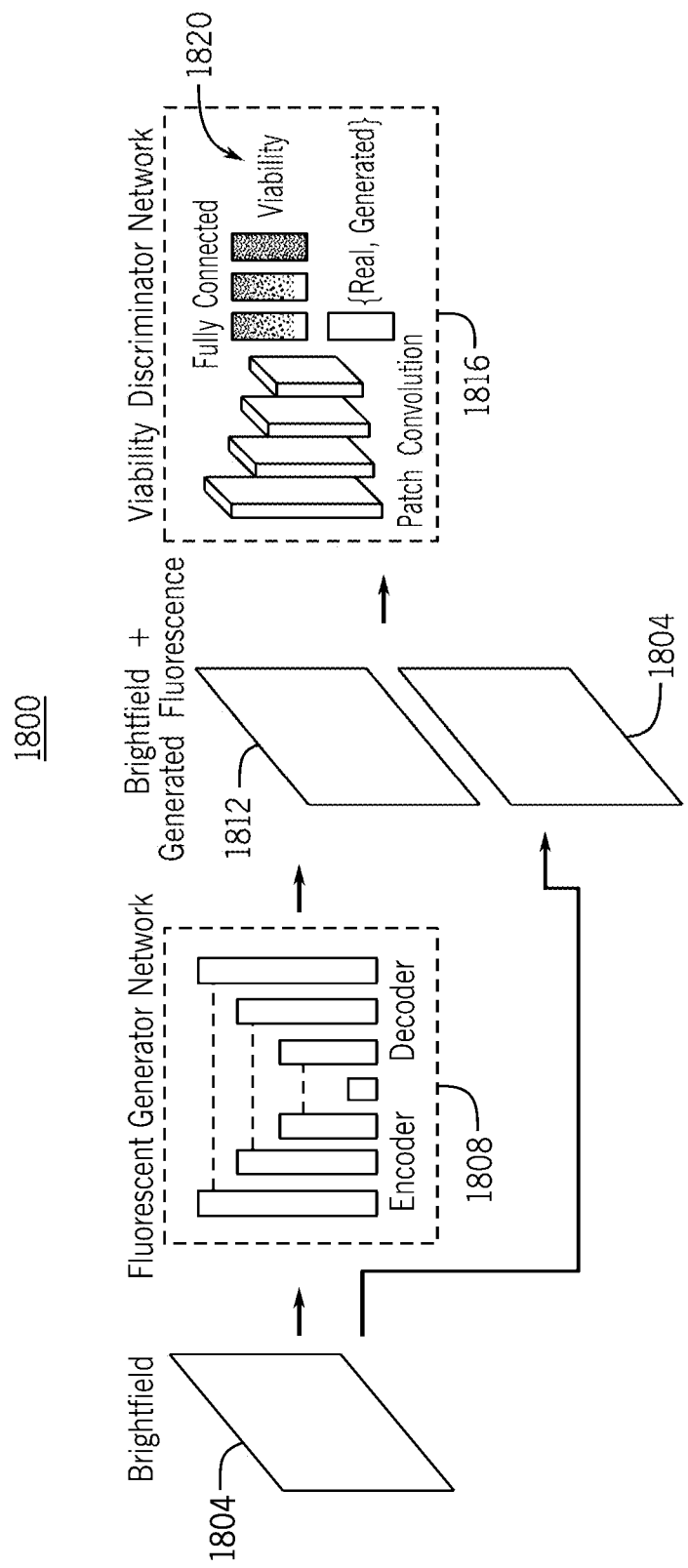
FIG. 18 shows a flow for predicting a viability based on a brightfield image.

FIG. 18 illustrates a flow 1800 for predicting a viability 1820 based on a brightfield image 1804. The brightfield image 1804 can be a three-channel brightfield image of tumor organoids and/or and cells. The flow 1800 can include providing the brightfield image 1804 to a generator 1808. In some embodiments, the generator 1808 can generate an artificial fluorescent image 1812 based on the brightfield image 1804. The flow 1800 can include providing the brightfield image 1804 and the artificial fluorescent image 1812 to a discriminator 1816. The discriminator can generate the viability 1820 based on the brightfield image 1804 and the artificial fluorescent image 1812.

Figure 19:
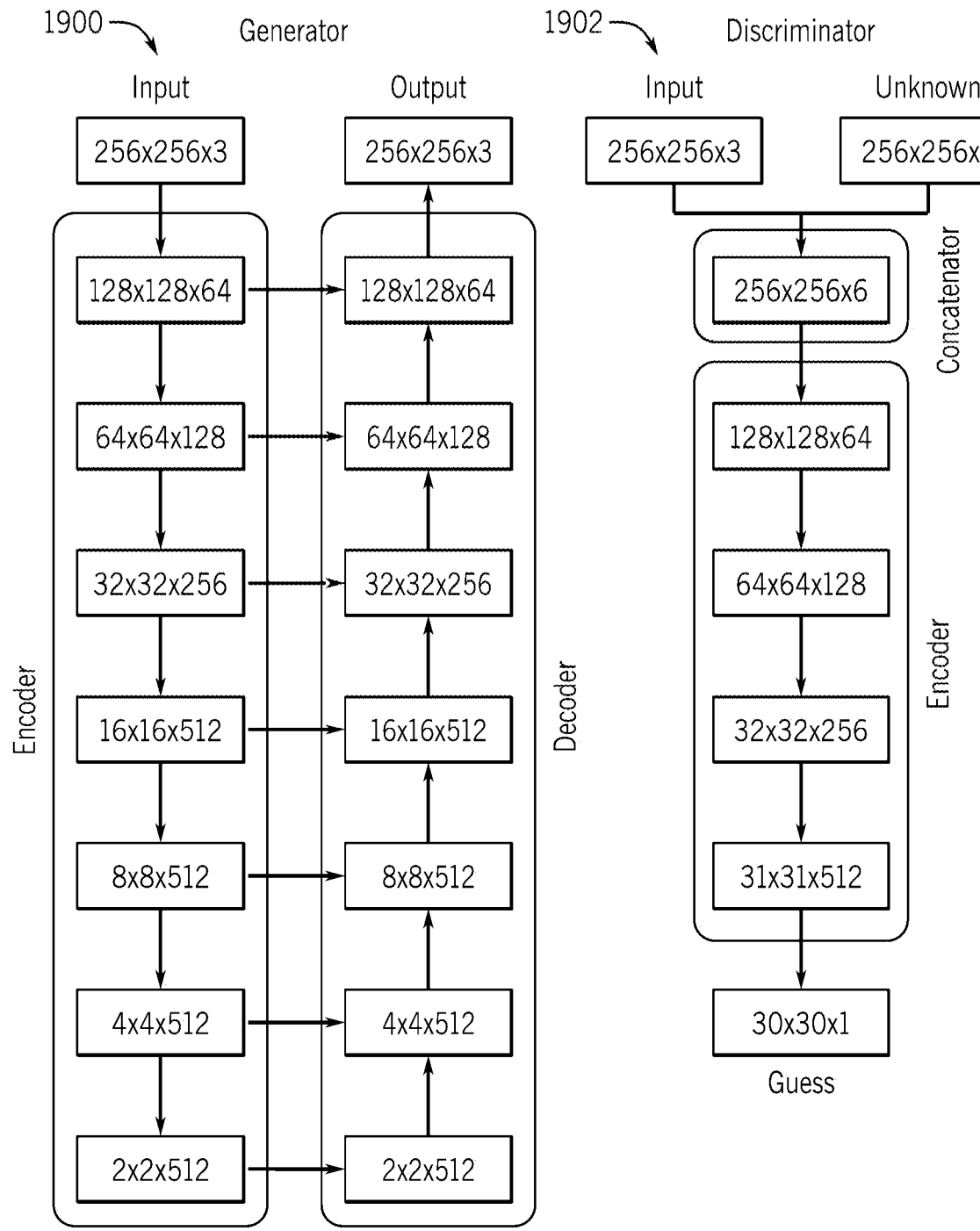
FIG. 19 shows an exemplary generator and an exemplary discriminator.

Referring now to FIG. 18 as well as FIG. 19, an exemplary generator 1900 and an exemplary discriminator 1902 are shown. In some embodiments, the discriminator 1902 can be used to train the generator 1900. In some embodiments, the generator 1900 and the discriminator 1902 can be included in a regularized conditional adversarial (RCA) network.

In some embodiments, the generator 1900 can include an encoder-decoder U-Net network. In some embodiments, the U-Net can include skip connections. In some embodiments, the generator 1900 can receive a two-dimensional brightfield image (e.g., a 1024×1024 brightfield image). In some embodiments, the generator 1900 can generate a normalized, three-channel, high-resolution 1024×1024×3 output fluorescent image based on the brightfield image, where the three channels correspond to Hoechst 33342 all nuclei stained readout, Caspase-3/7 apoptotic stained readout, and TOPRO-3 dead cell stained readout, respectively.

Figure 20:
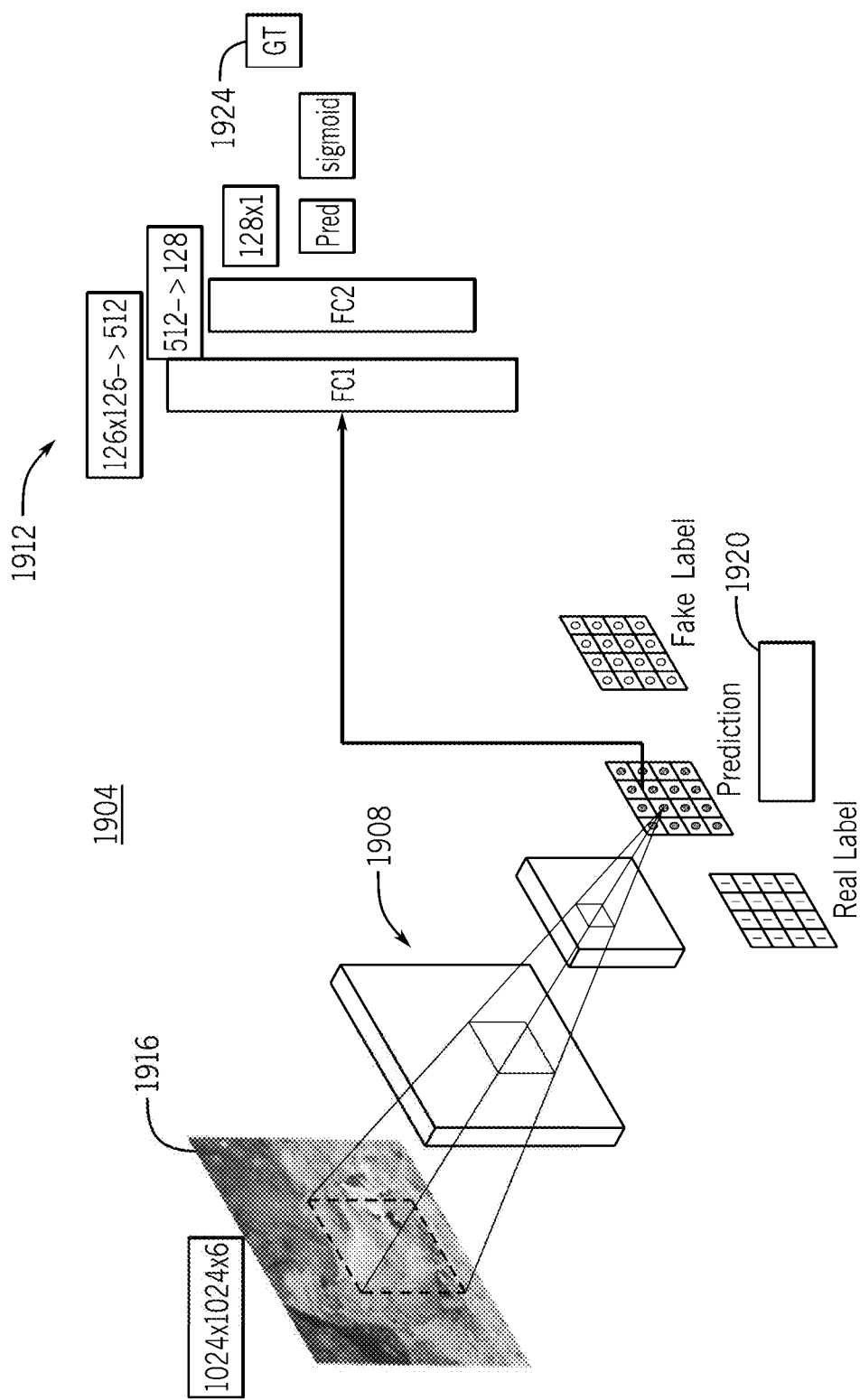
FIG. 20 shows a discriminator that can generate a viability prediction based on a brightfield image and an artificial fluorescent image.

Referring now to FIGS. 18 and 19 as well as FIG. 20, a discriminator 1904 can generate a viability prediction 1924 based on a brightfield image and an artificial fluorescent image. The discriminator 1904 can include an encoder branch 1908 and a fully-connected branch 1912. In some embodiments, the encoder branch 1908 can include a 70×70 patchGAN. In some embodiments, the encoder branch 1908 can receive a concatenated brightfield image and a fluorescent image 1916 of size 1024×1024×6. In some embodiments, the encoder branch 1908 can generate an output prediction map 1920 (e.g., an output prediction map of size 126×126×1). The fully-connected branch 1912 can then generate a viability prediction 1924 based on the output prediction map 1920. In some embodiments, the fully-connected branch 1912 can include a number of fully-connected layers (e.g., two fully-connected layers) and a sigmoid activation layer that outputs the viability prediction 1924. The viability prediction 1924 can indicate viability. In some embodiments, the viability prediction 1924 can be and/or range from zero (indicative of no viability) to one (indicative of high viability).

Training

In testing, the generator 1900 and the discriminator 1902 were trained on eight thousand four hundred and fifteen paired brightfield and 3-channel fluorescence images from colon adenocarcinoma TO screening experiments, each with associated calculated drug responses based on TO-PRO-3 viability. In some embodiments, an objective function (for example, loss function used for training) can include an additional mean squared error loss in a discriminator objective to regress against the branch of the discriminator that computes overall viability per brightfield image. Exemplary loss functions for the discriminator 1902 and the generator 1900 are given below:

$$D_{Loss}=MSE_{Loss}\{Real\ Prediction,1\}+MSE_{Loss}\{Fake\ Prediction,0\}+MSE_{Loss}\{Predicted\ Viability,Viability\}\ G_{Loss}=MSE_{Loss}\{Fake\ Prediction,1\}+MAE_{Loss}\{Fake\ Fluorescent,Real\ Fluorescent\}+SSIM\{Fake\ Fluorescent,Real\ Fluorescent\}$$

Weights for the discriminator 1902 can be updated by minimizing $D_{Loss}$, and weights for the generator 1900 can be updated by maximizing $G_{Loss}$.

Validation

In validation, representative images of real versus generated fluorescence demonstrated nearly indistinguishable visual matching. These results were confirmed using two quantitative metrics: the structural similarity index (SSIM) as well as the root mean squared error (RMSE). The reported average SSIM and RMSE values across 1,526 samples of the colon adenocarcinoma TO used in the screening experiment were 0.90 and 0.13924 respectively. For the gastric TO line, the reported average SSIM and RMSE values across 9200 samples were 0.898 and 0.136, respectively.

TO Description, Image Analysis, and Generation of Images for Training Data

TOs were dissociated into single cells and resuspended in a 30:70% mix of GFR Matrigel:growth media at a concentration of 100 cells/μl. The solution was added to 384-well assay plates (Corning) at 20 μl per well for a final concentration of 2,000 cells per well. Assay plates were covered with a Breathe-Easy sealing membrane (Sigma Aldrich) to prevent evaporation. TOs were grown for 72 hours before drug addition. Drugs were prepared in growth media with 2.5 μM Caspase-3/7 Green Apoptosis Assay Reagent (Essen Bioscience). Serial dilutions of each molecule were prepared in 384-well polystyrene plates (Nunc). Seven 10-fold dilutions were made for each compound with the high dose being 10 μM. Select compounds were limited to a high dose of 1 μM by maximum solubility. Diluted drug was added to the assay plate using an Integra Viaflo pipette (Integra) mounted on an Integra Assist Plus Pipetting Robot (Integra). Assay plates were again covered with a Breathe-Easy sealing membrane and TOs were exposed to drugs for another 72 hours before imaging.

Prior to imaging, TOs were incubated with 4 μM Hoechst 33342 (Fisher Scientific) and 300 nM TO-PRO-3 Iodide (642/661) (Invitrogen) for 1.5-2 hours. Assay plates were imaged using an ImageXpress Micro Confocal (Molecular Devices) at 10× magnification so that ~100-200 TOs were imaged per well. The multiplexed fluorescence images were 1024×1024×3 RGB images, where red corresponds to dead cells (TO-PRO-3), green to apoptotic cells (Caspase-3/7), and blue to nuclei (Hoechst 33342). All wavelength channels underwent a simple intensity rescaling contrast enhancement technique to brighten and sharpen the TOs/cells as well as remove background noise.

Images were acquired as 4×15 μm Z-stacks and the 2D projections were analyzed to assess cell viability. Confocal images were analyzed using the MetaXpress software (Molecular Devices) custom module editor feature to design an analysis module that identified TOs by clusters of Hoechst 33342 staining, individual cells by Hoechst 33342 staining, and dead/dying cells by either TO-PRO-3 or Caspase-3/7 staining. The result of this analysis module is a spreadsheet detailing the number of live and dead cells for every individual organoid. Each viability value was equal to or greater than 0 (0% of cells viable) and equal to or less than 1 (100% of cells viable).

Viability calculation=sum total of all live cells in the site/sum total of all cells in the site (gives a proportion of live cells per site). More effective drugs will have lower viabilities (more cells die) at higher doses compared to less effective drugs, which have higher viabilities.

The mean viability for all organoids per site (for example, per image) was obtained from the MetaXpress software readout. For each image added to a training data set used to train the viability discriminator, the image was stored with the mean viability associated with that image as a label or metadata. The images had a resolution of 1024×1024 and were randomly flipped as a data augmentation step before being used as training data.

The training data set in this example included seven thousand images representing 15 culture plates.

The percentage of viable cells per TO was calculated based on the image analysis described above. TOs with fewer than three cells, TOs larger than the top one percent by size, and wells with fewer than 20 TOs detected were excluded from analysis.

In another example, an AUC may be used as metadata or a label to generate training data. The mean viability for all TOs at a given drug concentration was used in dose-response curves to calculate AUC. AUC was calculated using the computeAUC function using settings for "actual" AUC of the R Package PharmacoGx (v1.17.1). Heatmaps of AUC values were generated using the Pheatmap package (v1.0.12) in R. Scatterplots of AUC values were generated using the ggplot2 package (v3.3.0) in R.

Figure 21:
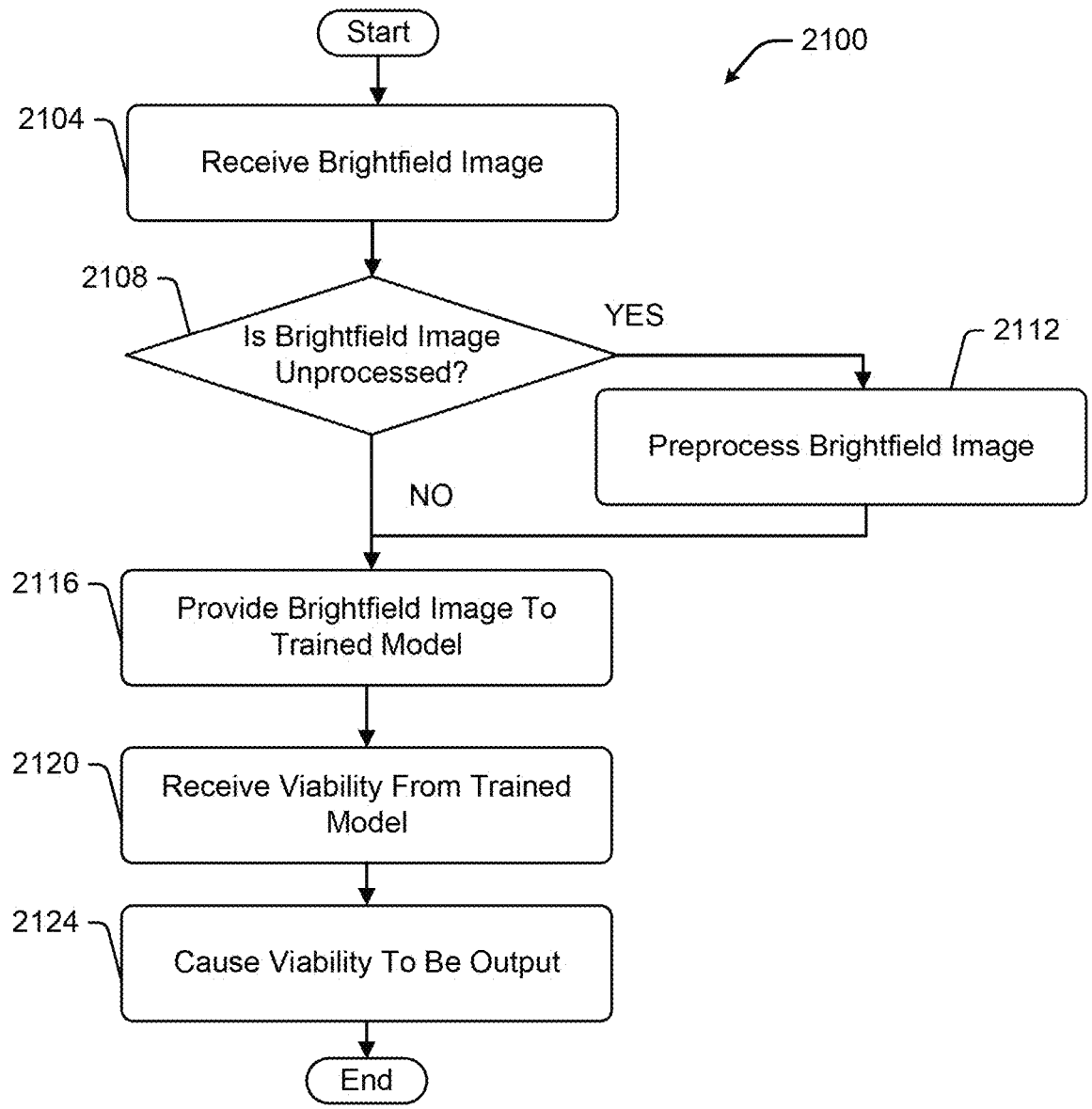
FIG. 21 shows a process for generating a viability value.

Referring now to FIGS. 18-20 as well as FIG. 21, a process 2100 for generating a viability value is shown. The process 2100 can be implemented as computer readable instructions on one or more memories or other non-transitory computer readable media, and executed by one or more processors in communication with the one or more memories or other media. In some embodiments, the process 2100 can be implemented as computer readable instructions on the memory 220 and/or the memory 240 and executed by the processor 204 and/or the processor 224. In some embodiments, the process 2100 can be executed by an imaging system. In some embodiments, a brightfield microscopy imaging system can be configured to execute the process 2100. In some embodiments, the brightfield microscopy imaging system can include one or more memories or other non-transitory computer readable media including the process 2100 implemented as computer readable instructions on the one or more memories or other non-transitory computer readable media, and one or more processors in communication with the one or more memories or other media configured to execute the computer readable instructions to execute the process 2100.

At 2104, the process 2100 can receive a brightfield image (e.g., the brightfield image 1804 in FIG. 18) of one or more organoids. In some embodiments, the brightfield image can be preprocessed in order to enhance contrast as described above. In some embodiments, the brightfield image can be a raw image that has not undergone any preprocessing such as contrast enhancement.

At 2108, the process 2100 can determine if the brightfield image is unprocessed (i.e., raw). If the brightfield image is unprocessed (i.e., "YES" at 2108), the process 2100 can proceed to 2112. If the brightfield image is not unprocessed (i.e., "NO" at 2108), the process 2100 can proceed to 2116.

At 2112, the process 2100 can preprocess the brightfield image. In some embodiments, the brightfield image can have pixel intensities ranging from [0,2^16]. In some embodiments, the process 2100 can convert the brightfield image to an unsigned byte format, with values ranging from [0, 255]. In some embodiments, the process 2100 can convert the brightfield image to another format with less bits than the original pixel intensity. The process 2100 can then stretch and clip each pixel intensity to a desired output range. In some embodiments, the process 2100 can determine an input range for the brightfield image by uniformly stretching the 2nd and 98th percentile of pixel intensities in the brightfield image to an output range [0,255].

At 2116, the process 2100 can provide the brightfield image to a trained model. In some embodiments, the trained model can include a generator (e.g., the generator 1808 and/or the generator 1900) and the discriminator (e.g., the discriminator 1816 and/or the discriminator 1904). In some embodiments, the process 2100 can include providing the brightfield image to the generator, receiving an artificial fluorescent image from the process, concatenating the brightfield image with the artificial fluorescent image to generate a concatenated image, and providing the concatenated image to the discriminator. In some embodiments, the process 2100 can include applying the trained model to the brightfield image to generate the fluorescent image.

At 2120, the process 2100 can receive a viability (e.g., a viability value) from the trained model. In some embodiments, the process 2100 can receive the viability from the discriminator 1904. In some embodiments, the viability can be the viability 1820 and/or the viability prediction 1924.

At 2124, the process 2100 can cause the viability to be output. In some embodiments, the process 2100 can cause viability to be output to at least one of a memory (e.g., the memory 220 and/or the memory 240) and/or a display (e.g., the display 116, the display 208, and/or the display 228). In some embodiments, the process 2100 can generate a report based on the viability. In some embodiments, the process 2100 can analyze nucleic acid data associated with the one or more organoids. Each organoid included in the one or more organoids can be associated with a specimen (e.g., the specimen the organoid was harvested from). In some embodiments, each specimen can be associated with a patient. The patient can be associated with patient data that can include nucleic acid data. In some embodiments, the nucleic acid data can include whole exome data, transcriptome data, DNA data, and/or RNA data. The nucleic acid data may be used to further analyze the patient. In some embodiments, the process 2100 can associate the artificial fluorescent image with information about the specimen (e.g., the nucleic acid data). In some embodiments, the process 2100 can provide the artificial fluorescent image, the associated information about the specimen, and/or the viability to a database. In some embodiments, the database can include at least seven hundred and fifty artificial fluorescent images.

In some embodiments, the process 2100 can cause the report to be output to at least one of a memory (e.g., the memory 220 and/or the memory 240) and/or a display (e.g., the display 116, the display 208, and/or the display 228). The process 2100 can then end.

The present disclosure has described one or more preferred embodiments, and it should be appreciated that many equivalents, alternatives, variations, and modifications, aside from those expressly stated, are possible and within the scope of the invention.

What is claimed:

1. A method of generating an artificial fluorescent image of cells without a fluorescent stain, comprising:
   receiving, by a computer system having at least one processor, a brightfield image generated by a brightfield microscopy imaging modality of at least a portion of cells included in a specimen;
   applying by the processor, to the brightfield image, at least one trained model, wherein the trained model is trained to modify pixel intensities of the brightfield image so as to generate the artificial fluorescent image of the cells based on the brightfield image; and
   generating the artificial fluorescent image by the trained model.

2. The method of claim 1, wherein the specimen comprises at least one tumor organoid.

3. The method of claim 2, wherein the artificial fluorescent image is indicative of whether the portion of the cells included in the specimen are alive or dead.

4. The method of claim 2, wherein the at least one tumor organoid is associated with a colorectal cancer, a gastric cancer, a breast cancer, a lung cancer, an endometrial cancer, a colon cancer, a head and neck cancer, an ovarian cancer, a pancreatic cancer, a gastric cancer, a hepatobiliary cancer, or a genitourinary cancer.

5. The method of claim 2, wherein the at least one tumor organoid is plated on a well plate comprising at least ninety six wells.

6. The method of claim 2, further comprising:
   outputting the artificial fluorescent image to a drug screening process to determine effectiveness of a drug used to treat the at least one tumor organoid.

7. The method of claim 2, wherein the at least one tumor organoid is included in a first group of tumor organoids, and the method further comprises:
   providing a second brightfield image to the trained model; and
   receiving a second artificial fluorescent image from the trained model, wherein the second brightfield image comprises a second group of tumor organoids, and the second artificial fluorescent image is indicative of whether cells included in the second group are alive or dead.

8. The method of claim 7, wherein the second brightfield image comprises a view of the second group of tumor organoids, the second brightfield image being generated a predetermined time period after the brightfield image is generated, wherein the second artificial fluorescent image is indicative of whether cells included in the second group are alive or dead.

9. The method of claim 1, further comprising:
   providing to the trained model a plurality of brightfield images generated by a brightfield microscopy imaging modality of the at least a portion of cells, the plurality of brightfield images generated after the brightfield image is generated; and
   receiving a corresponding plurality of artificial fluorescent images from the trained model.

10. The method of claim 9, wherein each brightfield image in the plurality of brightfield images is generated no more than twenty-four hours apart.

11. The method of claim 9, wherein each brightfield image in the plurality of brightfield images is generated no more than seventy-two hours apart.

12. The method of claim 9, wherein each brightfield image in the plurality of brightfield images is generated no more than one week apart.

13. The method of claim 1 further comprising:
concatenating the brightfield image to the artificial fluorescent image to generate a concatenated image; and
generating a viability value based on the concatenated image.

14. The method of claim 1, wherein the trained model comprises an artificial neural network.

15. The method of claim 14, wherein the artificial neural network comprises a generative adversarial network (GAN).

16. The method of claim 1, wherein the trained model is trained based on a loss function comprising a structural similarity index (SSIM).

17. The method of claim 1 further comprising:
generating a report based on the artificial fluorescent image.

18. The method of claim 1, wherein the trained model is trained based on a loss function comprising a discriminator loss, or a generator loss and a discriminator loss.

19. The method of claim 1 further comprising preprocessing the brightfield image to increase contrast levels.

20. The method of claim 19, wherein the preprocessing comprises:
converting the brightfield image to an unsigned byte format; and
adjusting each pixel intensity included in the brightfield image to a desired output range of [0-255].

21. The method of claim 1 further comprising preprocessing brightfield images and fluorescent images included in training data used to train the trained model.

22. The method of claim 1, wherein the trained model comprises a generator, the generator being trained in part by a discriminator.

23. The method of claim 1, further comprising analyzing nucleic acid data associated with the specimen, and including the results of the analysis in a report.

24. The method of claim 1, further comprising:
associating the artificial fluorescent image with information about the specimen; and
providing the artificial fluorescent image and the associated information about the specimen to a database comprising at least seven hundred and fifty artificial fluorescent images.

25. The method of claim 24, wherein the information about the specimen comprises a cancer diagnosis associated with the specimen.

26. The method of claim 24, further comprising:
applying one or more drugs to the specimen prior to the generation of the brightfield image;
wherein the information about the specimen comprises a diagnosis associated with the specimen and an identification of the one or more drugs.

27. A brightfield microscopy imaging modality configured to execute the method of claim 1.

28. The brightfield microscopy imaging modality of claim 27, wherein the brightfield microscope imaging modality comprises a brightfield microscope.

29. An organoid analysis system comprising at least one processor and at least one memory, the system configured to
receive a brightfield image generated by a brightfield microscopy imaging modality from at least a portion of cells included in a specimen;
apply, via the processor, to the brightfield image, at least one model trained to modify pixel intensities of the brightfield image so as to generate an artificial fluorescent image based on the brightfield image without a fluorescent stain, the artificial fluorescent image being indicative of whether the cells included in the specimen are alive or dead;
generating the artificial fluorescent image by the trained model; and
output the artificial fluorescent image to at least one of a memory or a display.

30. A method of generating an artificial fluorescent image of cells without a fluorescent stain, comprising:
receiving, from a computer system having at least one processor, a brightfield image generated by a brightfield microscopy imaging modality from at least a portion of cells included in a specimen;
applying, by the processor, to the brightfield image, at least one model trained to modify pixel intensities of the brightfield image so as to generate an artificial fluorescent image of the cells based on the brightfield image, the artificial fluorescent image being indicative of whether the cells included in the specimen are alive or dead;
generating the artificial fluorescent image by the trained model; and
generating a report based on the artificial fluorescent image of the cells.

* * * * *